United States Patent [19]
Cundari et al.

[11] Patent Number: 6,091,981
[45] Date of Patent: Jul. 18, 2000

[54] CLINICAL TISSUE EXAMINATION

[75] Inventors: Michael Anthony Cundari, Hingham; Alan Irving West, Hopkinton; Brian David Noble, Weymouth; Troy William Roberts, Pepperell; David Raymond Widder, Newton, all of Mass.

[73] Assignee: Assurance Medical Inc., Hopkinton, Mass.

[21] Appl. No.: 08/931,573

[22] Filed: Sep. 16, 1997

[51] Int. Cl.⁷ ...................................................... A61B 5/05
[52] U.S. Cl. ........................................ 600/407; 600/587
[58] Field of Search ................................... 600/407, 567, 600/561, 587, 437–444

[56] References Cited

U.S. PATENT DOCUMENTS

Re. 30,446  12/1980  Meyers et al. ........................... 128/736
Re. 32,000  10/1985  Sagi ......................................... 128/736

(List continued on next page.)

FOREIGN PATENT DOCUMENTS

PCT/US96/
17173  10/1996  European Pat. Off. .
2 086 575  5/1982  United Kingdom .

OTHER PUBLICATIONS

Sarvazyan, A., "Knowledge–Based Mechanical Imaging", Tenth IEEE Symposium on Computer–Based Medical Systems, Jun. 11–13, 1997, pp. 120–125.

Sarvazyan, A. "Knowledge–Based Mechanical Imaging of the Prostate", Medical Technologies & Programs: A Forcast for the future, Aug. 14–17, 1997, pp. 87–94.

E.J. Chen et al., "Ultrasound Tissue Displacement Imaging with Application to Breast Cancer", 1995, Ultrasound in Med. & Biol., vol. 21, No. 9, pp. 1153–1156, Michigan, U.S.A.

R.S. Fearing et al., "A Tactile Sensing Finger Tip for a Dextrous Hand", Oct. 1986, 5th SPIE Intelligent Robotics and Computer Vision, pp. 1–10, Cambridge, Massachusetts.

Brian S. Garra, et al. "Elastography of Breast Lesions: Initial Clinical Results" 1997, Radiology, vol. 202, pp. 69–86.

F. Kallel et al., "Fundamental Limitations on the Contrast-–Transfer Efficiency in Elastography: an Analytic Study", 1996, Ultrasound in Med. & Biol., vol. 22, No. 4, pp. 463–470.

Dr. Ricki Lewis, "New Imaging Technology May Detect Early Cancer", Biophotonics in Action, Oct. 1996, Photonics Spectra, pp. 52–53.

G. Piperno et al., "Breast Cancer Screening by Impedance Measurements", 1990, Frontiers Med. Biol. Engng. vol. 2, No. 2, pp. 111–117.

G.I. Pressman et al., "A Transducer for the Continuous External Measurement of Arterial Blood Pressure", 1960s, IEEE Transactions on Bio–Medical Electronics.

(List continued on next page.)

*Primary Examiner*—Brian L. Casler
*Attorney, Agent, or Firm*—Fish & Richardson P.C.

[57] ABSTRACT

This invention concerns performing clinical tissue examination with a device that includes sensors which produces signals in response to pressure imposed on the sensors as the sensors are pressed against the tissue. The sensors generate signals in response to pressure imposed on the sensors when pressed against a selected region of tissue. That pressure varies in accordance with properties of underlying tissue structures. An image of the region of tissue is generated based on the signals generated by the sensors. The image is then displayed. The image represents the pressure imposed on the sensors. The image that is displayed may be a three dimensional image of the region of tissue. The signals produced by the sensors can also be processed to detect an underlying tissue structure in the region of tissue. A location or a map of the detected underlying tissue structure relative to a reference point is generated and displayed. The results of a current examination are compared to those of a previous examination.

98 Claims, 28 Drawing Sheets

(8 of 28 Drawing Sheet(s) Filed in Color)

U.S. PATENT DOCUMENTS

| Number | Date | Name | Class |
|---|---|---|---|
| 3,154,789 | 11/1964 | Lewis, Jr. | 2/104 |
| 3,308,476 | 3/1967 | Kleesattel . | |
| 3,323,352 | 6/1967 | Branson . | |
| 3,744,490 | 7/1973 | Fernandez | 128/2.05 |
| 3,847,139 | 11/1974 | Flam | 128/2 H |
| 3,854,471 | 12/1974 | Wild | 128/2 V |
| 3,880,145 | 4/1975 | Blick | 128/2.05 |
| 3,970,862 | 7/1976 | Edelman et al. | 307/88 ET |
| 3,972,227 | 8/1976 | Tomilov | 73/67.7 |
| 3,996,922 | 12/1976 | Basham | 128/2 R |
| 4,001,951 | 1/1977 | Fasse | 35/17 |
| 4,023,562 | 5/1977 | Hynecek et al. | 128/2.05 E |
| 4,025,165 | 5/1977 | Sollish et al. | 350/161 S |
| 4,132,224 | 1/1979 | Randolph | 128/2 S |
| 4,134,218 | 1/1979 | Adams et al. | 35/17 |
| 4,135,497 | 1/1979 | Meyers et al. | 128/2 H |
| 4,144,877 | 3/1979 | Frei et al. | 128/2 S |
| 4,159,640 | 7/1979 | Leveque et al. | 73/81 |
| 4,190,058 | 2/1980 | Sagi | 128/736 |
| 4,212,306 | 7/1980 | Mahmud | 128/665 |
| 4,219,708 | 8/1980 | Rubey | 200/61.47 |
| 4,250,894 | 2/1981 | Frei et al. | 128/774 |
| 4,286,602 | 9/1981 | Guy | 128/665 |
| 4,291,708 | 9/1981 | Frei et al. | 128/734 |
| 4,458,694 | 7/1984 | Sollish et al. | 128/734 |
| 4,503,865 | 3/1985 | Shishido | 128/774 |
| 4,524,778 | 6/1985 | Brown, Jr. et al. | 128/736 |
| 4,555,953 | 12/1985 | Dario et al. | 73/862.04 |
| 4,570,638 | 2/1986 | Stoddart et al. | 128/665 |
| 4,600,011 | 7/1986 | Watmough | 128/664 |
| 4,641,659 | 2/1987 | Sepponen | 128/653 |
| 4,641,661 | 2/1987 | Kalarickal | 128/744 |
| 4,651,749 | 3/1987 | Sagi | 128/736 |
| 4,657,021 | 4/1987 | Perry et al. | 128/630 |
| 4,729,378 | 3/1988 | Trittenbass | 128/645 |
| 4,737,109 | 4/1988 | Abramson | 434/267 |
| 4,768,516 | 9/1988 | Stoddart et al. | 128/665 |
| 4,774,961 | 10/1988 | Carr | 128/736 |
| 4,790,329 | 12/1988 | Simon | 128/749 |
| 4,793,354 | 12/1988 | Wright et al. | 128/630 |
| 4,807,637 | 2/1989 | Bjorkhom | 128/664 |
| 4,810,875 | 3/1989 | Wyatt | 250/227 |
| 4,817,623 | 4/1989 | Stoddart et al. | 128/665 |
| 4,873,982 | 10/1989 | Morrison | 128/630 |
| 4,886,070 | 12/1989 | Demarest | 128/675 |
| 4,944,298 | 7/1990 | Sholder | 128/419 |
| 5,010,772 | 4/1991 | Bourland et al. | 73/862.04 |
| 5,012,817 | 5/1991 | Zeilinski et al. | 128/744 |
| 5,031,634 | 7/1991 | Simon | 128/754 |
| 5,079,698 | 1/1992 | Grenier et al. | 364/413.13 |
| 5,099,848 | 3/1992 | Parker et al. | 128/661.07 |
| 5,140,989 | 8/1992 | Lewis et al. | 128/665 |
| 5,143,079 | 9/1992 | Frei et al. | 128/734 |
| 5,212,637 | 5/1993 | Saxena | 364/413.26 |
| 5,221,269 | 6/1993 | Miller et al. | 604/281 |
| 5,265,612 | 11/1993 | Sarvazyan et al. | 128/660.01 |
| 5,301,681 | 4/1994 | DeBan et al. | 128/736 |
| 5,301,682 | 4/1994 | Debbas | 128/737 |
| 5,333,612 | 8/1994 | Wild | 128/660.9 |
| 5,511,561 | 4/1996 | Wanderman et al. | 128/779 |
| 5,524,636 | 6/1996 | Sarvazyan et al. | 128/774 |
| 5,678,565 | 10/1997 | Sarvazyan | 128/774 |
| 5,785,663 | 7/1998 | Sarvazyan | 600/587 |
| 5,795,308 | 8/1998 | Russin | 600/567 |
| 5,807,276 | 9/1998 | Russin | 600/567 |
| 5,833,633 | 11/1998 | Sarvazyan | 600/587 |
| 5,833,634 | 11/1998 | Laird et al. | 600/587 |
| 5,836,894 | 11/1998 | Sarvazyan | 600/587 |
| 5,840,023 | 11/1998 | Oraevsky et al. | 600/407 |
| 5,860,934 | 1/1999 | Sarvazyan | 600/587 |

OTHER PUBLICATIONS

Martin Feder et al., "Transducer Characteristics for Ultrasonic Stereoholography", Dec. 1976, Bull. N.Y. Acad. Med., vol. 52, No. 10, pp. 1207–1223.

B.D. Sollish et al., "Microprocessor–Assisted Screening Techniques", 1981, Israel J. Med. Sci., pp. 859–864, Israel.

R.G. Stevens et al., "The use of Difference of Gaussian Image Filtering to Assess Objectively the Correlations Between Breast Vascularity and Breast Cancer", 1988, Phys. Med. Biol., vol. 33, No. 12, pp. 1417–1431, U.K.

KEY: 0.09 0.31 0.56 0.78

KEY: 0.09 0.31 0.56 0.78

KEY: 0.09 0.31 0.56 0.78

KEY: 0.09 0.31 0.56 0.78

KEY: 0.09 0.31 .056 0.78

KEY: 0.09 0.31 .056 0.78

KEY: 0.09 0.31 0.56 0.78

KEY: 0.09 0.31 0.56 0.78

1210  KEY: 0.02  0.48  0.94  1.39  1.85

KEY: 0.02  0.48  0.94  1.39  1.85

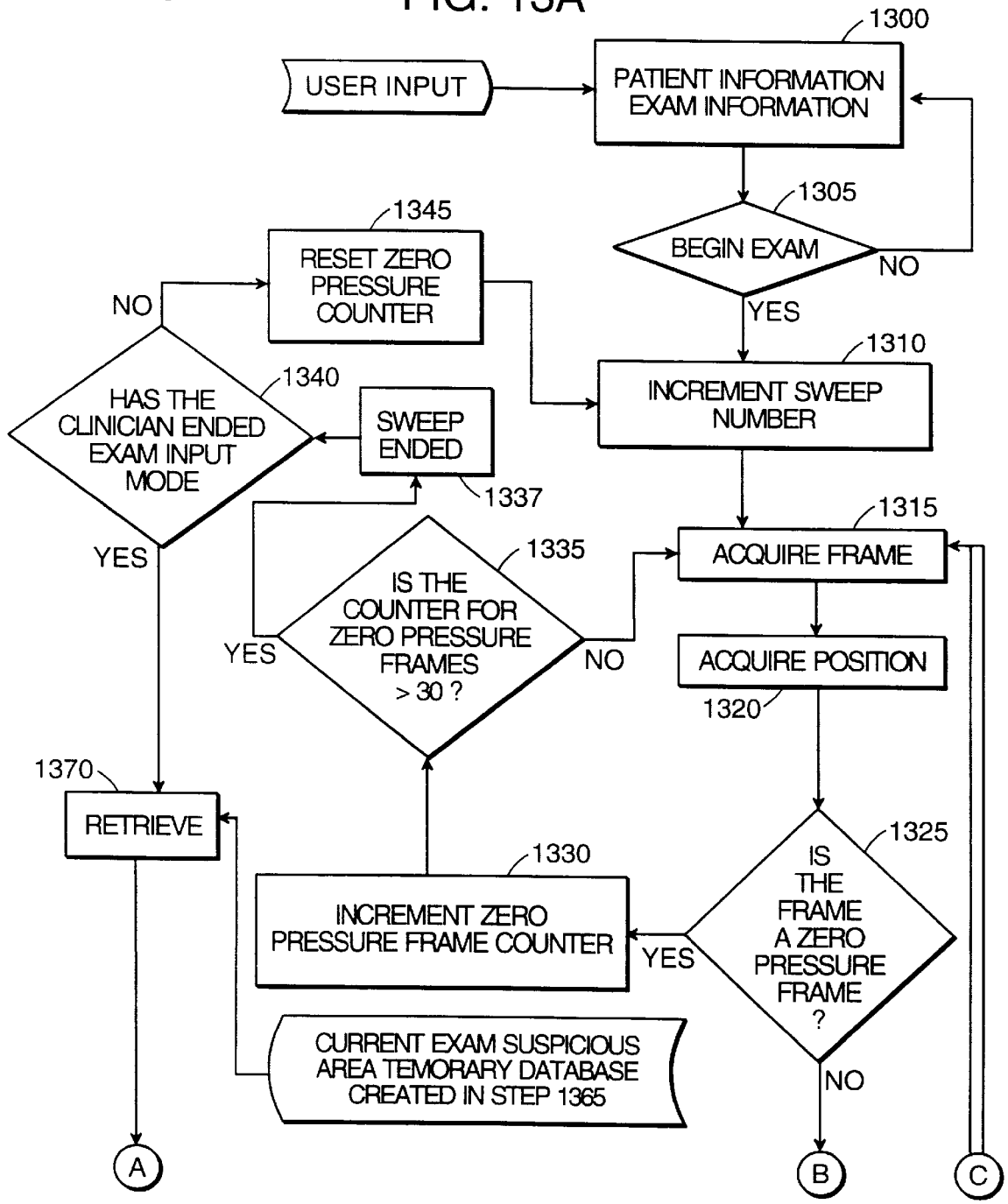

| i | CENTER SUSPICIOUS AREA LATERAL | AXIAL | AVERAGE SUSPICIOUS AREA PRESSURE SIGNATURES | SIZE OF SUSPICIOUS AREA | PROFILE CHARACTERISTIC |
|---|---|---|---|---|---|
| 1 | LATERAL i | AXIAL i | [LATERAL i, AXIAL i, P i] | A i | CURVENESS i |
| 2 | LATERAL i | AXIAL i | [LATERAL i, AXIAL i, P i] | A i | CURVENESS i |
| 3 | LATERAL i | AXIAL i | [LATERAL i, AXIAL i, P i] | A i | CURVENESS i |

FIG. 20

CLINICAL TISSUE EXAMINATION

CROSS REFERENCE TO RELATED APPLICATIONS

This invention relates to U.S. Ser. No. 08/757,466, filed Nov. 27, 1996 and U.S. Ser. No. 08/782,442, filed Jan. 17, 1997.

BACKGROUND

This invention relates to tissue examination.

All women are at risk for breast cancer. This risk increases as a woman ages. Women are generally considered to be at increased risk for developing breast cancer if they have one or more of the following risk factors: a family history of breast cancer, a previous diagnosis of a malignant breast tumor or other gynecological cancers, hormonal factors, or not having had any children or having the first child later in their child bearing years. Even so, the majority of all breast cancers occur in women who apparently do not have identifiable risk factors.

Breast cancer cannot currently be prevented. But detecting and treating it at an early stage, when the tumor is small and has not spread beyond the breast, can increase the chances of survival significantly. However, not all breast cancers are currently detected at this early stage. Therefore, screening for breast cancer has become a critical aspect in the overall management of this disease.

The techniques currently used in the United States to screen for breast cancer and other breast conditions include monthly Breast Self Examination (BSE), mammography, and clinical breast examination.

Breast Self Examination is manual examination of a woman's breast tissue by the woman herself. During such examinations, it is typically recommended that a woman examine her breasts at the same time each month, 7–10 days after the first day of her last menstrual cycle. It is also typically recommended that she should report to her physician anything she feels that is new or that has changed since her prior exam.

A mammogram is an x-ray procedure that allows visualization of the internal structure of the breast. It is used as both a screening and diagnostic tool for breast abnormalities. It is generally recommended that women over 40 should have annual mammography so that any breast cancer can be detected early. However, many women still do not have annual mammographies.

Moreover, a mammography may miss a portion of breast cancers, especially in pre-menopausal women, in part because of reduced effectiveness of mammography in young women who generally have radiologically dense breast tissue. The accuracy of mammography also largely depends on the ability and experience of the radiologist who reads the images.

Clinical breast examinations are routinely performed by gynecologists or other primary care physicians. Generally, clinicians perform clinical breast examination to determine whether there are any foreign structures in the breast which may be carcinomas. Clinicians are interested in different kinds of information in performing a breast examination. For example, they are interested in the nature of foreign structures encountered and the degree of change since a previous examination (such as change in size of the structures and their total number). Clinical breast examination is an important tool in the early detection of breast cancer. Combined with mammography, clinical breast examination has been shown to be effective in detecting early breast cancer.

During clinical breast examination, clinicians generally examine the breast manually. Clinicians manipulate the tissue by hand, typically using the three middle fingers, to determine whether any foreign structures are encountered. If they discover a foreign structure during the examination, they may use their fingers to move the foreign structure and to examine its mobility, shape, density, and other characteristics.

In order to keep track of changes from examination to examination, clinicians generally use written records or their own recollection of the characteristics of various structures. If they decide during an examination that a structure warrants further examination because of changes since the last examination or because of the structure's current characteristics, they may prescribe further procedures such as mammography.

The effectiveness of manual clinical breast examination depends on several factors including the individual physician's proficiency, the duration of the examination, and the weight and age of the patient.

SUMMARY

This invention concerns performing clinical tissue examination with a device that includes a plurality of sensors which produce signals in response to pressure imposed on the sensors as the sensors are pressed against the tissue.

In one aspect, a plurality of sensors generate signals in response to pressure imposed on them when pressed against a selected region of tissue. That pressure varies in accordance with properties of underlying tissue structures. An image of the region of tissue is generated based on the signals generated by the sensors. The image is then displayed. The image represents the pressure imposed on the sensors. The signals produced by the sensors are also processed to detect an underlying tissue structure in the region of tissue.

In another aspect, a plurality of sensors generate signals in response to pressure imposed thereon when pressed against a selected region of tissue. That pressure varies in accordance with properties of underlying tissue structures. The signals produced by the sensors are processed to detect an underlying tissue structure in the region of tissue. A location of the detected underlying tissue structure relative to a reference point is also determined.

In yet another aspect, a plurality of sensors generate signals in response to pressure imposed thereon when pressed against a selected region of tissue. That pressure varies in accordance with properties of underlying tissue structures. The signals generated by the sensors to are processed to generate data representative of a three dimensional image of the region of tissue. That image is then displayed. The three dimensional image represents the pressure imposed on the sensors, based on the signals generated by the sensors.

In yet another respect, a method is provided for performing a clinical breast examination using a tissue examination device. The tissue examination device includes a plurality of sensors, a processor, and a display. A plurality of sensors generate signals in response to pressure imposed on them when pressed against a selected region of tissue. That pressure varies in accordance with properties of underlying tissue structures. The processor then processes the signals generated by the sensors to generate data representative of an image of the region of tissue where the image represents the pressure imposed on the sensors, based on the signals generated by the sensors. The display displays the image. A displayed shape in the image is then examined to identify a selected type of underlying tissue structures.

Preferred embodiments may include one or more of the following features.

The displayed image includes a 3-dimensional image, where one dimension represents a pressure value of the sensors. The displayed image is a top view or a perspective view, or both, of a three dimensional image. The image is displayed with a pre-selected range of colors that correspond to the pressure, a value corresponding to a peak pressure value in the image, and a gradient of a portion of the image. The displayed image includes a shape representative of an underlying tissue structure in the region. Furthermore, an underlying tissue structure is detected and an outline of the shape of the structure is then displayed.

A detected underlying tissue structure is discriminated as one of a plurality of different types of underlying tissue structures. The detected tissue structure is discriminated based on its characteristics including a manner of movement of the detected underlying structure as the plurality of sensor are moved over the tissue, an edge profile, a relative stiffness, and a relative curvature of the detected tissue structure. As part of the discrimination, a degree of membership of the detected tissue structure in a preselected class of tissue structures corresponding to the discriminated type is determined.

A location of a detected or discriminated tissue structure is determined. One or a plurality record is then stored in a database, where the record includes a characteristic corresponding to the detected tissue structure and the location of the detected tissue structure. The stored characteristic includes size, manner of movement of the detected underlying structure as the plurality of sensor is moved over the tissue, an edge profile, a relative stiffness, and a relative curvature of the detected tissue structure. The processor may discriminate the detected underlying tissue structure as one of a plurality of different types of underlying tissue structures. A result of the above discriminating is then stored in the record.

The determined location is processed to produce a map of the location of a detected tissue structure. The map is then displayed. The displayed map has a characteristic of a group of the signals corresponding to the detected tissue structure displayed in relation to the location of the detected tissue structure. Those displayed characteristic include size, edge profile, relative stiffness, relative curvature of the detected tissue structure, and a manner of movement of the detected underlying structure as the sensors are moved over the tissue. The map may also include displayed results of discriminating a detected underlying tissue structure as one of a number of different types of underlying tissue structures in relation to the detected tissue structure.

The reference point relative to which the location of the detected underlying tissue structure is determined is a point on a body being examined.

Data representing a previous tissue examination is retrieved. The data was previously stored during the previous examination. The data may be values representative of signals generated by the sensors during a previous examination or a result of processing signals in the previous tissue examination to discriminate an underlying tissue structure as one of a plurality of different types of underlying tissue structures. The data may also be a location of a detected tissue structure in the previous tissue examination relative to the reference point or a degree of membership of a detected tissue in the previous tissue examination in a preselected class of tissue structures.

The retrieved data is processed to generate a first map of a location of a tissue structure detected based on the previously stored data. The map is generated relative to the same reference point as the current examination. This map is then displayed with a map of the current examination.

The retrieved data is processed to discriminate a second underlying tissue structure in the region of the tissue as one of a plurality of different types of underlying tissue structures. Then, it is determined whether that tissue structure is the same as the one detected in the current examination. If so, the values corresponding to them are compared to determine changes in the underlying tissue structure between the previous and current examinations.

Examining a displayed shape to identify a selected type of tissue structures includes attempting to identify a characteristic of the shape, where the characteristic suggests a degree of membership of an underlying tissue structure in a class of tissue structures. Examining the displayed shape includes identifying a discrete, dominant, or different characteristic in the shape. The class of tissue structures is selected among a group including carcinoma, ribs, cysts, inframammary ridges, hard lumps, and soft lumps.

The examined characteristics of the image include:

size of the shape;

height of the shape's various areas;

flatness of the shape;

peakedness of the shape;

whether the shape has a plateau;

outline of the shape;

contour of the shape;

a gradient along any part of the shape;

movement of the shape in response to moving the sensors over the tissue; and change in the shape in response to changing the imposed pressure.

The shape is examined to identify a carcinoma by identifying a characteristic selected among a plurality of carcinoma characteristics including:

peaked shape, low gradient between edges and a peak of the displayed shape, relative to other shapes, small movement of the shape in response to moving of the sensors over the tissue, relative to the other shapes, small change in the shape in response to changing the imposed pressure, relative to the other shapes, and growth of the shape over time.

Generally, any image, map, or other output may be a printer for printing or a visual display for displaying.

Advantages of the invention may include one or more of the following advantages.

The device has the ability to translate pressure readings from a sensor or sensors pressed against the tissue to a series of visual images of those pressure readings. Translating the pressure readings into images allows a clinician to identify an underlying tissue structure by analyzing characteristics which may suggest a selected foreign structure, such as a carcinoma.

The device can show at the same time the edge transition, the extent and the three dimensional character of the underlying tissue structure.

When operating in expert mode, little training is required to use the tissue examination device. In this mode, the device quantifies the physical characteristics of the underlying structure. These characteristics include size, edge profile, relative stiffness, relative curvature of the detected tissue structure, and a manner of movement of the detected underlying structure as the plurality of sensor is moved over the tissue. The tissue examination device can also provide a database and a map of the relative location of suspicious structure. Quantifying the characteristics and providing a map enable clinicians to easily communicate with each other with respect to a particular lump in a way that is not based on subjective observations. They also allow the clinician to record the characteristics so as to track developments over time.

The tissue examination device also has the ability to store and review data representing a test, which allows reconstructing a previous examination. Therefore, the tissue examination device can automatically track a lump over time. The device is also capable of storing the raw data from a test so that future improvements in analyzing the data can be used to improve the results of a current diagnosis.

The device can be used to supplement other methods of tissue examination. The device can be used to identify areas which should be further examined by using manual palpations, mammography, biopsy or other procedures.

Embodiments of the device can be readily and inexpensively produced using readily available components. Therefore, the device can be used by clinicians in regular office examination to further the goal of early detection.

The tissue examination device allows examining a large tissue quickly.

Other advantages and features will become apparent from the following description and from the claims

DRAWINGS

The file of this patent contains at least one drawing executed in color. Copies of this patent with the color drawings will be provided by the Patent and Trademark Office upon request and payment of the necessary fee.

Figure 1:
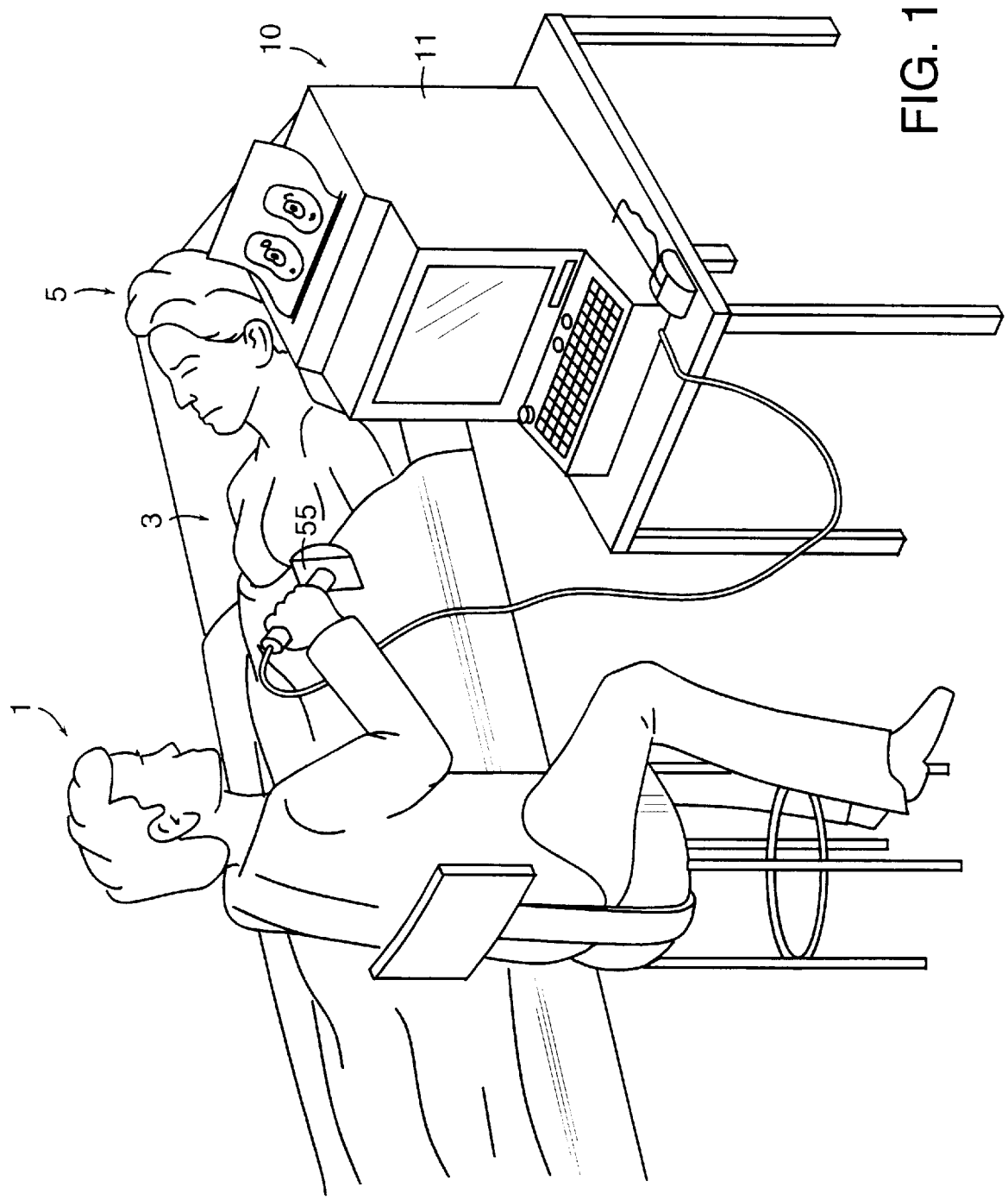
FIG. 1 shows a clinical breast examination using a clinical tissue examination device.
Figure 13B:
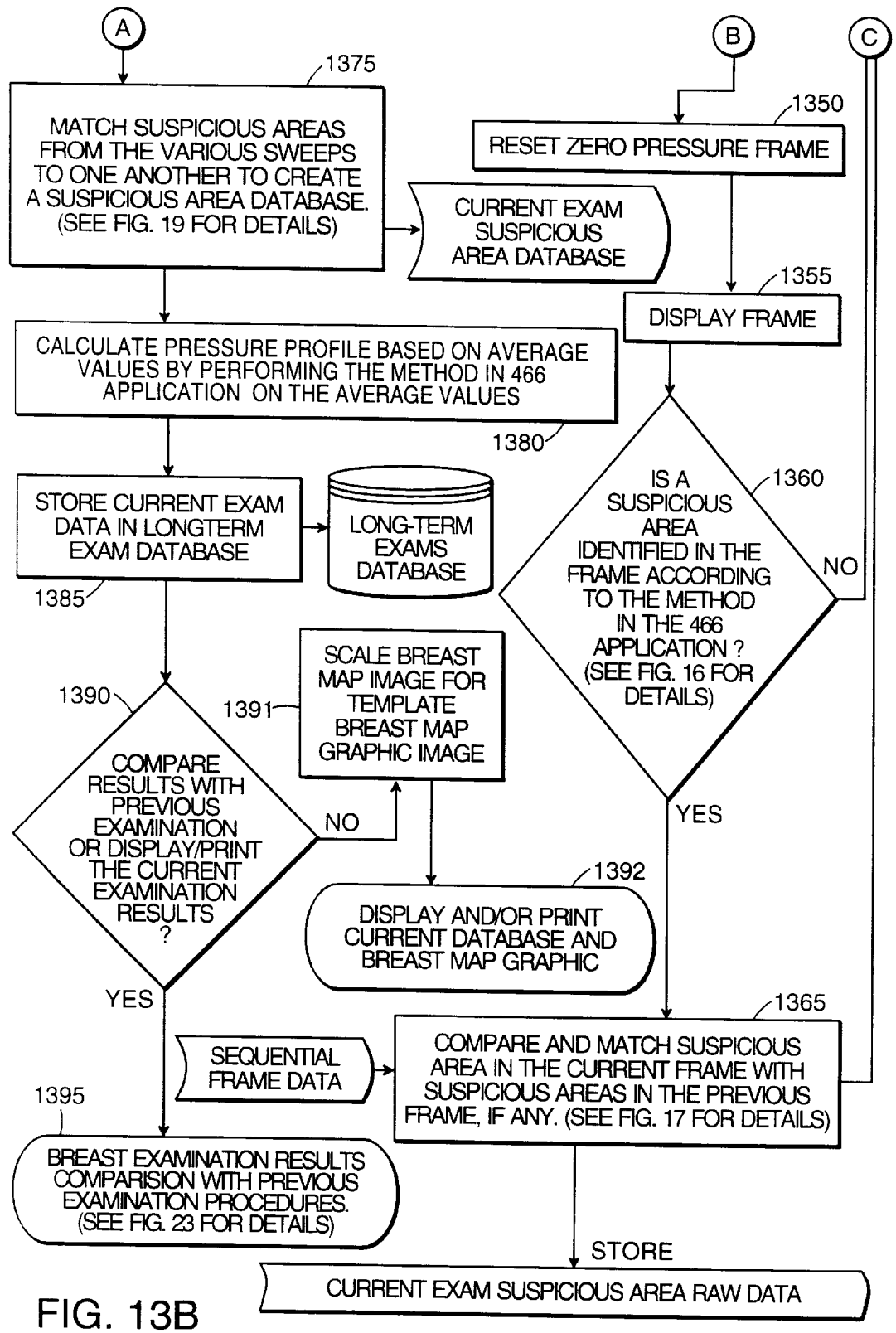
FIG. 13 shows the inter-relationship between FIGS. 13A and 13B.

FIGS. 13A and 13B, in combination, are a flow chart of the operation of the tissue examination device of FIG. 1 in the second mode of operation.

Figure 14:
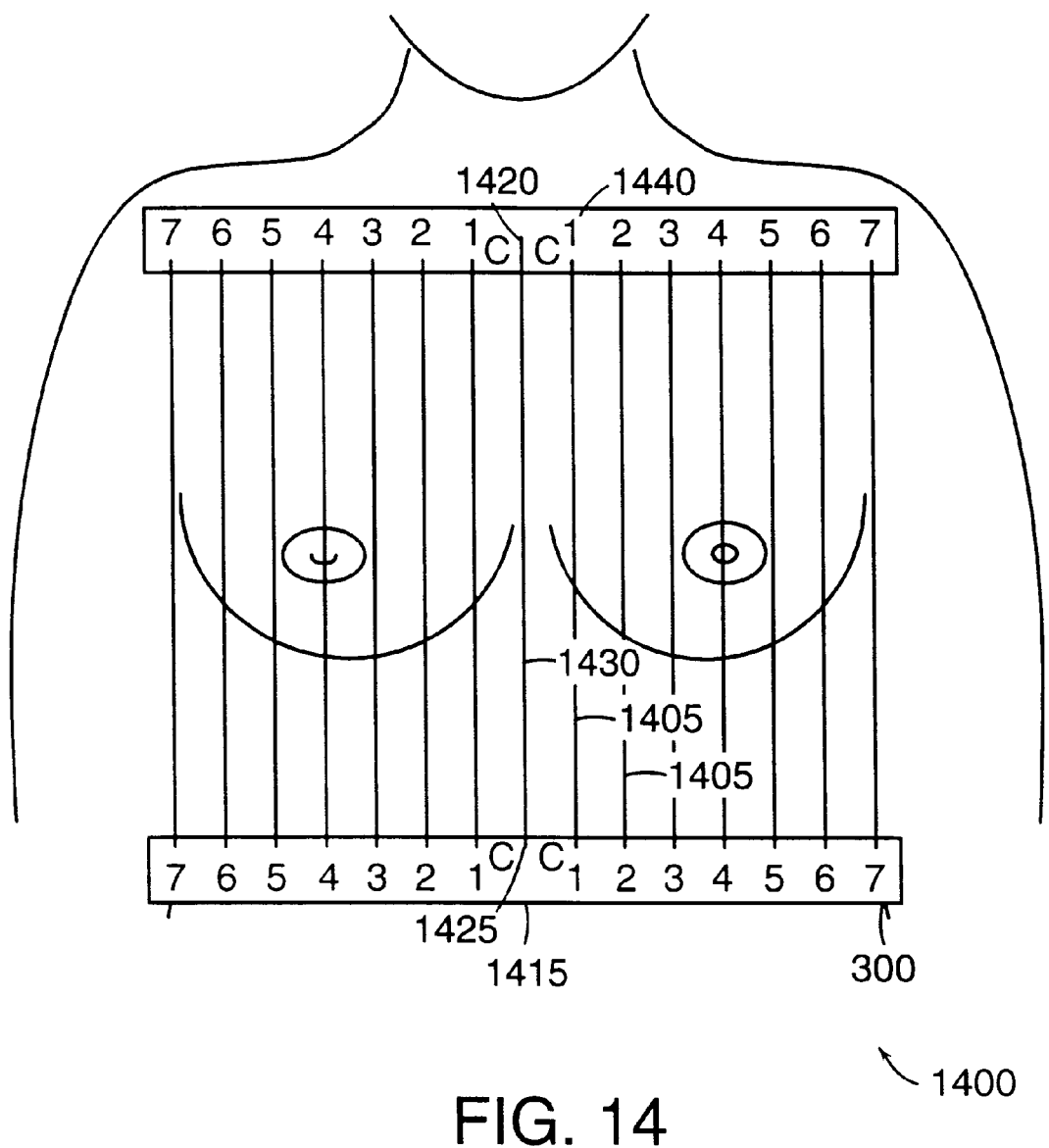

FIG. 14 shows a polyurethane sheet which is used in a clinical breast examination.

Figure 15:
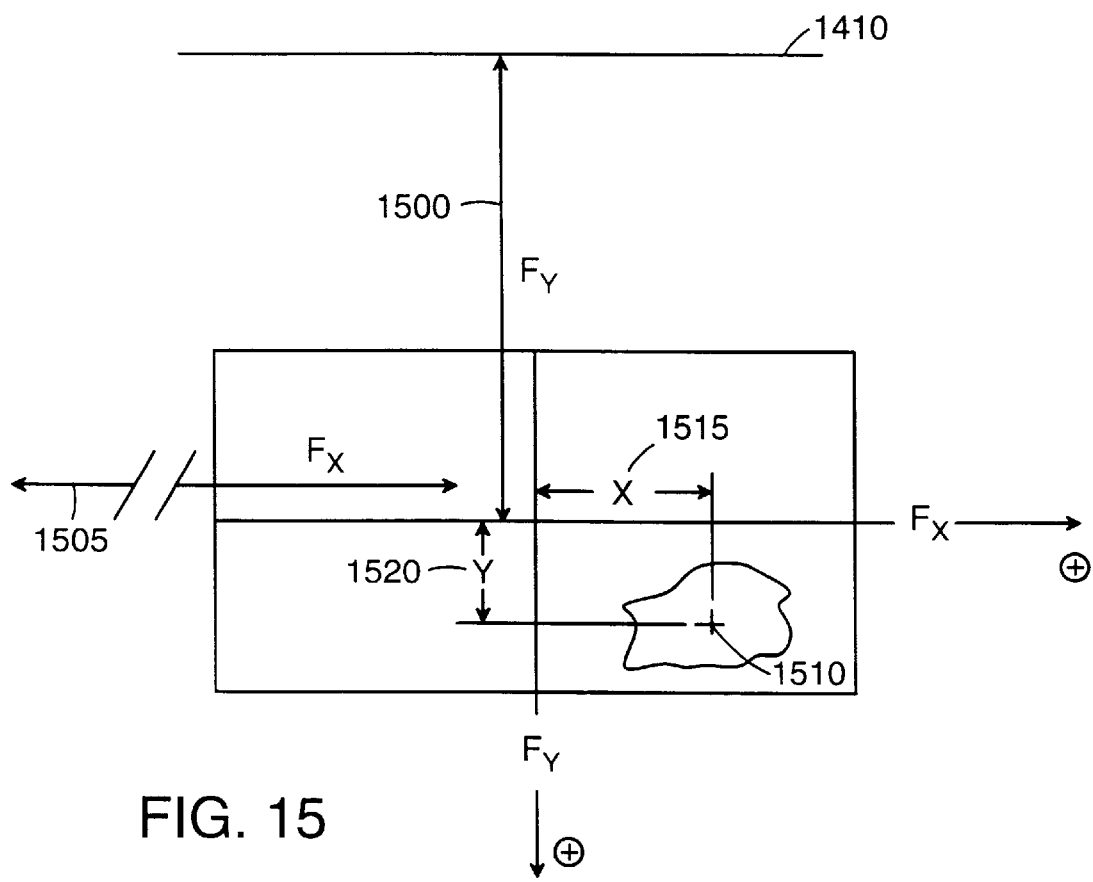

FIG. 15 shows a sensor in a frame of signals and its coordinate values.

Figure 16:
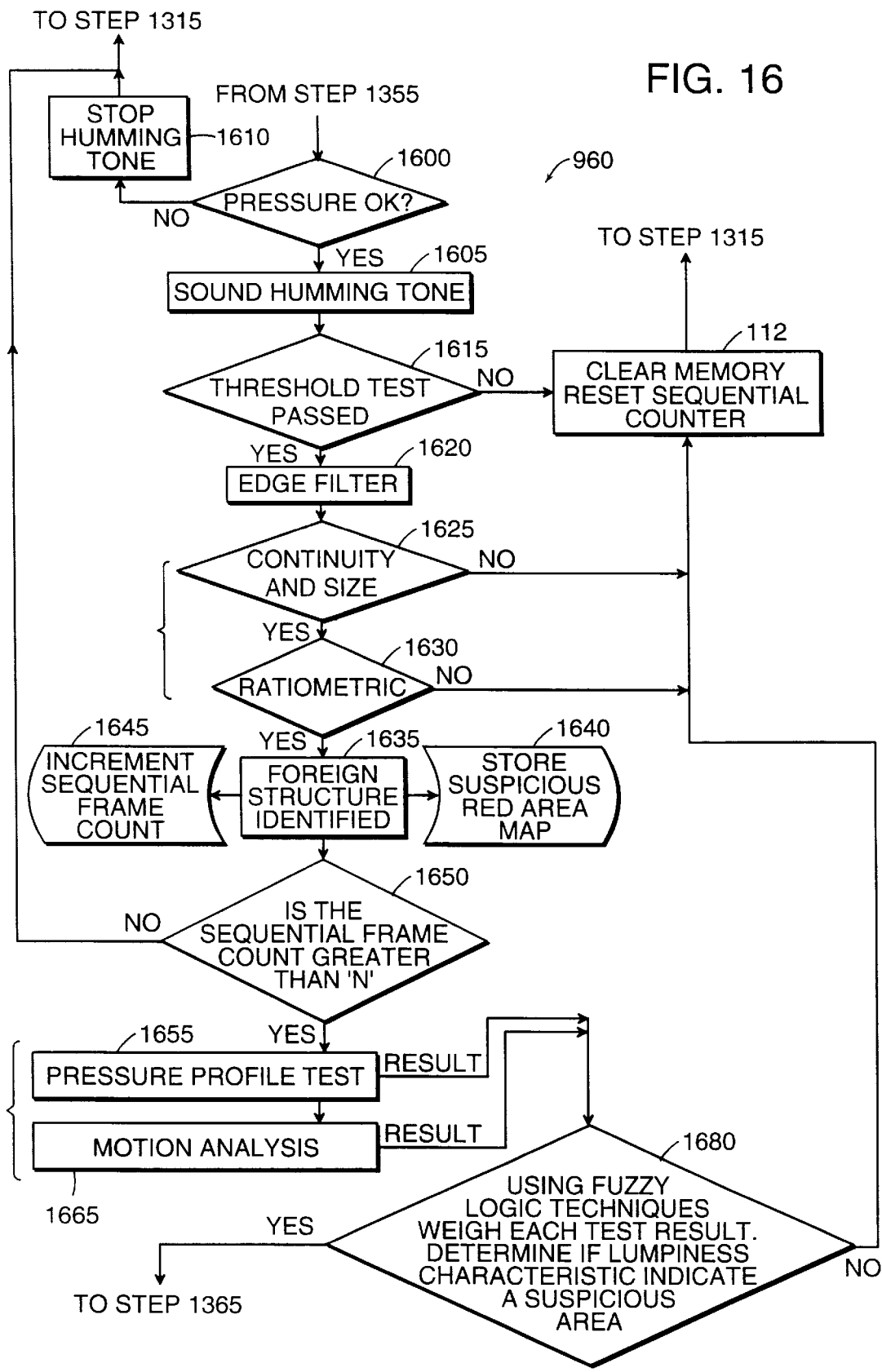

FIG. 16 is a flow chart of the procedure for identifying suspicious areas by a tissue examination device.

Figure 17:
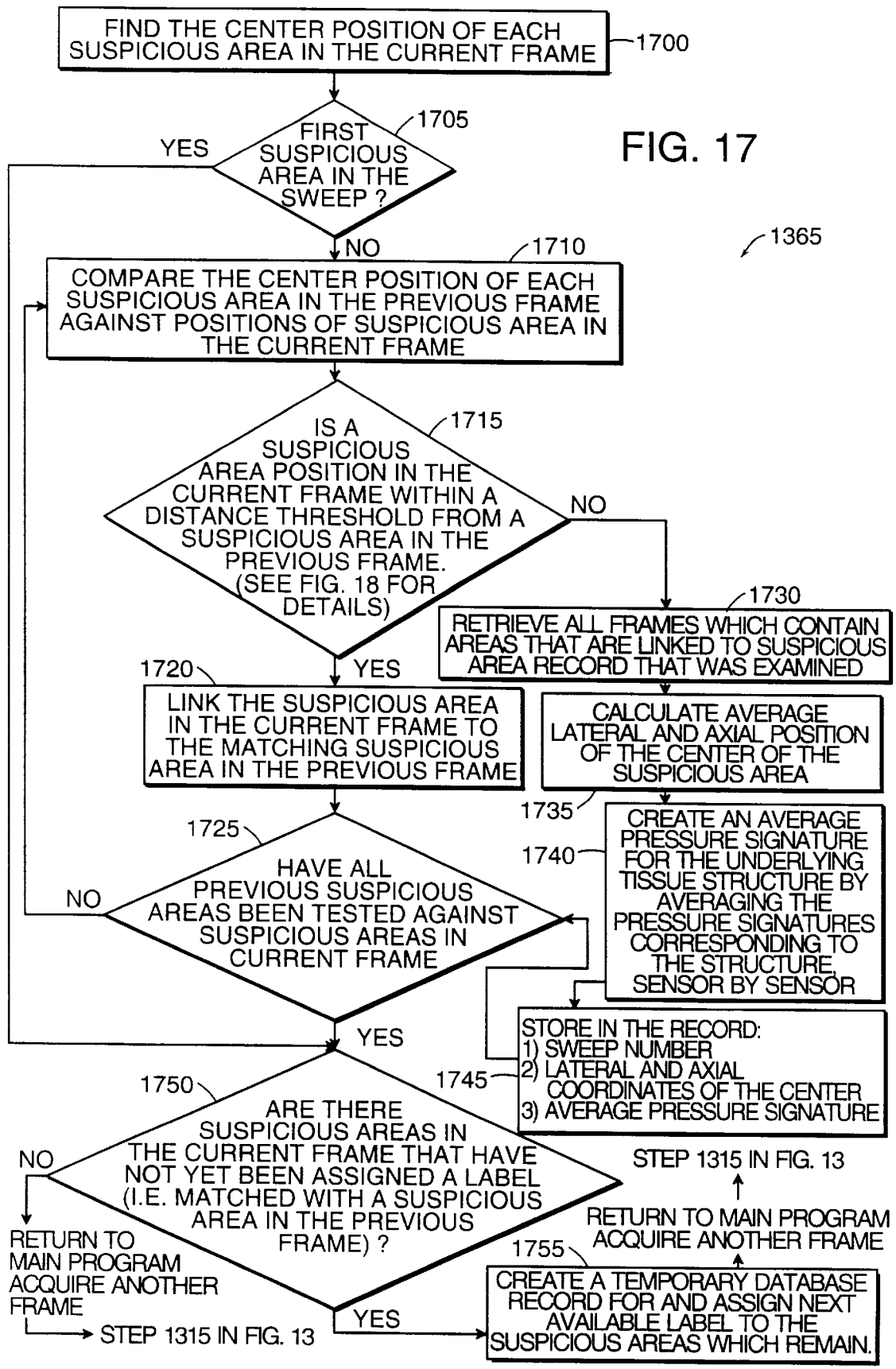

FIG. 17 is a flow chart of the procedure of identifying and matching of suspicious areas in two frames from one sweep.

Figure 18:
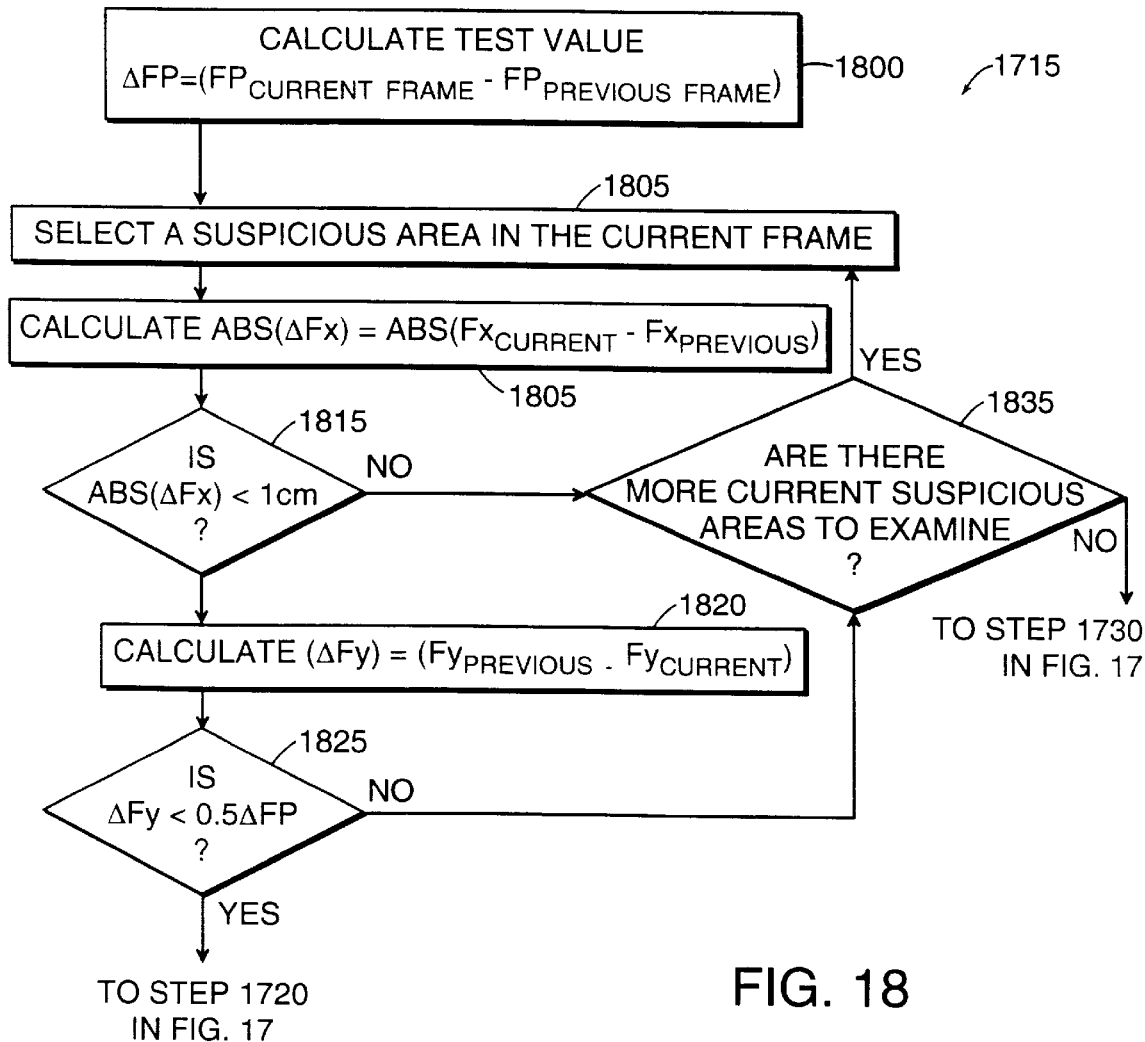

FIG. 18 is a flow chart of the procedure for determining whether a suspicious area in two frames are of the same underlying structure.

Figure 19:
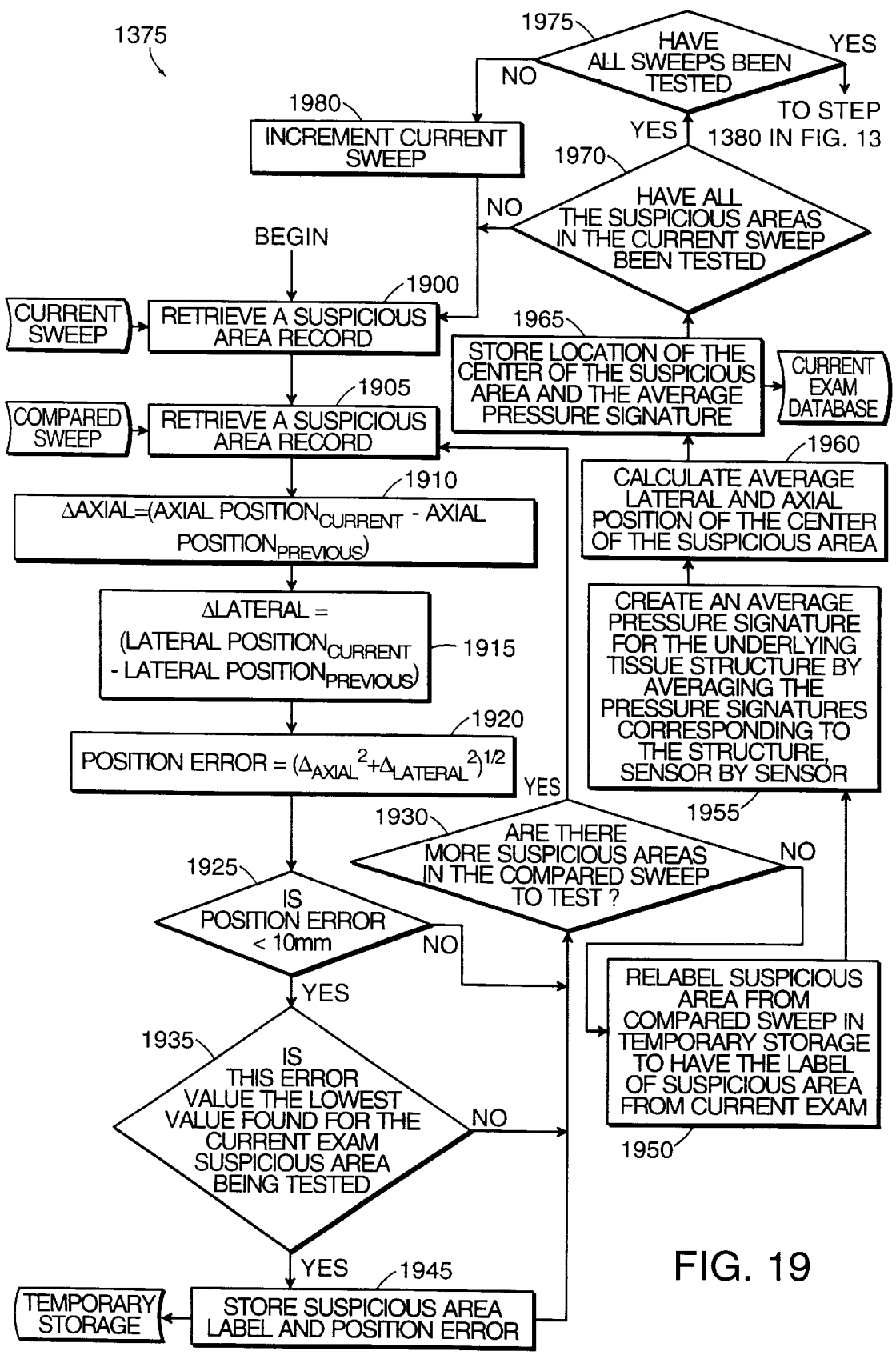

FIG. 19 is a flow chart of the procedure for creating a suspicious area database.

FIG. 20 shows the suspicious area database record structure.

Figure 21:
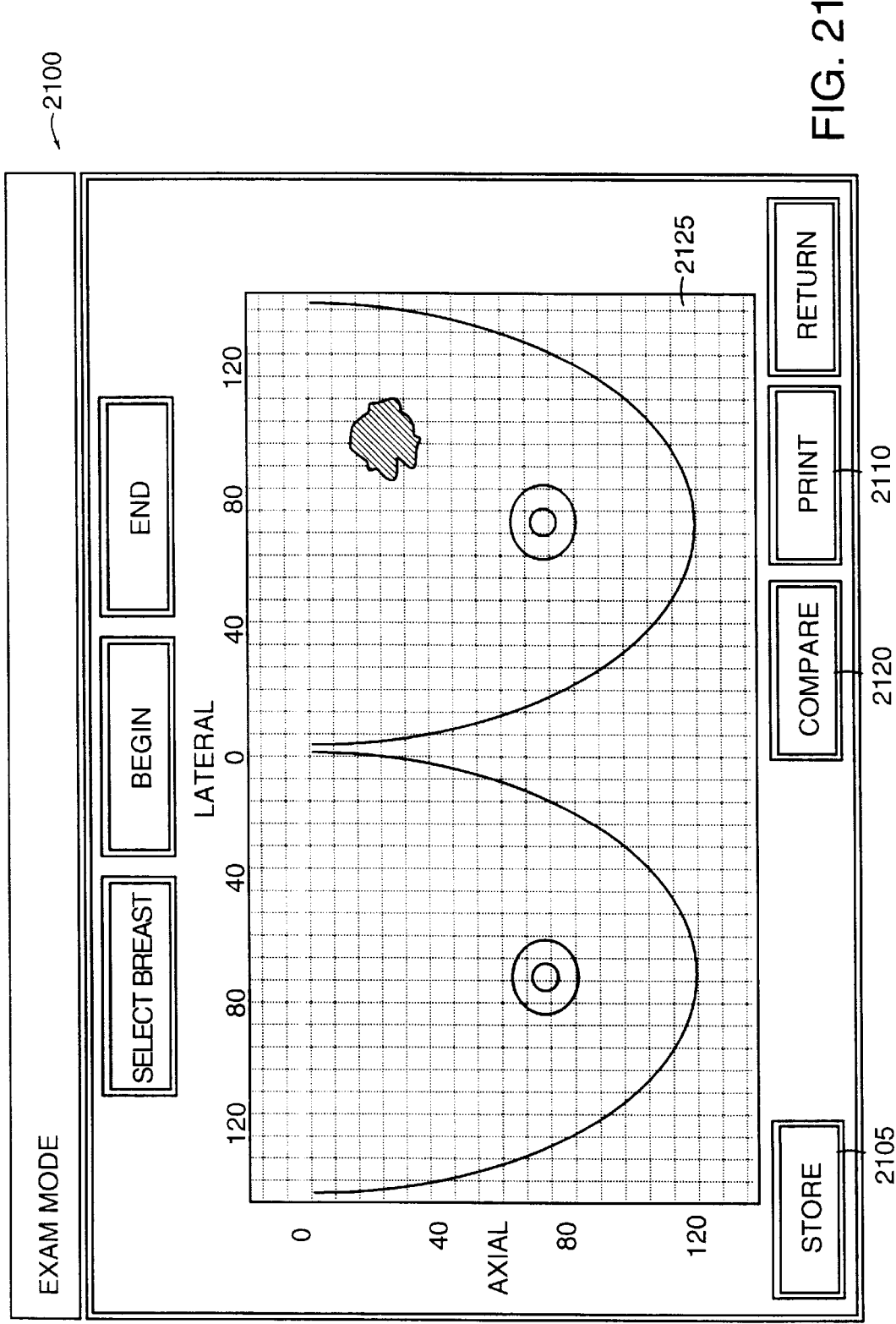

FIG. 21 shows the graphical user interface of a tissue examination device displaying a suspicious area map.

Figure 22:
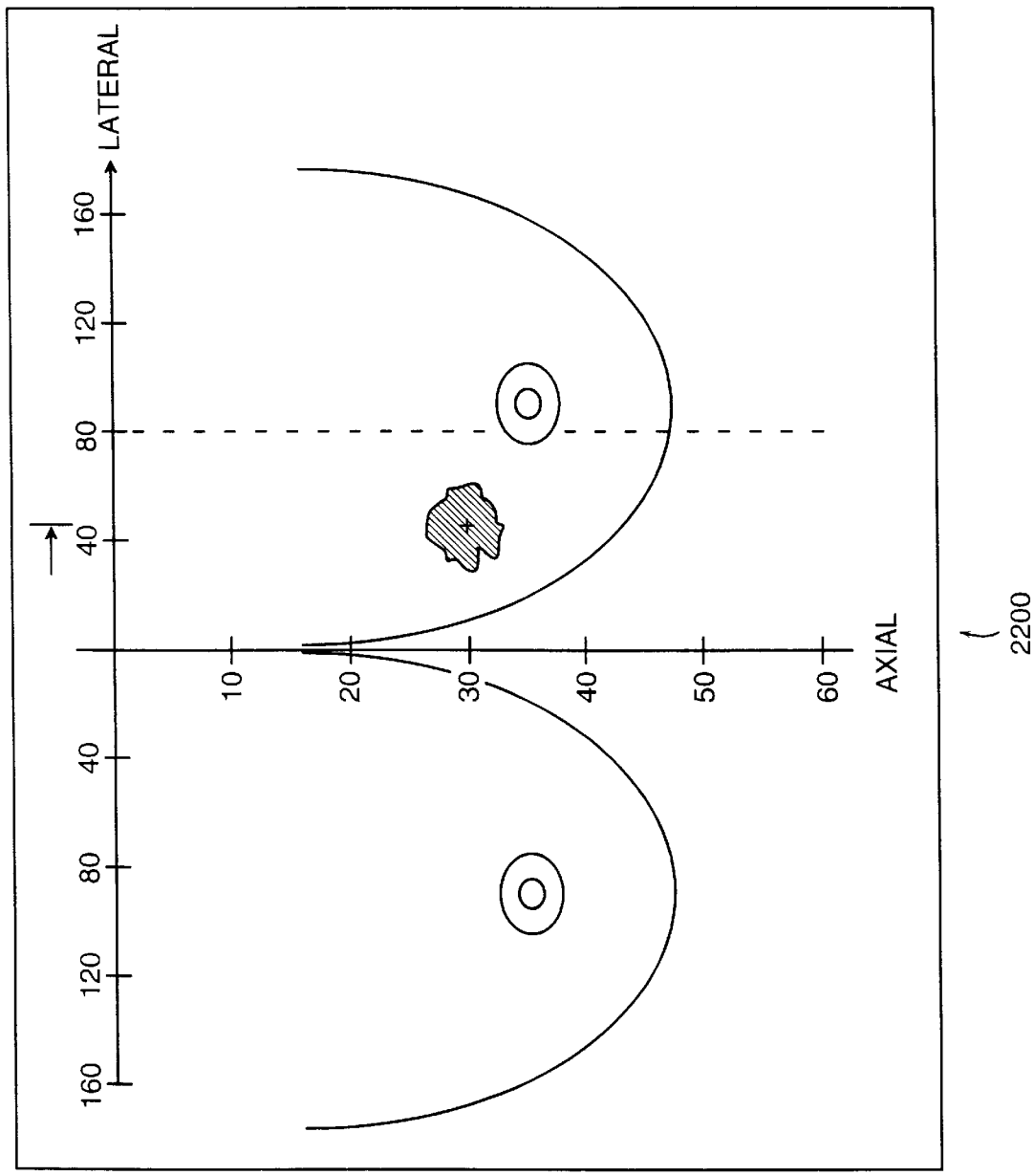

FIG. 22 shows a print out of a suspicious area map.

Figure 23:
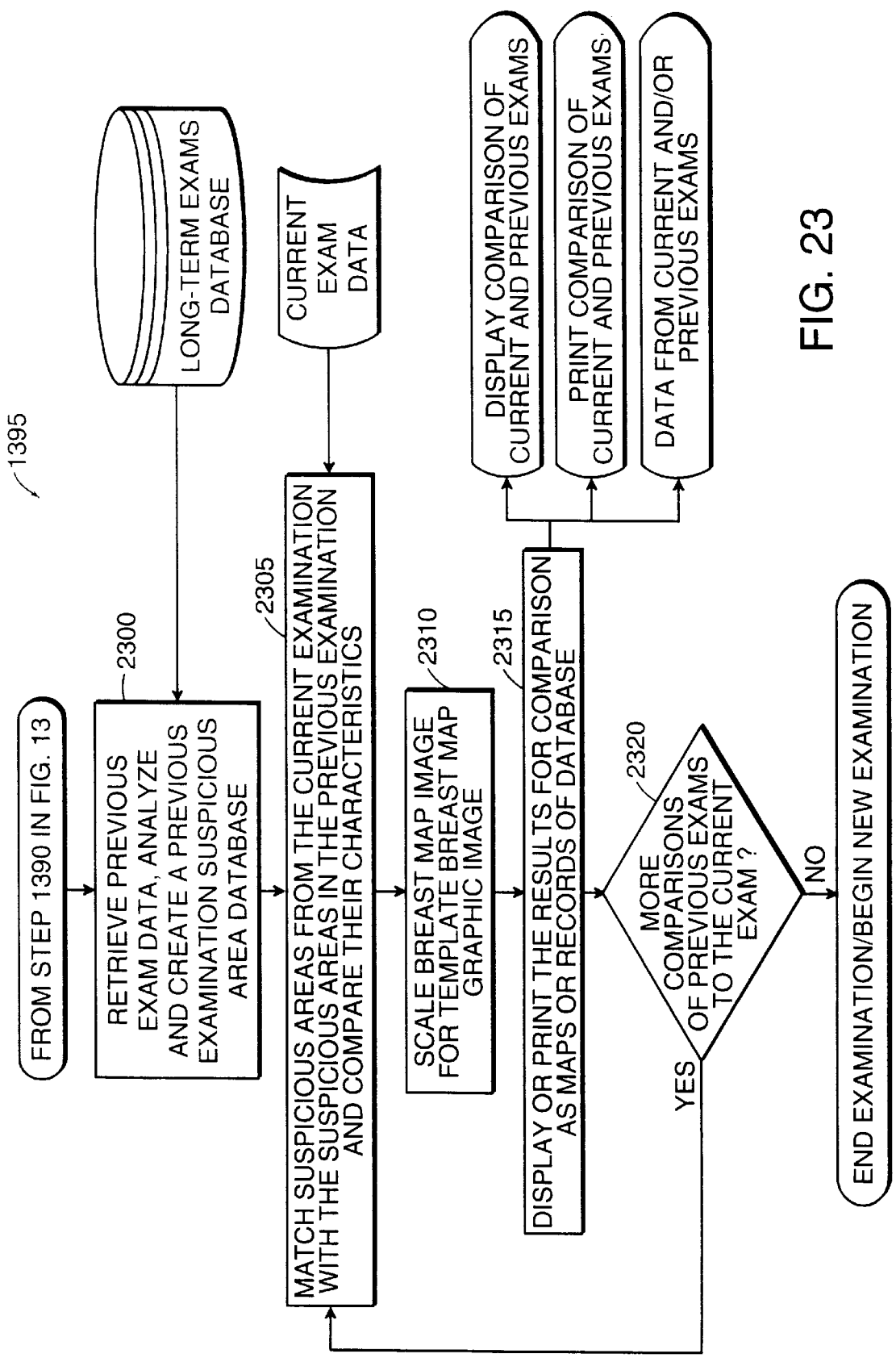

FIG. 23 is a flow chart of a procedure of comparing results of current examination and previous examination.

Figure 24:
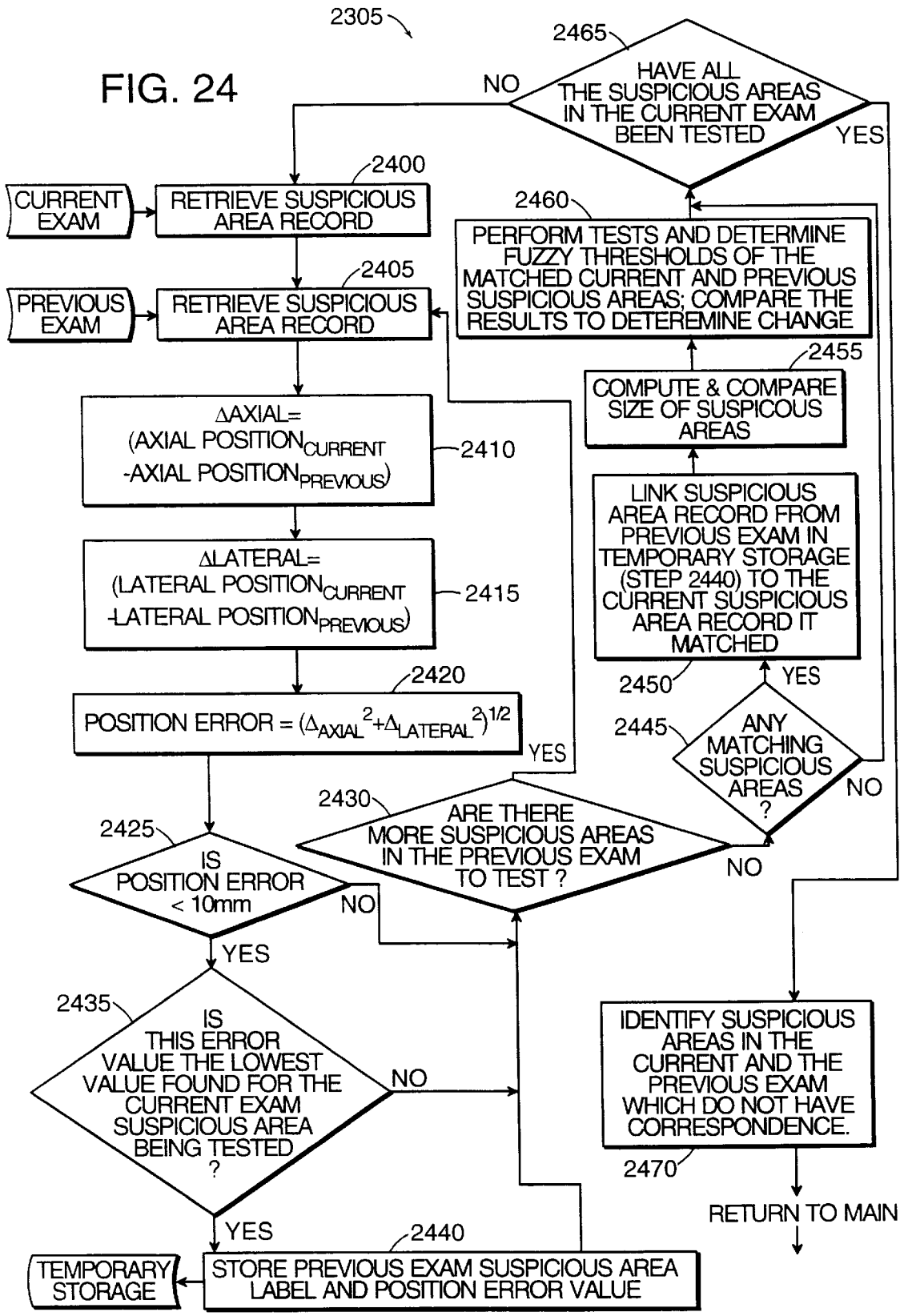

FIG. 24 is a flow chart of a procedure for determining correspondence between suspicious areas found in two different clinical examinations.

Figure 25:
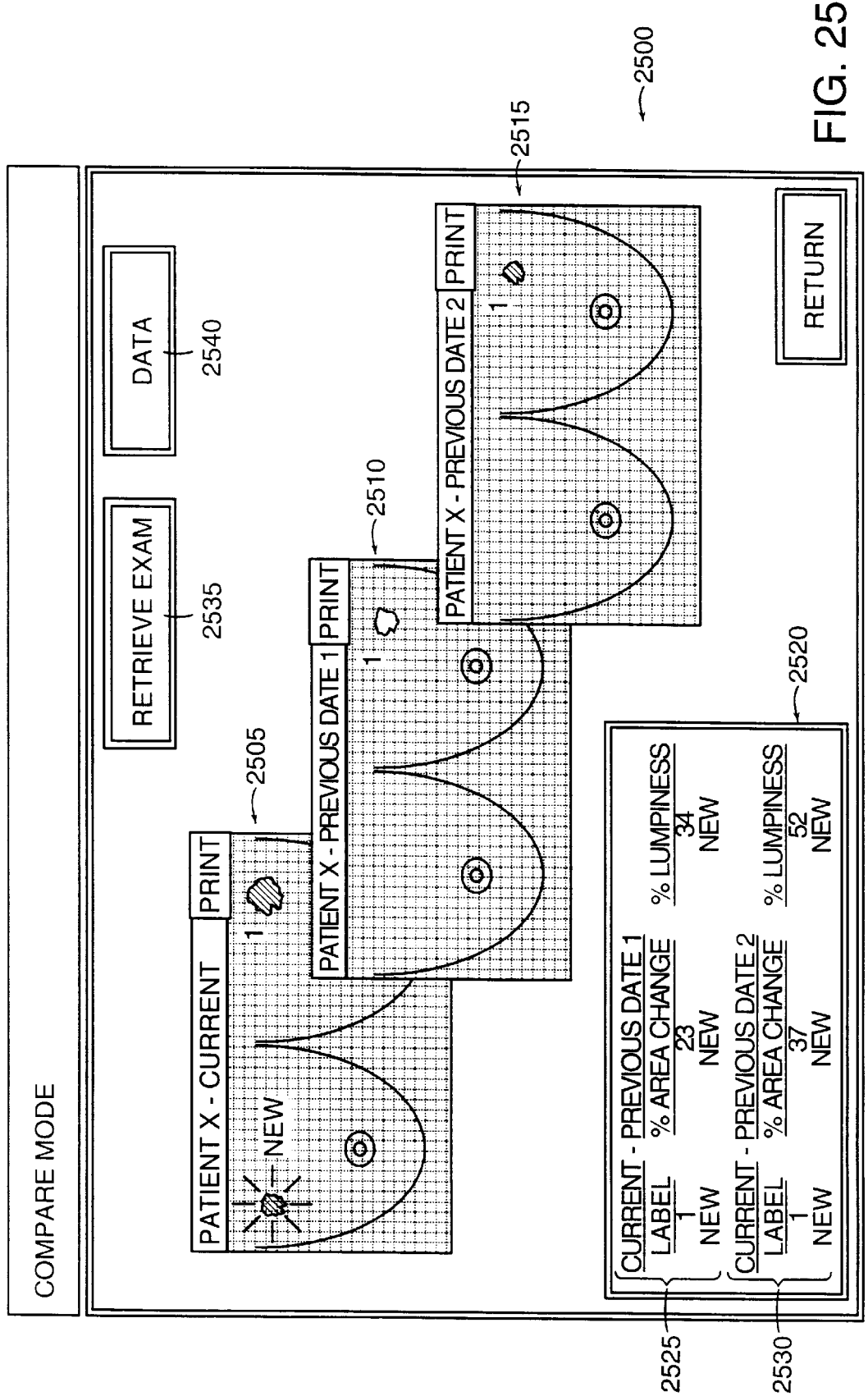

FIG. 25 shows the graphical user interface of a tissue examination device displaying results of comparing a current examination and a previous examination.

Figure 26:
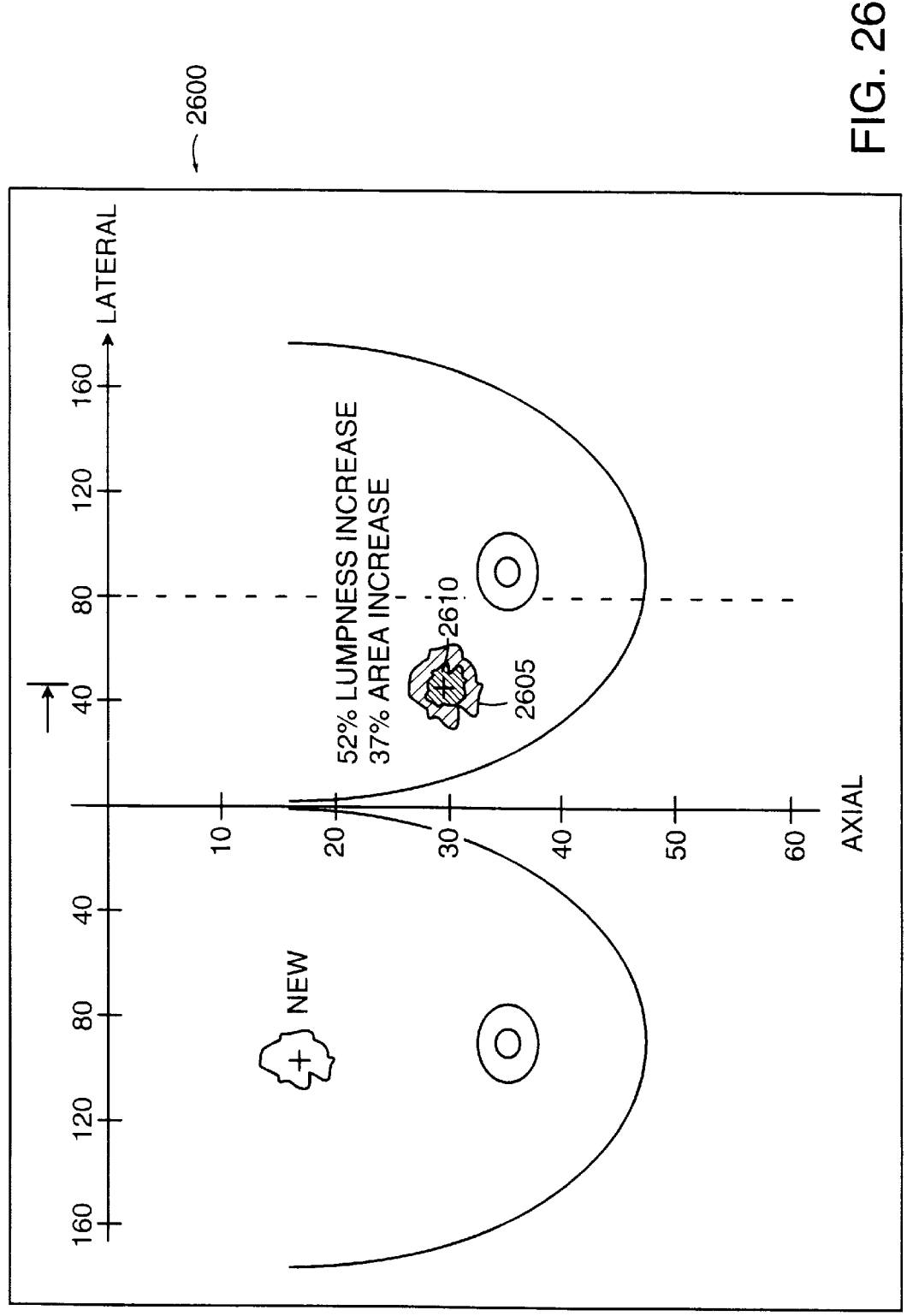

FIG. 26 shows a print out of results of comparing a current examination and a previous examination.

DESCRIPTION

Prior to describing in detail an embodiment of a tissue examination device 10 in FIG. 1 and its operation, we will first generally describe how a clinician uses the tissue examination device during a clinical exam and how the tissue examination device assists the clinician during that exam to diagnose.

Referring to FIG. 1, a clinician 1 examines breast tissue 3 of a patient 5 by translating across the breast tissue an array of pressure sensors 12 (shown on FIGS. 2 and 3) installed on a sensor head 55 of tissue examination device 10. Tissue examination device 10 also includes a computer console 11 that provides the main user interface between the clinician and the device. Tissue examination device 10 obtains signals from the array of sensors and processes them (a set of sequentially produced output signals for all of the pressure sensors in the array is termed a "frame," as will be described more fully below). These signals generally correspond to the pressure with which the tissue "pushes back" against the sensor head. The processing of these signals achieves a variety of functions, as will be described below in reference to two modes of operations of the device.

Briefly, the two modes of operation of tissue examination device 10 are a non-expert and an expert mode, respectively. The clinician during these modes of operations can use the device in a variety of ways to assist him or her with examining the tissue and determining whether any foreign structure, such as carcinoma, is present in the tissue.

Figure 6:
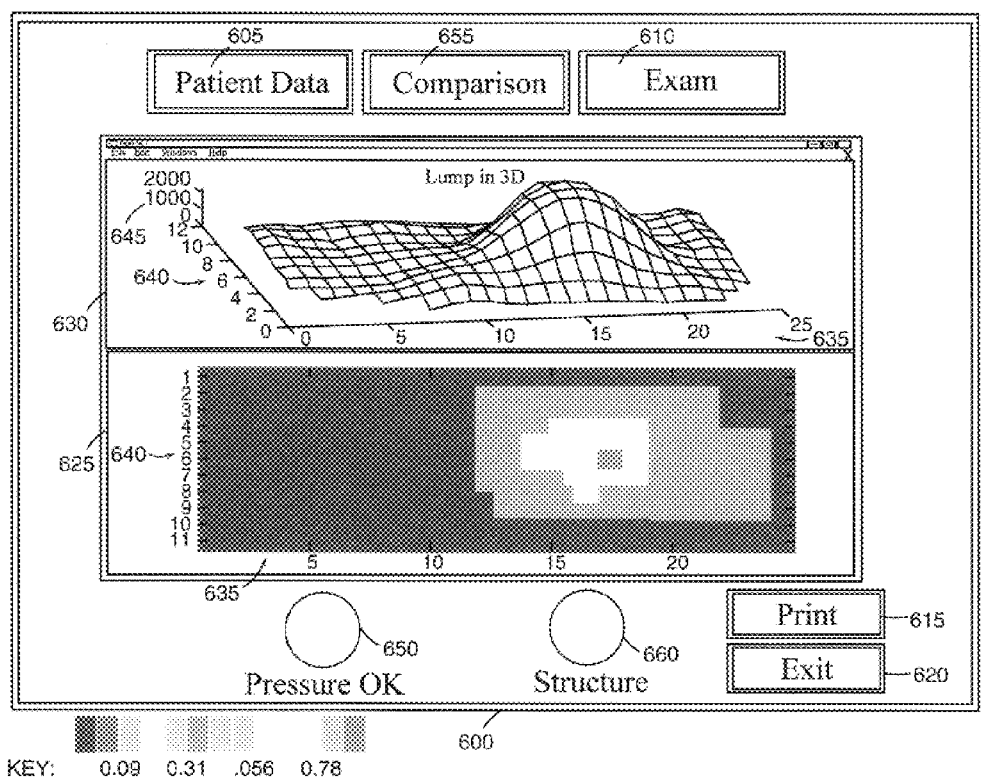
FIG. 6 shows the graphical user interface of a tissue examination device.

Generally, in the first mode of operation which is the non-expert mode, console 11 displays a user interface that includes a display of a 3 dimensional image of the pressure signatures of the tissue underlying sensor head 55. The user interface and the image are shown in FIG. 6, which will be described in detail below. The displayed three dimensional image is a graphical representation of the pressure readings from the array of sensors. The first and second axes of the image represent the location of the sensors in the array, while the third dimension represents the pressure readings of the sensors. In this image, the pressure signatures of the various underlying tissue structures appear to have various shapes whose characteristics are based on the type of underlying tissue structure. Therefore, clinician 1 can readily identify the underlying tissue structure by analyzing these shapes and their characteristics. The image may further be enhanced in a variety of ways, including using various color scales to show the various ranges of pressure values (e.g. FIGS. 7A–12B), and showing top and perspective views of the 3-D image to better show the outline of the shape of the underlying tissue structure.

In the second mode of operation which is the expert mode of operation, tissue examination device 10 performs further functions which assist the clinician in diagnosing and which augment that diagnosis. Tissue examination device, generally, performs a variety of tests which are designed to detect and discriminate areas in individual frames that indicate a suspicious structure in the tissue underlying the array (hereinafter referred to as "suspicious areas").

The tissue examination device can also provide a map showing the location of such suspicious areas, if any, relative to a reference point (e.g. a point on the body). In some embodiments, in order for the tissue examination device to determine the location of the suspicious areas relative to the reference point, the clinician follows a specific method for conducting exam, described below in detail. The method is designed to provide device 10 with information that could be used in determining the location of the identified structures.

Briefly, according to this method, the clinician is provided with a template to guide him in translating the sensor head. The template is a polyurethane sheet having a number of lines extending axially. The polyurethane sheet is attached to the upper part of the patient's torso by the clinician according to a method that is designed to ensure that there is little variation in the position of the sheet from examination to examination.

After attaching the sheet, the clinician translates sensor head 55 along the axial lines in a predetermined pattern, e.g starting at left most axial line, translating from top to bottom, and then proceeding to the adjacent line to the right (we will refer to each translation along an axial line as a "sweep," as will be described in detail below). The sensor head provides the tissue examination device with signals from a motion sensor indicating the position of sensor head 55 in the sweep. The sensor head also indicates to the device when a sweep is finished. Using these inputs, the tissue examination device determines the location of the suspicious areas in the examined tissue, as will be described in detail below In some embodiments, as the clinician carries out the examination according to the above method, the tissue examination device also provides the clinician with a display of the pressure signature, as in the first mode.

Once the clinician completes examining both breasts, the tissue examination device generates a database that has records regarding the suspicious areas (FIG. 20 shows an example of the record structure of such a database). These records may contain data regarding the location, characteristics, expert system estimation or discrimination of the type of structure represented by a suspicious area, and so on. The database may also contain the raw sensor signals. Such a database may be later used for referring to the results of the examination. The clinician may use the data in this database to, for example, review the results of the exam at a later date or to discuss the results with colleagues. The database may also be used to reanalyze the data based on improvements in technology.

The tissue examination device also produces a map of the location of the suspicious areas. The clinician can view this map on the console (an example of such a display is shown in FIG. 21) or print the map (an example of such a printout is shown in FIG. 22).

In the second mode of operation, the clinician also has the option of selecting to compare the results of a current examination with the results of a previous examination. In such a case, the tissue examination device retrieves the database containing data relating to a selected previous examination. The tissue examination device then processes that data, including matching data from the two examination, where both data represent the same suspicious area. The tissue examination device may also compare the data from the current examination with that of a previous examination to detect changes in underlying structures. Such changes may include growth or reduction in size of a suspicious area, appearance or disappearance of an area, increase in the likelihood the area representing cancerous tissue, and so on. In this way, a clinician can track the developments in a patient's breast over a period of time.

The clinician can access and view the data in a variety of ways. The clinician can for example view the results of the comparison in the form of super imposed maps or concurrently displayed maps. The clinician can also view the system's estimation of the meaning of these changes (e.g 23% larger, and 34% more likely that it is a carcinoma, than in the previous exam). An example of a visual display of such comparison results on console 11 is shown in FIG. 25 and an example of a printout of the results is shown in FIG. 26.

Prior to describing the two modes of operation of tissue examination device 10, which we briefly discussed above, we will first describe the structure of the tissue of the tissue examination device. First, we will describe the structure in terms from the point of view of a clinician using the device, namely the console and the sensor head. We will then describe the structure as it relates to the operation of the device.

Figure 2:
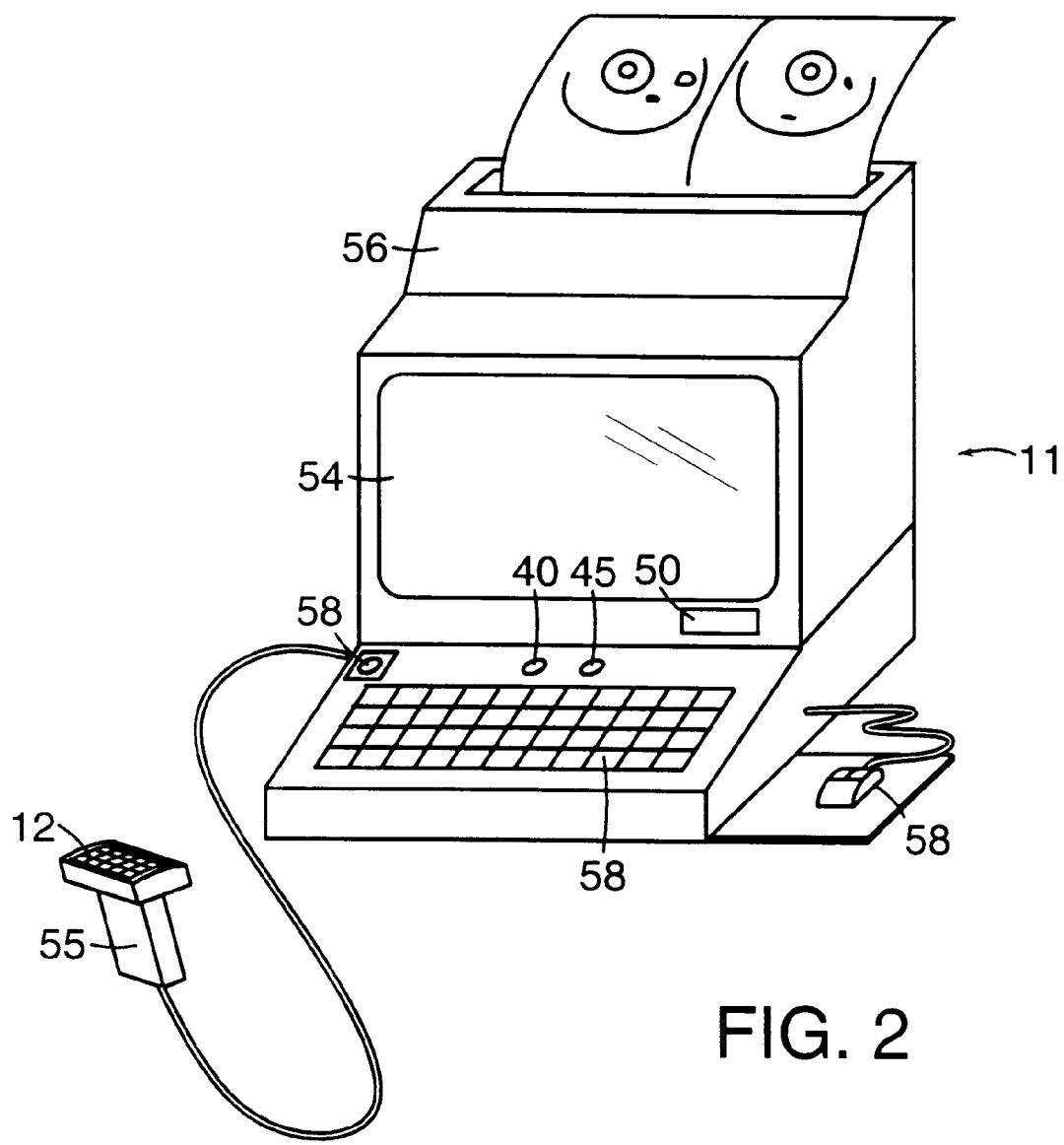
FIG. 2 shows a first embodiment of a clinical tissue examination device.

Referring to FIG. 2, console 11 and sensor head 55 are the main components with which the clinician works with. Console 11 includes a visual display 54, e.g. a CRT tube or LCD screen, which displays a variety of graphical user interfaces (GUIs). These GUIs allow the user to select what function he requires the tissue examination device to perform. These GUIs also include displays of the results of processing the signals from sensor head 55, as will be described in detail below. Console 11 also has a keyboard and trackball/mouse combination 58 for the clinician input, such as patient history or selecting menu items by "clicking"

appropriate spots (so called "buttons") on the GUIs. Console 11 further includes a printer 56 for printing results of clinical examinations including maps of suspicious areas and 3-D images of the pressure signatures of underlying tissue. Console 11 also includes a green LED 45 and a red LED 40, within easy view of the clinician, which are used to notify the clinician regarding a variety of conditions during the examination, as will be explained below. An audio output circuit 50, that includes a speaker, is also located on the circuit to provide audio feedback to the clinician during the operation of the device, as will described below.

Figure 3:
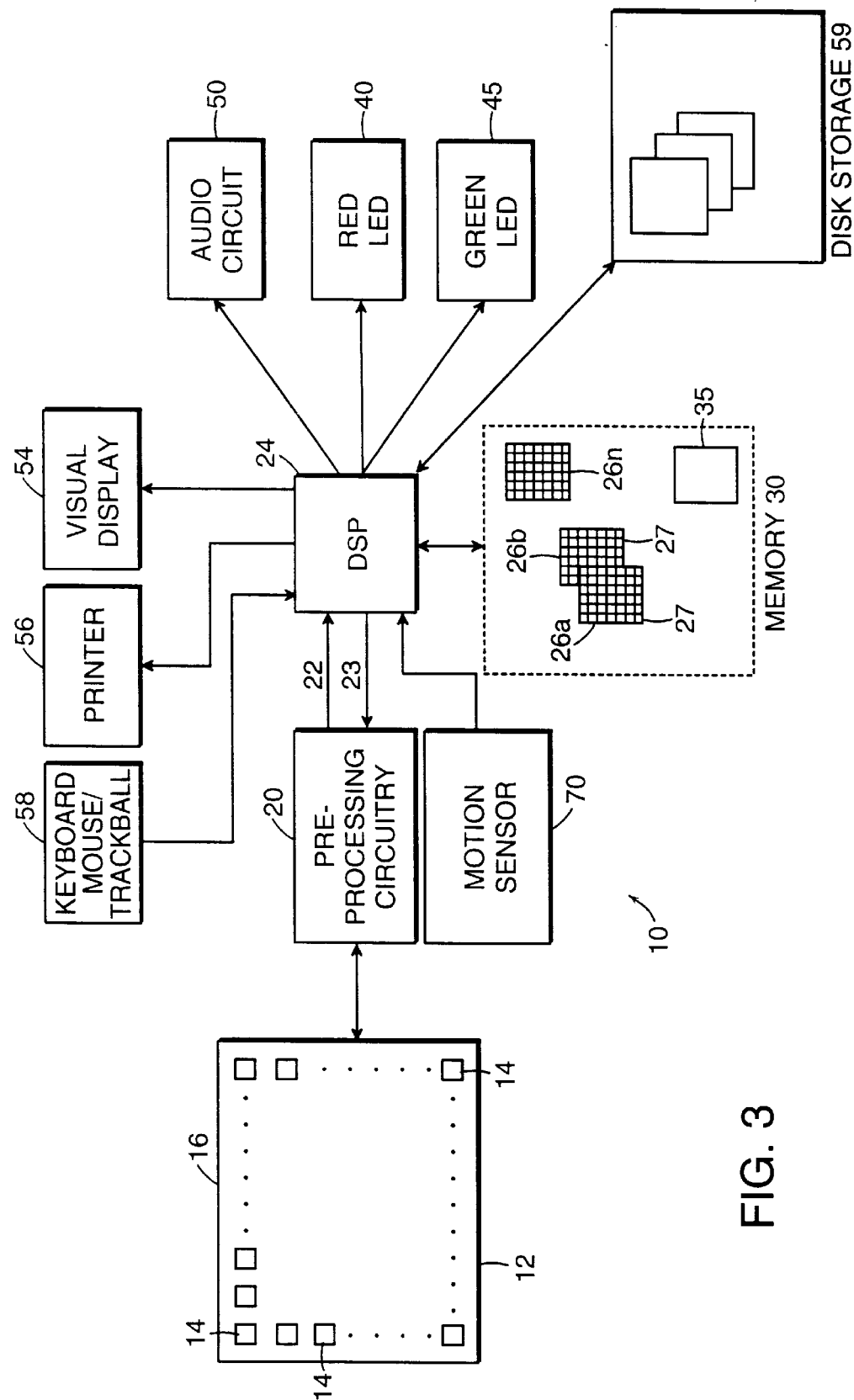
FIG. 3 is a block diagram of a tissue examination device.

Referring to FIG. 3, tissue examination device 10 also includes sensor head 55 which in turn includes an array 12 of pressure sensors 14 carried on a thin, flexible membrane 16. Array 12 is, for example, a contact sensor such as that described in U.S. Pat. No. 4,856,993, entitled "Pressure and Contact Sensor System for Measuring Dental Occlusion" (the '993 patent), incorporated herein by reference, the individual pressure sensors 14 of which are resistive elements. Pressure sensors 14 are arranged in an orthogonal grid of rows and columns in array 12. Pressure sensors 14 are relatively small and are closely spaced to provide high resolution capable of distinguishing between areas of underlying tissue separated by 1 mm or less. Array 12 is commercially available from Tekscan, Inc. (the assignee of the '993 patent).

Array 12 is mounted on sensor head 55 which is made from a rigid polymer such as polycarbonate. (In FIG. 3, array 12 is shown as including twenty sensors 14; it will be understood that the number of sensors 14 in array 12 is typically much larger.) Sensor head 55 is attached to a handle 60 which is grasped by a clinician to place array 12 against the tissue to be examined (such as a patient's breast). The face of sensor head 55 on which array 12 is mounted is convex, with a radius of curvature of approximately 1.5 inches to enhance the mechanical coupling between sensors 14 and the underlying tissue. The optimum range of the array curvature for mechanical coupling between sensors 14 and the underlying tissue is a radius of curvature between 1"–2.51", although a radius as low as 0.5" or as high as 3" may also be used.

Figure 4:
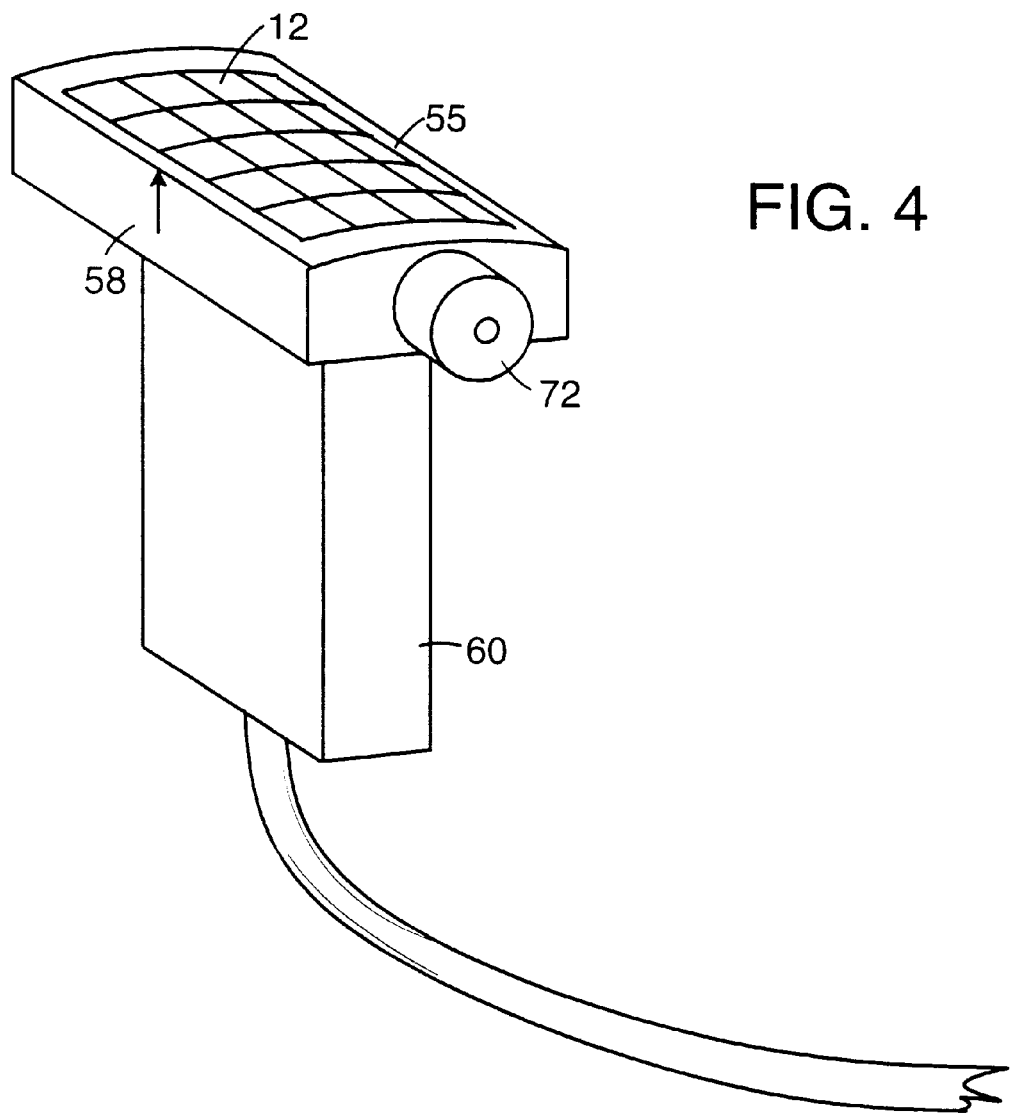
FIG. 4 shows a sensor head.

Having described the structure of the tissue examination device from the point of view of the interface and usage by the clinician, we will now describe the structure of the tissue examination device from the point of view of its operation. FIG. 4 is a block diagram that shows the various components that make up the tissue examination device.

Referring to FIG. 4, the individual resistances of pressure sensors 14 are read by a preprocessing circuitry 20, the output 22 of which is applied to a digital signal processor (DSP) 24. (Although we refer to a DSP in this application, it should be understood that other types of processors, e.g. microprocessors such as those used in personal computers, may be used instead.)

Briefly, preprocessing circuitry 20 sequentially measures the resistance of pressure sensors 14 in response to row and column address signals 23 provided by DSP 24 to provide an indication of pressure applied to the location in array 12 that corresponds to that sensor 14. During each resistance measurement, preprocessing circuitry 20 applies a reference potential (not shown) to the addressed sensor 14, measures the voltage drop induced across that sensor 14, and generates an output 22 corresponding to the voltage drop. Thus, each pressure sensor 14 produces a signal (in this example, resistance-induced voltage) in response to the applied pressure. The operation of preprocessing circuitry 20 is more fully described in the '993 patent.

The preprocessor output signals 22 are digitized (by A/D converters, not shown) and applied to DSP 24 (alternatively, an input stage of DSP 24 may perform the A/D conversion). The set of sequentially produced output signals 22 for all pressure sensors 14 in array 12 is termed a "frame." DSP 24 addresses preprocessing circuitry 20 at a rate sufficient to read 20 frames or more of output signals 22 per second. DSP 24 stores each frame of signals 22 in an area 26a–26n of memory 30. Each memory area 26a–26n contains storage locations 27 which respectively correspond to the locations of pressure sensors 14 in array 12. Thus, each memory area 26a–26n contains a "map" of the pressures detected by pressure sensors 14 in a frame. This map can be viewed as a "pressure signature" of the tissue structures beneath array 12. Accordingly, memory areas 26a–26n contain a time sequence of pressure signatures of the underlying tissue as array 12 is translated across the tissue.

Disk storage device 59 may be used to store various data, including frames of signals 22 and results of processing the frames by DSP 24.

Sensor head 55 also contains motion sensor 70 that detects the motion of sensor head 55 across the tissue and sends this information to DSP 24 for use in determining the position of sensor head 55. Motion sensor 70 derives the motion information from the rotation of a roller 72 connected to sensor head 55. This allows DSP 24 to analyze both the movement of sensor head 55 and the movement of the underlying tissue structure when the sensor head 55 is translated over the tissue. Sensor head 55 also has an alignment marker 58 which indicates the center of the array 12 across the width of sensor head 55. Alignment marker 58 is used in conjunction with an external position indicator (i.e. a reference point or frame of reference) placed over the patient's chest, as described in detail below. DSP 24 uses the output of motion sensor 70 to determine the position of a detected structure relative to the external position indicator and therefore the patient's anatomy, as described in detail below.

A green LED 45 is illuminated when device 10 is powered on. Green LED 45 remains illuminated throughout the tissue examination procedure as a system self check. A red LED 40 and an audio circuit 50 are driven by DSP 24 at various stages of the operation of device 10 to indicate to the clinician whether the clinician is using device 10 properly and how the clinician should operate device 10 at different stages of the examination.

Having described the structure of the device, we will now describe the operation of tissue examination device 10. Briefly, as previously described, tissue examination device 10 may operate in one of two modes depending on the clinician's choice. Briefly, in the first mode of operation, device 10 provides the clinician with a visual graphic display of pressure signatures of the examined tissue and tissue structures. In the second mode of operation, in addition to generating the visual display, device 10 determines areas in individual frames that indicate a suspicious structure in the underlying tissue (hereinafter referred to as "suspicious areas"). Device 10 further provides the clinician with a visual map of the locations of suspicious areas and their relative size and other characteristics. This map may be displayed on visual display 54 or printed out by printer 56. The device may also supply the clinician, based on his/her choice, with a comparison of the results from a current examination with a previous examination and any changes in the number of suspicious areas and their relative sizes.

Figure 5:
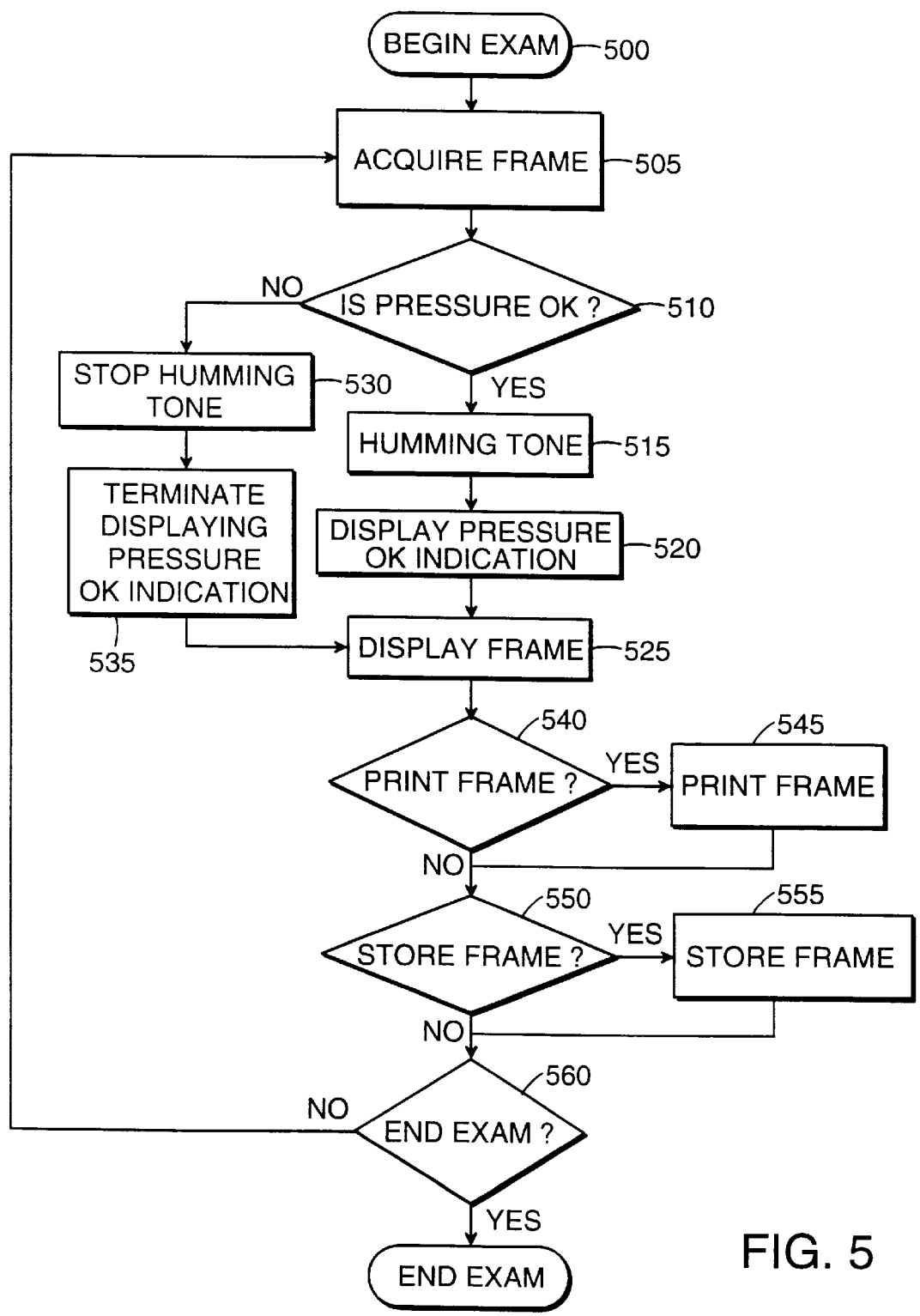
FIG. 5 is a flow chart showing the first mode of operation of the tissue examination device of FIG. 1.

The first mode of operation will now be described in detail in reference to FIGS. 3–12B. FIG. 5 is a flow chart illustrating the first mode of operation. Referring also to FIG. 6, when the clinician turns on device 10, DSP 24 drives visual display 54 to display a graphical user interface (GUI) 600. GUI 600 includes a variety of buttons that may be clicked on by the clinician by using the mouse or trackball. A patient data button 605 provides for inputting or changing patient information, including the patient's name, address, identification number and so on. An exam button 610 causes a menu (not shown) to pop up and be shown to the clinician, offering a number of items including the following: selecting between the first and second modes of examination, beginning an examination, and saving data from a single frame on disk storage 59. A print button 615 permits the clinician to print a single frame on printer 56. An exit button 620 permits ending of an examination. A comparison button 655 is operational during the second mode of operation and allows the clinician to select comparing a current examination with a previous examination. Other features of GUI 600 will be described below in relation to the operation of device 10 in the first and second modes.

After starting the examination (step 500), clinician grasps the handle, presses sensor head 55 against the skin, and translates sensor head 55 across the skin. In response to the pressure, the tissue in essence "pushes back" against a sensor. DSP 24 acquires successive frames of pressure signals from array 12 (step 505) via preprocessing circuitry 20, as explained above (e.g. at 16 frames per second). Because the data from array 12 are sampled data, the data appears to DSP 24 and the clinician, essentially as a series of stationary palpations of the tissue by the array. At the same time translating the sensor head allows the clinician to examine more breast area in less exam time than if the examiner uses stationary palpations.

Generally, the pressure signatures obtained from array 12 are a function of the pressure applied to sensors 14 when the clinician presses array 12 against the body. The resistance of each pressure sensor 14 inversely changes in accordance with the amount of pressure applied to sensor 14. In other words, the resistance of each sensor 14 decreases as applied pressure increases.

Generally, the pressure imposed on sensors 14 increases when sensors 14 are pressed against localized areas of stiffer tissue on, within, or below the softer breast tissue. Examples of such stiffer tissue include normal breast tissue structures—such as the nipple, the inframammary ridge, and underlying ribs—and foreign bodies such as cysts and solid masses (whether or not pathogenic). Consequently, as array 12 is pressed and moved against the breast, the pressure imposed on sensors 14 and, thus the resistance of sensors 14, varies in accordance with the properties of the underlying tissue structures.

The pressure applied by the clinician therefore should be within a selected range in order for the pressure signatures to accurately correspond to the various tissue structure types. The limits of the pressure range are a function of size and sensitivity of the array 12. For array 12 discussed above, the acceptable pressure range is 0.5 psi to 1.5 psi.

Because the proper amount of clinician-applied pressure is important, a preliminary test 510 is performed on each acquired frame to determine whether the average amount of pressure applied to all sensors 14 is within the acceptable range. Preliminary test 510 also determines if a minimum number of sensors 14 are obtaining a reading across width of array 12 such that DSP 24 recognizes that entire array 12 is in contact with the skin.

If the frame passes initial test 510, DSP 24 triggers audio circuit 50 to produce a low pitched humming tone (step 515) and causes a "pressure OK" indication 650 (FIG. 6) to be displayed on display 54 (step 520). DSP 24 maintains the humming tone and pressure OK indication 650 throughout the clinical examination to give the clinician feedback that the applied pressure is correct. The pressure signature in a frame is then displayed to the clinician performing the examination (step 525), as described below.

If the frame fails test 510 (e.g., if the average applied pressure is below or above the acceptable range). DSP 24 stops the humming tone (step 530) and terminates the "Pressure OK" indication 650 (step 535). The frame is still displayed (step 520), however, because the clinician may have decreased or increased the pressure on sensor head 55 in order to perform specific kinds of examination, as will be discussed below.

DSP 24 processes the frames and displays the results in examination display GUI 600. DSP 24 displays a 3-D image to the clinician in a perspective view 630 and a top view 625. Each image includes two axes 635, 640. Axis 635 is the x-axis which corresponds to the width of the array while axis 640 is the y-axis which corresponds to the length of the array. These axes permit signals 22 from individual sensors 14 to be located which may, for example, assist with determining the position of a lump relative to the array. These axes also permit the clinician to measure relative size of a structure, its movement, or its other characteristics. The perspective view also includes a third axis 645 (i.e. z-axis) which represents the pressure detected by sensors 14. The pressure values from sensors 14 are used to generate value along the z-axis for creating the 3-D image of the pressure signature in a frame. The 3-D image is displayed using a color/pressure scale in which ranges of pressure values are defined and each range is assigned a display color. A pressure value which is within a color's range is displayed on visual display 54 with that color. Although GUI 600 uses a gray color scale, other color scales such as the ones used for FIGS. 7A–12B may better display the pressure signatures and improve the clinician's ability to distinguish and examine the various characteristics of the displayed image. (In image 630, a scale on the z-axis 645 shows the actual value of the pressures from sensors 14.) The images may also graphically manipulated and displayed in other ways so as to provide further helpful visual cues. For example, various mapping techniques may be used to show the pressure values.

The clinician may select to print these images for further study or for inclusion in a patient's chart by clicking a print button 615 (steps 540). If the clinician selects to print the image, DSP 24 causes printer 56 to print the selected image (step 545). The clinician may also select to store the images on disk by storing individual frames (step 550). The frames maybe stored for record keeping and for transferring the frames to other clinicians for further study and consultation. The clinician can end an examination by clicking on exit button 620 (FIG. 6) at any point during the examination although DSP 24 acts on that request at the end of processing a frame (step 560). DSP 24 will continue to acquire frames and display them so long as the clinician has not ended the examination.

FIGS. 7A–12B show perspective view and top view of 3-D images (not including axes 635, 640, and 645) of some of the typical structures which may be found in the breast.

We have found that different types of tissue structures have different pressure signatures. The pressure signatures result from the way in which the tissue structures respond to being stressed by the pressures exerted when clinician presses and/or moves array 12 over the breast. The stiffness (elasticity) of a given tissue structure, its composition (e.g., percentage of fat, presence of ducts, and fibrous tissue), its density, its texture, and the degree to which the tissue structure is held in place by surrounding tissue are some of the factors that contribute to the pressure signature of the tissue structure.

Another factor which affects the resulting pressure signature is whether anatomical structures (e.g. ribs) lie beneath the tissue structure. These factors, in combination, are usually sufficiently different for various types of tissue structures (e.g., normal breast structures such as ribs, nipples, ligaments, etc., and foreign structures such as cysts, solid masses, and other lumps with respect to normal tissue stiffness) that the pressure signatures of these structures are distinguishable from each other and will appear to have different 3-D characteristics when displayed.

By graphically displaying these pressure signatures in 3-D, the pressure signatures of the various underlying tissue structures appear to have various shapes whose characteristics are based on the type of underlying tissue structure. Therefore, the clinician can readily identify the underlying tissue structure by analyzing these shapes and their characteristics. The characteristics that the clinician may look for in a shape include the following:

size of the shape;

height or elevation of the shape's various areas against the background;

flatness of the shape;

peakedness of the shape;

whether the shape has a plateau;

outline of the shape, e.g., whether it is generally round or elongated;

slope or gradient of the shape along any part of the shape;

movement of the shape in response to moving or rolling the sensor head over the tissue;

change in the shape over time; and change in the shape in response to changing pressure.

We will now describe in detail how each of the various shapes corresponding to various types of tissue structures has one or more of the above characteristics. A clinician trained in using device 10 can examine a tissue and identify various structures within the tissue, based on the 3-D image of the pressure signatures from array 12. The clinician may analyze the shapes to identify the dominant, discrete, and different characteristics of a particular shape which would make it more likely that the shape represents one or another underlying structure.

Generally, there are four categories of structures which a clinician may encounter in an examination. These categories consist of hard structures (including carcinomas), soft structures, ribs and other normal tissue. Pressure signatures corresponding to these categories will now be described as an illustration of the different foreign structures a clinician may observe during an examination and various characteristics which the clinician can use to identify these structures.

In FIGS. 7A–12B, 3-D images of pressure signatures are shown in accordance with a color scale in which the various color shadings represent various pressure values. As shown by the key in these figures, red represents the highest pressure value and blue represents the lowest pressure value. (The same color scale is used in FIG. 6.)

Figure 7A:
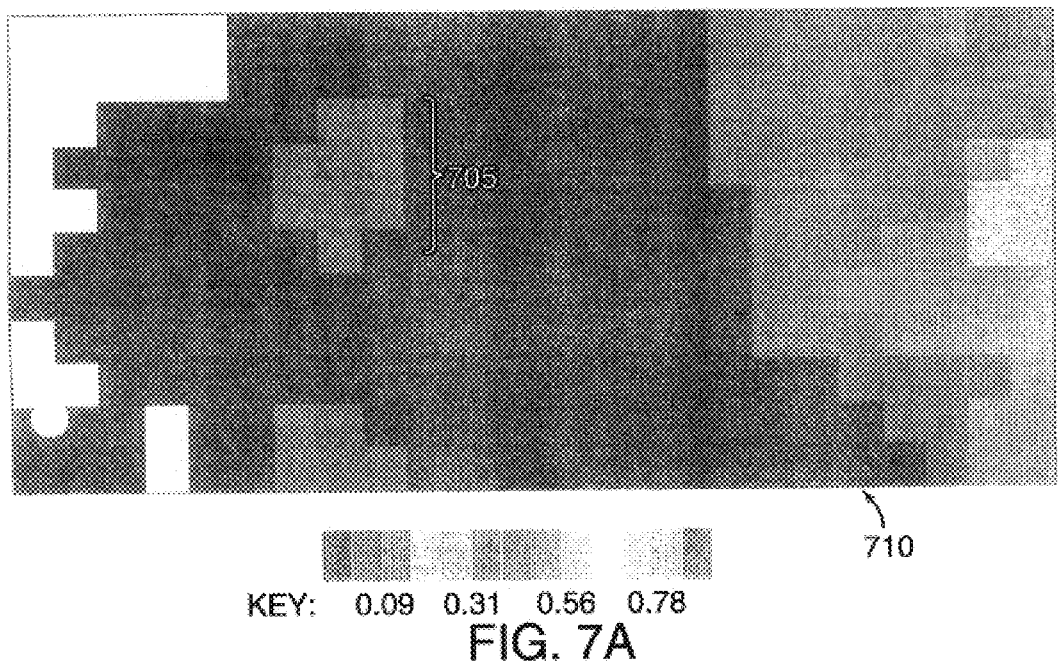
FIG. 7A shows a top view of a three dimensional image of a pressure signature of normal tissue.
Figure 7B:
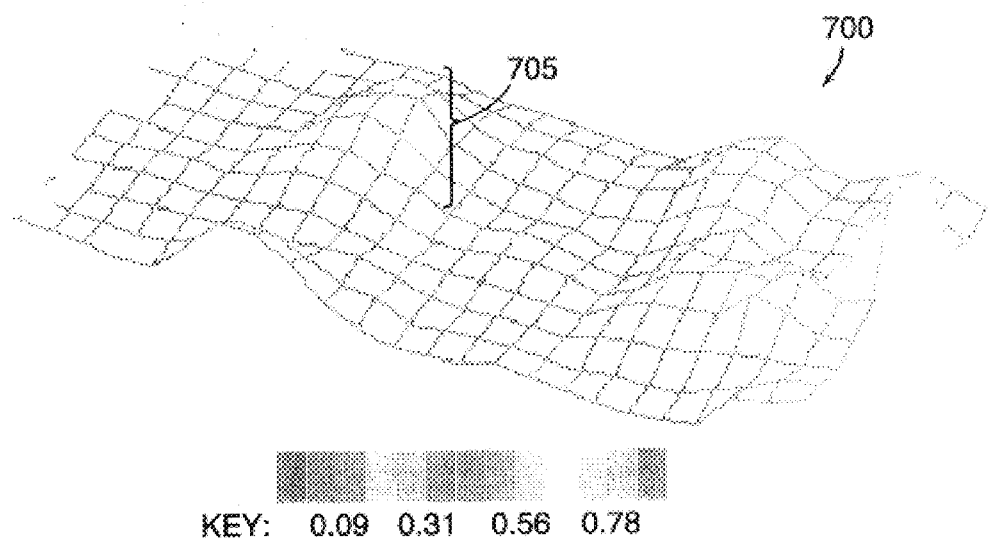
FIG. 7B shows a perspective view of a three dimensional image of a pressure signature of normal tissue.

Referring to FIGS. 7A and 7B, top view 705 and perspective view 700 of a 3-D image of a typical pressure signature of normal breast tissue generally show a terrain with slight local elevations 705. These elevations correspond to areas of higher density in breast tissue. Such areas of higher density are common. Moreover, these clusters do not appear as distinctly different from one another and do not have a great deal of continuity from one to another. Since the there are no dense structures in the tissue, the pressure response of normal tissue has a low pressure value. Therefore, plan view image 710 in FIG. 7A shows a fairly even and "flat" profile.

Figure 8A:
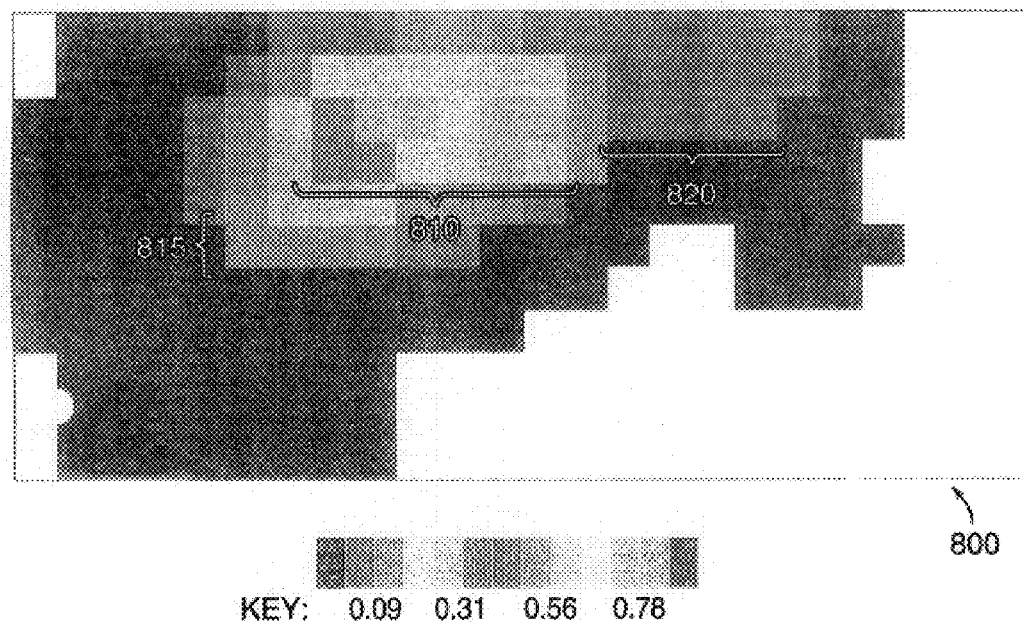
FIG. 8A shows a top view of a three dimensional image of a pressure signature of a rib.
Figure 8B:
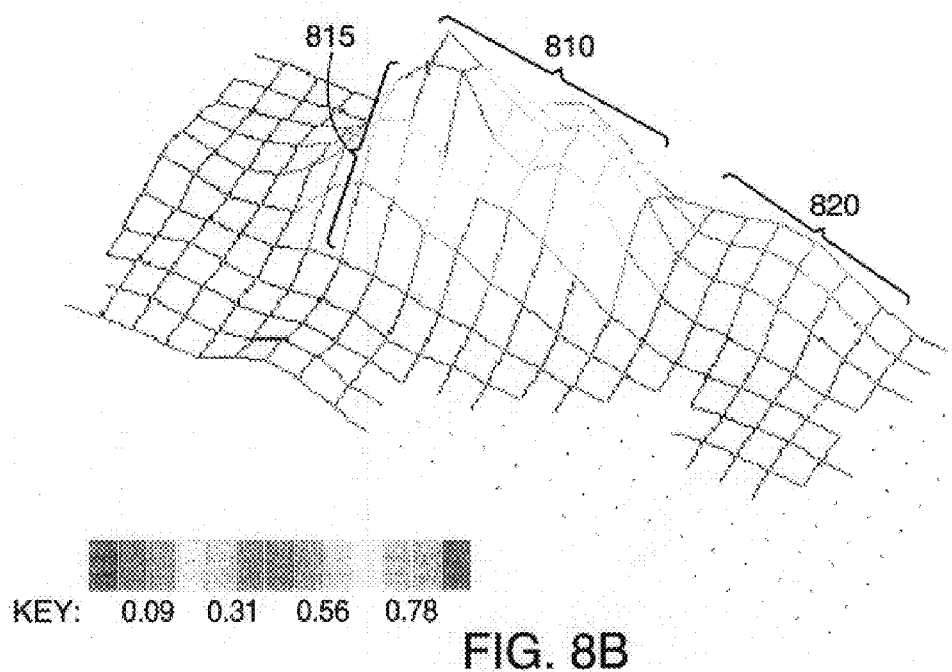
FIG. 8B shows a perspective view of a three dimensional image of a pressure signature of a rib.

In contrast, consider FIGS. 8A and 8B, which show top view 800 and perspective view 805 of a 3-D image of a pressure signature of a rib. Because a rib is anchored to the skeletal system, when a clinician presses sensor array 12 against the tissue overlying a rib, the immobile rib effectively "pushes back" against sensors 14. In both the top and perspective views, a rib appears as an elongated area with a flattened plateau in its center 810. Edges 815 along the width of a rib are sharply defined and rise relatively rapidly to plateau 605 at the boundaries of the rib. Edges 820 along the length of a rib, however, have a lower slope. If the rib is sensed by placing array 12 parallel to the rib, the pressure signature will be elongated due to the elongation of the rib (in FIGS. 8A and 8B, the rib appears obliquely).

Another distinguishing characteristic of the rib is its firmness. Since the rib is a bone, it does not change shape with applied pressure. Other structures in the breast that are less firm than bone deform differently in response to a variety of applied pressures and accordingly provide different visual pressure signatures. For example, the pressure signatures of such structures may be seen to gradually flatten as applied pressure increases. (This fact is used in a specific method of using device 10 to distinguish between soft and hard structures, as will be described in detail below.) Ribs also appear to have more jagged texture than softer tissue.

Figure 9A:
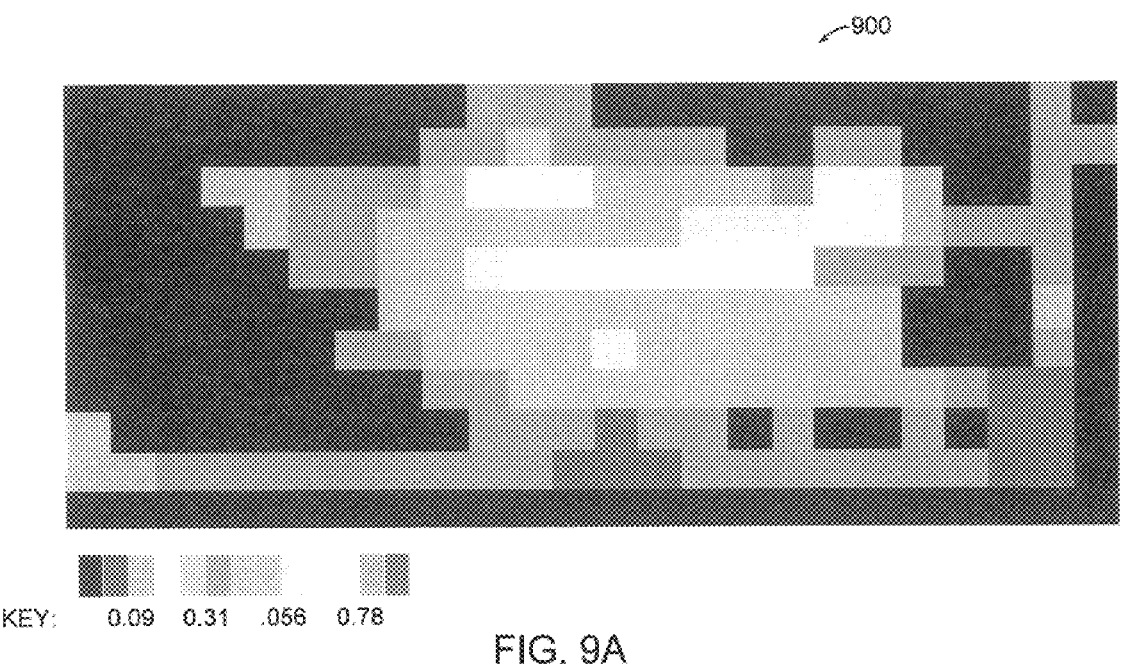
FIG. 9A shows a top view of a three dimensional image of a pressure signature of an inframammary ridge.
Figure 9B:
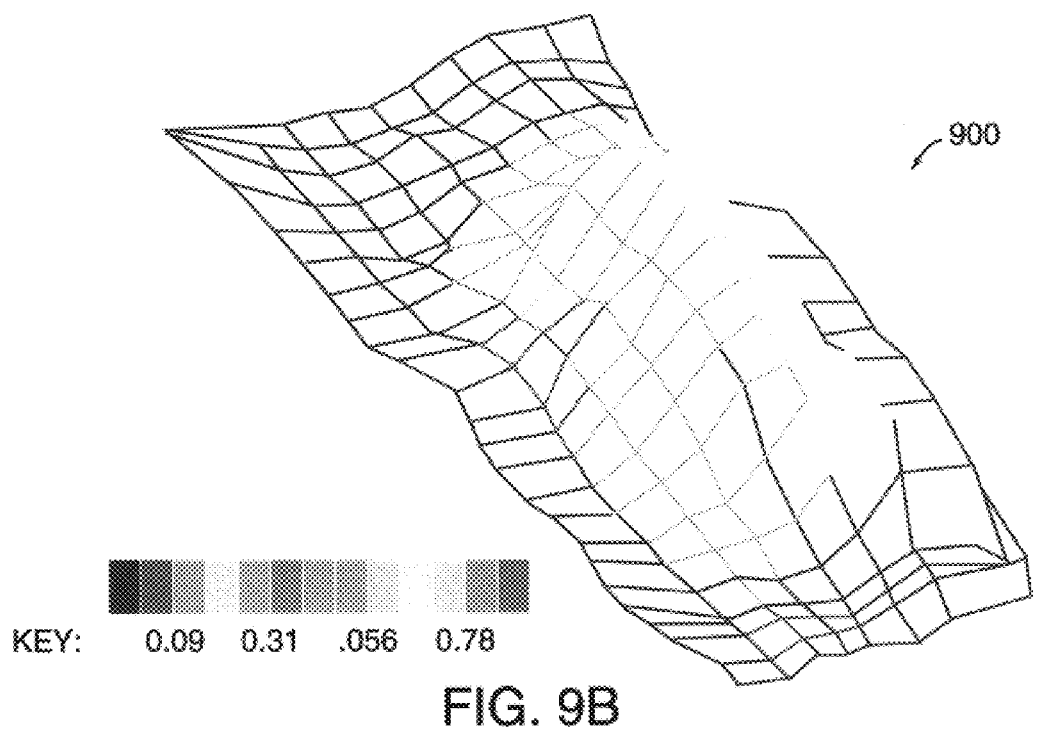
FIG. 9B shows a perspective view of three dimensional image of a pressure signature of an inframammary ridge.

FIGS. 9A and 9B show top view 900 and perspective view 905 of a 3-D image of a pressure signature of an inframammary ridge. The inframammary ridge is a relatively wide structure that runs along the base of the breast and provides support for the breast tissue. Accordingly, the pressure signature of the inframammary ridge is relatively wide and long (depending upon the orientation of array 12 relative to the ridge). Inframammary ridge appears as a structure which has a pressure signature similar to a rib. Because of its elongated shape, in this case the ridge is easily distinguishable from carcinomas which generally have a distinct peak area, as will be described below. The pressure levels detected by sensors 14 show a ridge of high pressure values as opposed to a concentration of high pressure values in limited areas.

Figure 10A:
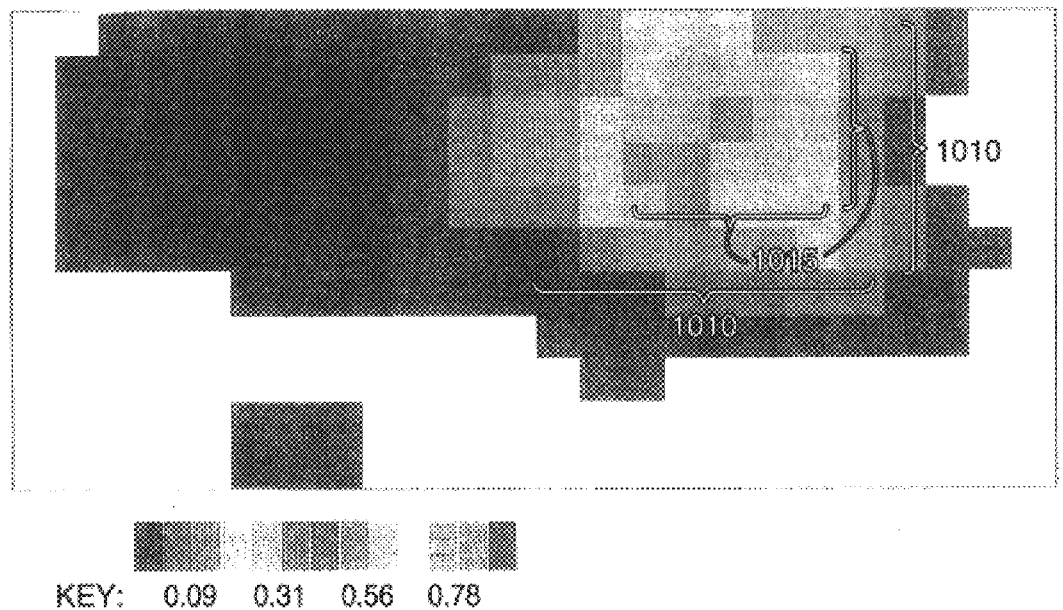
FIG. 10A shows a top view of a three dimensional image of a pressure signature of a fluid filled cyst.
Figure 10B:
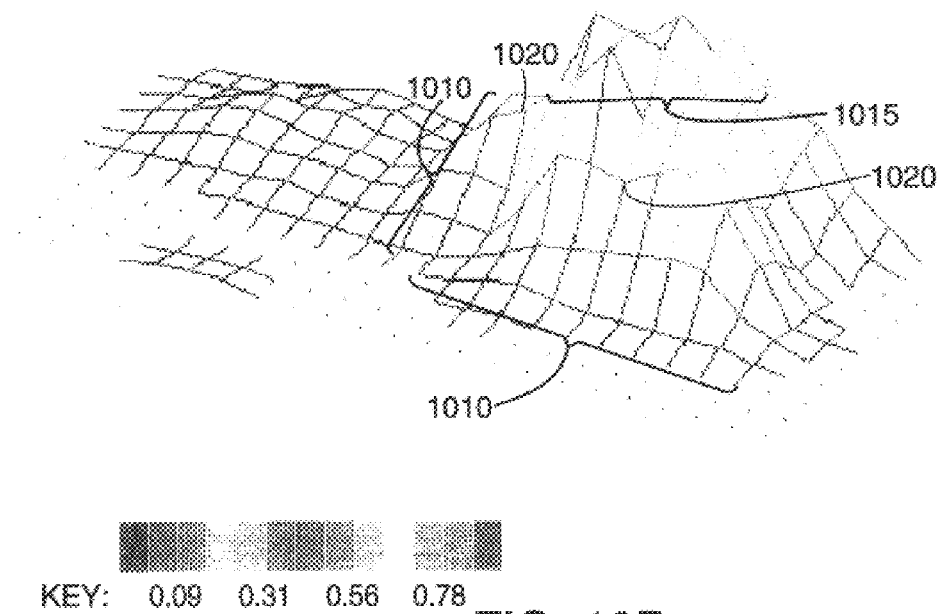
FIG. 10B shows a perspective view of a three dimensional image of a pressure signature of a fluid filled cyst.

FIGS. 10A and 10B show a top view 1000 and a perspective view 1005 of a 3-D image of a pressure signature of a soft shelled cyst. Cysts are fluid filled structures with a hard or soft shell containing that fluid. The pressure signature of a cyst is a function of the hardness of the cyst. A hardshelled cyst is generally indistinguishable from a solid mass (discussed below). A soft shelled cyst has a correspondingly soft (i.e., low amplitude) pressure signature in which an area 1010 of relatively high pressure has a plateau 1015. This plaeau is characterized by a uniform perimeter, that typically is circular. This plateau is the effect of array 12 flattening the cyst as a result of the clinician pressing the sensor head against the breast.

Cysts also have discrete boundaries, which is another characteristic that enables the pressure signature of a soft cyst to be distinguished from the pressure signatures of other structures. A cyst is essentially a fluid filled body, and the fluid pressure within the cyst tends to make it circular (in two-dimensions) with well-defined edges. Accordingly, as array 12 is moved across such an edge, the pressure drop is much more dramatic than with, for example, a diffuse tumor, which would have less discrete boundaries. The well-defined edges of the cyst are reflected in the pressure signature by medium differential pressures at edges 1020. The well-defined edges appear as having sharp gradients or slope; that is, the pressure response varies greatly over a small area.

Figure 11B:
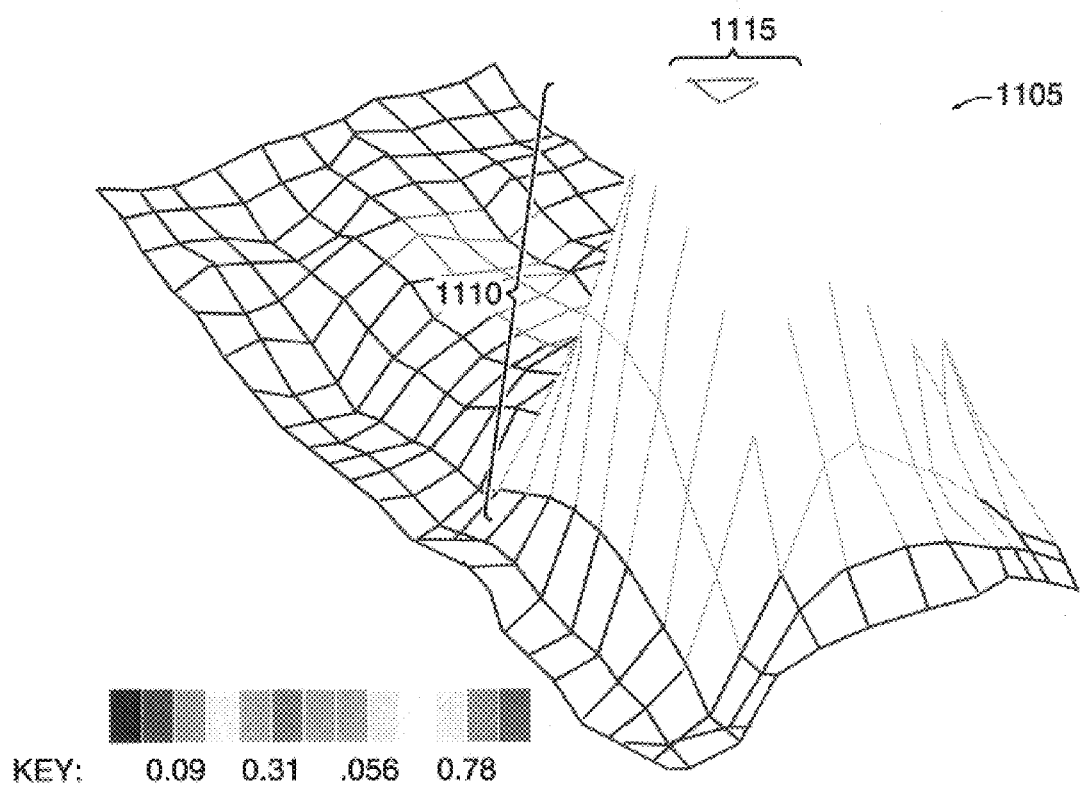
FIG. 11B shows a perspective view of a three dimensional image of a pressure signature of a benign hard lump.
Figure 11A:
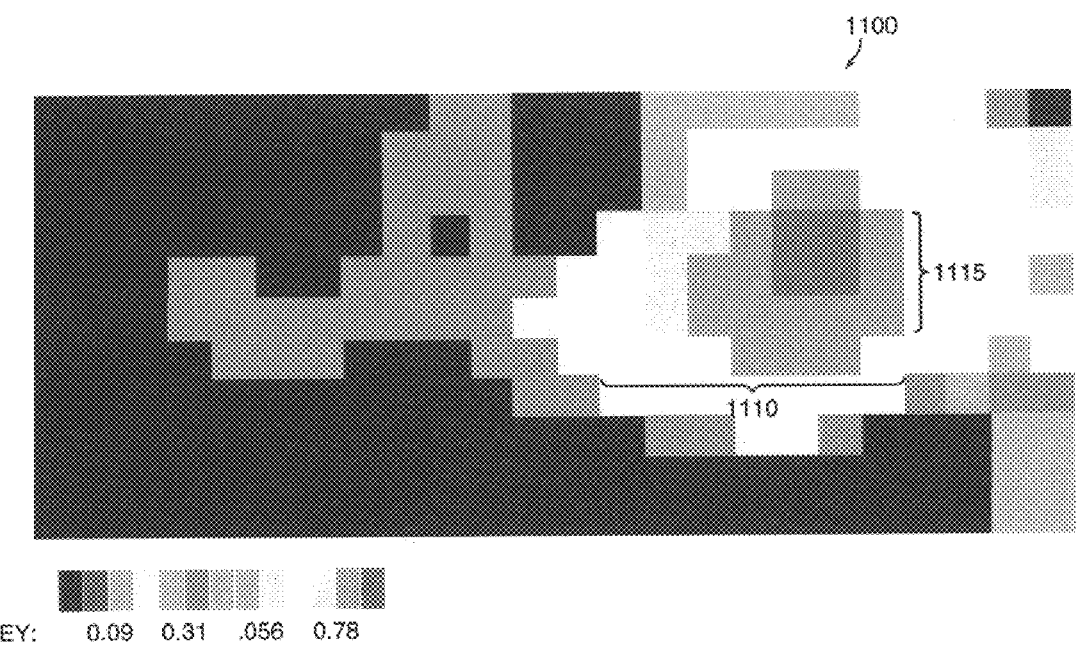
FIG. 11A shows a top view of a three dimensional image of a pressure signature of a benign hard lump.

FIGS. 11A and 11B show a top view 1100 and a perspective view 1105 of a 3-D image of the pressure signature of a benign solid mass (in this case, a fibroadenoma). The 3-D image in FIGS. 11A and 11B pressure signature is similar to that of a hard-shelled cyst. A solid mass (or a hard lump), such as a hard-shelled cyst, typically has discrete boundaries much like a soft shelled cyst. A soft cyst is often indistinguishable from a solid mass by manual palpation. Indeed, the pressure values obtained from a benign solid mass define a pressure signature which is similar to a cyst pressure signature. The pressure signature of a hard structure has relatively sharp edges 1110 (which correspond to the discrete edges of the mass) and a central region with a large amplitude 1115. But unlike the pressure signature of a soft cyst, the central region 1115 of the pressure signature, which corresponds to the pressures produced by pressing array 12 against the high-elevation areas of the mass, is relatively small. By comparing perspective and top views of the 3-D pressure signature images of a soft shelled cyst (FIGS. 10A & 10B) and a hard mass (FIGS. 11A & 11B), the distinction between the pressure signatures of the two types of foreign structure will become more apparent. Area 1015 in FIGS. 10A and 10B is fairly flat and large as result the cyst being flattened by the pressure from sensor head 55. In contrast, there is no flattening or enlargement of the central region 1115 of a hard mass caused by sensor head 55.

Unlike a rib, which as discussed is anchored and thus "pushes back" against the pressure applied by the clinician, cysts and benign solid masses are relatively free to move in response to the clinician-applied pressure. Accordingly, although the cyst pressure signature and the solid mass pressure signature have distinct edges, the edges are not as well-defined as the edges 810 of a rib pressure signature (FIGS. 8A and 8B). This difference provides one way of distinguishing the pressure signatures of cysts and benign solid masses from that of a rib. Another way is the elongated shape of the image of a rib.

Figure 12A:
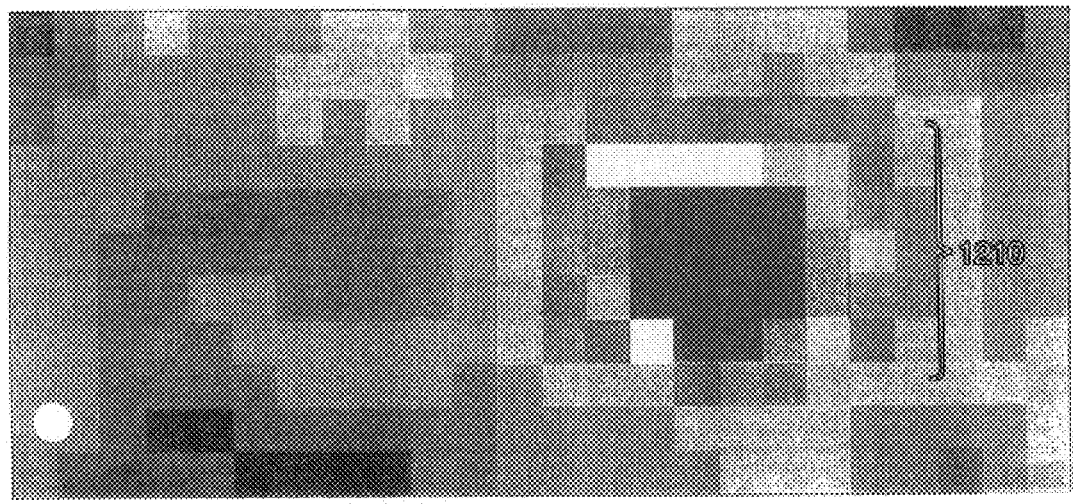
FIG. 12A shows a top view of a three dimensional image of a pressure signature of a carcinoma.
Figure 12B:
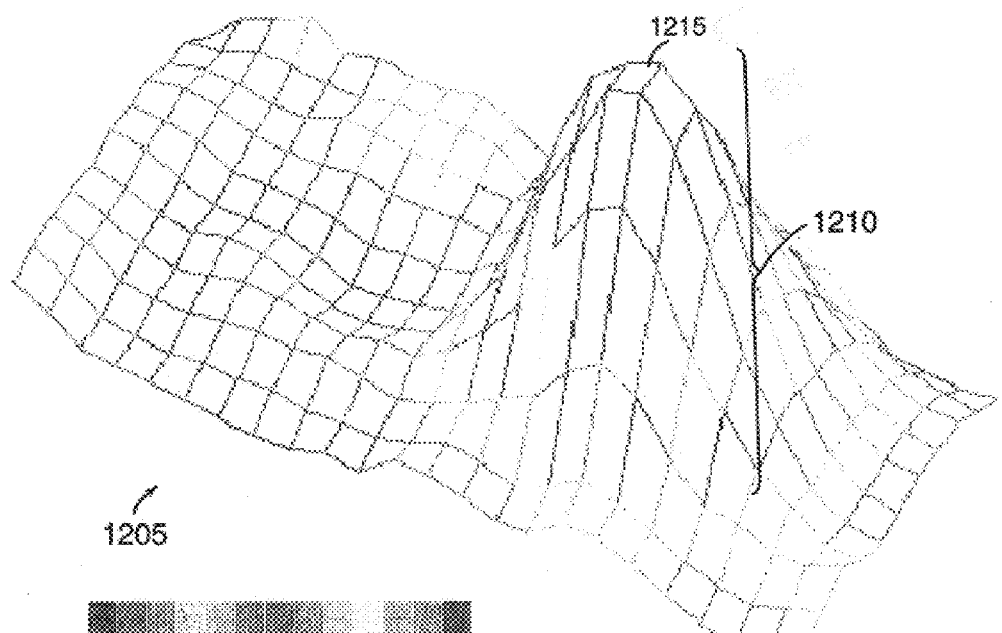
FIG. 12B shows a perspective view of a three dimensional image of a pressure signature of a carcinoma.

Referring to FIGS. 12A and 12B, which show a top view 1200 and a perspective view 1205 of the 3-D image of the pressure signature of a carcinoma, one way in which a carcinoma differs from a cyst or a benign solid mass is that a carcinoma typically is diffuse and infiltrates surrounding tissue. As a result, the carcinoma is anchored to the surrounding tissue and does not move like a cyst or a benign mass in response to palpation. The pressure signature of a carcinoma, like that of a rib, is harder—that is, has larger amplitudes—than that of either a cyst or a benign solid mass. Unlike a rib, however, edges 1210 of a carcinoma are not discrete, and thus the pressure level at the boundaries of the carcinoma does not decrease as sharply as that at the edges 810 of a rib (see FIG. 8A and 8B). Carcinomas also are not flattened by the pressure sensor. Therefore, peak 1215 of a carcinoma will be distinct. In case of the carcinoma shown in FIGS. 12A and 12B, peak 1215 consists of one sensor area. This also suggests that the carcinoma is a small carcinoma. However, despite the small size of the structure the amplitude of the response is quite high and the edges of the response spread over 3 to 6 sensors 14, suggesting connectedness of the structure to surround tissue.

One way of enhancing the images shown by the device is to set a lower threshold below which the variations in signal are not shown. In effect, device 10 would filter out much of the small variations in background due to variations in tissue density (described in reference to FIGS. 7A and 7B). Therefore, device 10 accentuates the shape of other structures since they would be easily distinguished from the background. Moreover, in this way, device 10 also clearly shows the size of the structure.

Another way of enhancing the images includes generating a topographical map of a pressure signature. In this way, adjacent sensors having the same approximate pressure values are displayed by a continuous line. In such an image the value represented by a particular line will be displayed with the image. Another way of enhancing the image is to display an outline of a structure or a gradient or rate of increase along a certain dimension of the image or a shape in the image. Other enhancements may include using various known segmentation techniques to manipulate the 3-D image.

The clinician may also perform other examinations which would help him/her better identify structures in the underlying tissue. For example, he/she may roll sensor head 55 from side to side over an identified lump to determine its response. This rolling movement is similar to manual breast examination and may give the clinician further information regarding the foreign structure, such as its mobility and the extent to which it is anchored within the breast, thereby further distinguishing carcinomas and ribs from hard lumps. The clinician can also learn about the degree of connectedness of the tissue during the normal translation of the sensor head, by observing the motion of the structure under the sensor head as displayed in the 3-D image.

The clinician may also gradually increase or decrease the pressure on sensor head 55. By doing so, he/she may observe the changes in the pressure signature of the structure, such as a flattening response which would suggest a soft structure as opposed to a hard structure like rib. The degree of flattening may also provide further clue as to whether, for example, the object is a hard-shelled or a soft-shelled cyst.

Clinician 1 therefore can visually distinguish various structures from one another based on the characteristics of the pressure signatures of the structures displayed in the perspective and top views of the 3-D image. Those characteristics of the underlying structures which are used by a clinician in a manual examination (e.g. hardness, texture, mobility, and discreetness of edges) are made available to the clinician in the 3-D image. As described above, the images are also enhanced to make the detection of the structures easier. Specifically, the clinician can easily distinguish carcinoma and benign solid masses (such as fibroadenomas and hard-shelled cysts) from soft-shelled cysts. Moreover, the clinician can distinguish more advanced carcinomas (which are more diffuse and connected) from benign solid masses and less advanced carcinomas (which are less diffuse and connected, and are like benign solid masses).

The clinician may also investigate structures over time, for example, by remembering the location of the structure and comparing printed out or stored pressure signature of a structure in a previous examination with the structure's current pressure signature. The clinician may determine changes in size, connectedness, hardness, etc. of the structures over time.

In identifying and examining the characteristics of the displayed 3-D images, the clinician may also concentrate of the discrete, dominant, and different characteristics of a structure. Discreteness is generally a measure of how distinctly the structure, for example, has a perimeter that defines it compared to the surrounding tissue. Dominance is generally a measure of when a structure, for example, has more pronounced characteristics (e.g. stiffness or pressure signal strength) compared to the surrounding tissue. Difference can generally be thought of as a statistical measure. For example, difference requires asking how different an identified structure and its characteristics are from other structures and their characteristics. These other structures may be those in the particular patient's breasts or those known from experience by the clinician.

We will now describe the second mode of operation of device 10, in which device 10 operates also as an expert system and augments the display of the 3-D image with additional functions. Before describing the second mode in detail, we will provide an over view of the second mode, the method of its operation, and the expected results.

As described above, in the second mode, the clinician follows a specific examination methodology and procedure to perform the examination. As the clinician performs the examination, device 10 displays the pressure signatures as in the case of the first mode. The clinician during the examination is able to view the pressure signatures and evaluate the shapes presented in the image, as described in the first mode of operation.

In the second mode, device 10 assists the clinician by confirming the clinician's diagnosis or alerting the clinician to areas that should be further examined by the clinician. DSP 24 of device 10 analyses the frames of signals in accordance with the method disclosed in U.S. patent application Ser. No. 08/757,466 entitled "Tissue Examination", as filed on Nov. 27, 1996 incorporated by reference in its entirety, hereinafter referred to as "the '466 application". The '466 application discloses a method in which frames of signals 22 are analyzed to identify areas in each frame which may be pressure signatures of carcinoma, (the areas are referred to as "suspicious area" and "SA" in this application). Upon identifying such an area, device 10 informs the clinician of the presence of the area.

Device 10 also determines the position of such identified suspicious areas relative to a reference point on the patient's body. The clinician follows a specific procedure for examining the patient's breasts which allows DSP 24 to use the output of roller 72 and sensor array 12 to determine the location of the frames of signal relative to the reference point. This method of examination will be described below in detail in reference to FIG. 14.

After determining the position of the suspicious areas, device 10 creates a database where each record stores information regarding one suspicious area (FIG. 20 shows the record structure of such a database). Information in the records may include the size and location of the suspicious areas, the frames in which the suspicious areas appeared, the normalized or averaged pressure signatures of the areas, and the total number of the areas in the breast. Device 10 also creates a visual map of the location of these areas, which may be visually displayed (as shown in FIG. 21) or printed (as shown in FIG. 22).

The database and the map provide the clinician with quantitative information regarding the suspicious areas in the breast. The clinician therefore can easily refer to the database and the map to review the results of the examination after the examination or at a later date. Moreover, the database can store such quantitative information such as the size of the suspicious area or specific results of the analysis according to the '466 application, such as the likelihood of the suspicious area representing a carcinoma or the curvedness of the pressure profile. Such quantitative information make it easier for the clinician to characterize a structure found during the exam. The clinician can more precisely communicate the characteristics of the structure using quantitative rather than descriptive information (e.g. "It is 1 cm$^2$ in size" as opposed to "it is the size of an acorn"). Moreover, the data stored in the database and the map enable a second clinician to re-evaluate the results, for example, to offer a second opinion.

Given that the results of the examination are stored, they can also be compared to results of a future examination. Keeping track of a structure through a number of examinations enables the physician to distinguish benign structures from malignant structures, since malignant structures grow.

The examination procedure used by the clinician ensures that the reference point relative to which the location of the suspicious areas are determined remains constant. Device 10 uses the positional information determined for each suspicious structure to ensure that suspicious structures from two different examinations can be matched with one another and compared. The results of such comparison then can be visually displayed (FIG. 25) or printed out (FIG. 26). Once again, since the characteristics of the structures are quantitative, they can easily be compared and the result of that comparison can also be expressed quantitatively, e.g. by percentage of change over time. The clinician, therefore, has an added dimension of assistance for diagnosing carcinoma.

During the second mode, the display of the 3-D image may also be enhanced based on the results of the analysis performed by DSP 24 to identify the underlying tissue. For example, other information may be simultaneously displayed with the 3-D image. This information includes the pressure values, boundaries of structures (based on identifying the suspicious structure), location of peak pressure values, and curvedness. The enhancements can also include showing a topological image or a contoured of the pressure signatures, identifying various pressure levels.

We will now describe the second mode of operation of device 10 in detail in reference to FIGS. 13–22.

As previously pointed out, in order for the device to be able to determine the position of the suspicious areas, the clinician follows a specific procedure for examining the patient's breasts. By following this procedure, the clinician supplies DSP 24 with data that enables it to determine the position of the suspicious areas relative to the patient's anatomy. We will now describe in detail the steps the clinician is required to take to perform the examination according to this procedure.

Referring to FIG. 14, prior to the examination, the clinician attaches a polyurethane sheet to the patient upper torso. The method of attachment, which will described below, aligns the sheet such that a lateral line near the top of the sheet extends approximately along the patient's shoulder blades. Sheet 1400 provides an external reference point for moving sensor head 55 so that DSP 24 can determine the relative positions of each frame with respect to other frames. Sheet 1400 has a number of evenly spaced, parallel lines 1405 extending axially from the lateral line along the shoulder blade.

The clinician performs the examination by translating the sensor head across the breast, in a series of vertical sweeps, while alignment marker 58 is aligned with one of axial lines 1405 during each such sweep (a single translation of the sensor head along one axial line will be called a "sweep"). Lines 1405, therefore, essentially serve as guides during translation of sensor head 55 across the tissue. During each sweep, the clinician translates the sensor head starting at the lateral line along the shoulder blade, along the axial line, to the bottom of the breast. Device 10 reads, stores, and analyzes the frames of signal from the sensor array for the sweep. Device 10 also displays the frames as was the case in the first mode of operation.

At the end of the sweep, the clinician lifts the sensor head to begin the next sweep along the adjacent axial line to the right. Lifting the sensor head causes the sensor array to output a series of zero pressure frames. As we will describe below, DSP 24 monitors the output of the array continuously for these zero pressure frames. When the sensor head is lifted from the skin for approximately 2 seconds, DSP 24 assumes that one sweep has ended and the next sweep is about to begin.

To begin the next sweep, the clinician aligns the sensor head with the adjacent axial line and the lateral line along the shoulder blade. The clinician then translates the sensor head in the same way as in the first sweep. At the end of that sweep, the clinician lifts the sensor head and performs another sweep along the adjacent line 1405 to the right. In this manner, the clinician examines all of the patient's breast tissue. It should be noted that the distance between lines 1405 is one half the width of sensor array 12. Hence, each area on the breast is generally covered twice. Any suspicious area that may fall at the edge of a sensor array 12 during one sweep will likely be covered by a central part of array 12 during an adjacent sweep.

As will be described below, as DSP 24 obtains each frame of signals, DSP 24 stores with that frame two pieces of information which is then used by DSP 24 to calculate the position of the frame. First, DSP 24 stores with each frame a sweep index number, assigned sequentially to each sweep by DSP 24, identifying which sweep the frame belongs to. The sweep index number can be used to determine the lateral position of sensor head relative to the left most point in the examination. Second, DSP 24 stores the output of motion sensor 70 when the frame is obtained. The output of the motion sensor identifies the relative position of the sensor head to the lateral line along the shoulder blade. Based on these two positional data, DSP 24 determines the location of any frame in the examination and any suspicious area in any such frame, as will be described in detail below.

Because DSP 24 based on the clinician's choice also compares the results from a previous examination with the current examination, the relative positional information of the suspicious areas must be anchored to an external reference point that does not vary significantly from one examination to the next.

In order to provide a constant reference point from one examination to the next, the shoulder joints and the sternum are used as reference points for placing sheet 1400 on the patient. The clinician is required to follow the same procedure for placing sheet 1400 from one examination to the next to ensure uniformity in positioning sheet 1400 relative to the patient's chest.

The procedure is as follows. The patient is required to lie back, which results in her breasts being flattened against her chest, with her arms at her sides. (The flattening of the breasts makes the examination more precise because more deep lumps will be closer to the surface.) Polyurethane sheet 1400 has two strips of adhesive tape, 1410 and 1415, which are used to attach sheet 1400 to the patient's chest. Adhesive strips 1410 and 1415 are marked in their center with center marks 1420 and 1425 which are connected together with a center line 1430. Center line 1430 is aligned with the sternum while upper adhesive 1410 is aligned with the collar bone in such a way that the upper adhesive tape 1410 coincides with the two shoulder joints. Once properly aligned, sheet 1400 is attached to the patient using adhesive tapes 1410 and 1415. The patient then lifts her arms until her arms lie parallel to one another on either side of her head. This results in better exposure of the patient's breasts to the examination and additional flattening of the patient's breasts.

The clinician translates sensor head 55 along lines 1405 beginning at the upper adhesive tape 1410. Each translation along one of lines 1405 will be referred to as a "sweep." The clinician examines both breasts beginning with the left most line and continuing from one line to the next until both breasts have been examined.

FIGS. 13A and 13B, in combination, are a flow chart showing the data processing procedure performed on frames of signals 22 to generate a map of foreign structures identified in the current examination. FIG. 13 shows the interrelationship between FIGS. 13A and 13B. Referring to FIGS. 6 and 13A–B, after preparing the patient for the examination, the clinician selects the second mode of operation in pop up exam menu 610. Prior to beginning of examination, the clinician enters a series of vital patient information (step 1300). First, the clinician enters the patient's name, address, identification number and so on. Second, the clinician enters medically significant information which device 10 may use to calibrate the testing performed by device 10. This information may include age, fitness level, smoking habits, percent body fat, child bearing history, breast feeding history, breast cup size, and so on. Breast cup size may also be used for scaling the visual display and printed results, as will be described below.

The clinician next selects to begin the examination from the menu that "pops up" when exam button 610 in FIG. 6 is clicked (step 1305). Prior to obtaining any frames of signals 22 from the first sweep, device 10 assigns a sweep index number of one to the frames of data from the first sweep (step 1310). The sweep index number is incremented for each subsequent sweep. The sweep index number is stored with every frame in memory locations 26a–26n. The sweep index number indicates the lateral position of any suspicious areas and is used to create a map of the breast, as will be described below.

After DSP 24 has assigned a sweep index number to the current sweep (step 1310), DSP 24 acquires a frame from preprocessing circuit 20 (step 1315) and acquires the relative position of the frame from motion sensor 70 (step 1320).

Generally, DSP 24 calculates the position of a frame relative to sheet 1400 using the positional information from motion sensor 70 and the sweep index number. Based on the position of a frame, DSP 24 can also calculate the position for every sensor in that frame relative to sheet 1400. Referring to FIG. 15, we will now describe the coordinate system that DSP 24 uses for calculating the position of the suspicious areas. The co-ordinate system used by DSP 24 has axial and lateral axes, where both lateral values and axial values increase in the direction sensor head 55 is moved as the patient is examined. The center of the upper most frame in every sweep is given an axial value of zero. The center of the frame in the first sweep in turn is given a lateral value of zero.

To calculate the axial value 1500 for the center of a frame, DSP 24 uses the output of the motion sensor 70 as measurement of the distance of the frame from upper adhesive strip 1410. To calculate lateral value 1505, DSP 24 multiplies the sweep index number by one half the width of sensor array 12 (which is the distance between lines 1405).

To calculate a lateral value and an axial value of a sensor 1510, DSP 24 first calculates a lateral value (X) 1515 and an axial value (Y) 1520 of sensor 1510 relative to the center of sensor array 12. Adding these values to lateral value (Fx) 1505 and axial value (Fy) 1500 of the center of the frame provides the lateral and axial values of sensor 1510.

As described above, at the end of each sweep the clinician lifts the sensor head from the tissue. DSP 24 checks for this by counting the number of frames in a sequential series that show zero pressure on the sensor array. If more than 30 frames (i.e. about 2 seconds), DSP 24 assumes that the sweep has ended and that a new sweep is about to begin. We will now describe the steps taken by Dsp in detail in reference to steps 1325–1335.

DSP 24 examines each acquired frame to determine whether the sensor array has been lifted from the skin, by examining whether the frame shows approximately zero pressure on sensors 14 (step 1325). If so, DSP 24 increments the zero pressure frame counter by one (step 1330). If there are 30 consecutive zero pressure frames (step 1335), which corresponds to approximately 2 seconds, DSP 24 determines that the clinician has ended the current sweep by lifting the sensor head to start the next sweep (step 1337). An average sweep lasts about 10–12 seconds and provides about 200 frames when sampled at 16 Hz.

At the end of each sweep, the clinician may end the examination by inputting an appropriate answer to a question displayed on the screen or merely begin the next sweep (step 1340). (Pressing the Exit button 620 shown in FIG. 6 aborts the examination and the acquired data is not analyzed.) If the clinician does not end the examination, DSP 24 resets the zero-pressure counter (step 1345) and increments the sweep index number by one (step 1310). As the clinician translates the sensor head along the adjacent line for the next sweep, DSP 24 obtains a new set of frames for that sweep which it indexes and stores as it did with the frames in the first sweep.

If an acquired frame is not a zero pressure frame (step 1325), then DSP 24 assumes that the sweep is continuing. DSP 24 resets the zero pressure frame counter for counting future zero pressure frames (step 1350). DSP 24 then causes the top view and perspective view of the 3-D image of the non-zero pressure frame to be displayed in the same manner as in the first mode (step 1355). It should be noted in some embodiments, the frame is not displayed during the second mode of operation.

After causing the 3-D image to be displayed, DSP 24 analyzes the non-zero pressure frame in accordance with the method in application '466 to determine the suspicious areas in that frame (step 1360). FIG. 16 shows the general outline of the steps DSP 24 takes in accordance with the '466 application. We will briefly describe in reference to FIG. 16 the steps DSP 24 takes to analyze a frame of signals in step 1360. The steps are described in detail in the '466 application.

The '466 application generally features performing a plurality of processing tests on the pressure signature signals from sensors 14, discriminating between the different types of the underlying tissue structures based on the results of the tests, and determining areas which might have suspicious structures (i.e., the suspicious areas). The processing tests of the '466 application serve two purposes. The first is to determine the pressure signature of the underlying tissue structure—that is, the manner in which the tissue structure responds to applied pressure. The second is to compare the pressure signature to pressure signatures which have been empirically determined to correspond to structures normally found in the breast (such as the nipple, the inframammary ridge, or ribs), and potentially foreign structures (such as cysts, benign masses, or carcinomas), thereby providing a sensitive, yet accurate, way of discriminating between the normal and potentially foreign structures. Normal tissue structures are therefore discriminated from potentially foreign tissue structures based on the results of the tests.

Referring to FIG. 16, prior to any testing on the frames, as in the first mode, DSP 24 first determines whether the clinician is pressing the sensor array with a proper amount of pressure against the tissue (step 1600). In this case, however, if the clinician is not applying proper pressure, the frame is not analyzed any further. If proper pressure is being applied, a humming tone is generated by the audio circuit 50 (step 1605). If not, the humming tone is stopped to indicate to the clinician to adjust the applied pressure (step 1610).

The processing tests include a threshold test 1615 that determines whether the amplitudes of the signals produced by the sensors are sufficient to indicate that a suspicious underlying structure may be present. In the threshold test, the signal amplitudes are compared to a threshold, and signals that exceed the threshold are evaluated differently from signals that do not exceed the threshold. The threshold is dynamic, e.g., is generated based on the signal amplitudes. The threshold test also determines whether an average of the signal amplitudes that exceed the threshold is within a predetermined range of amplitudes, and whether an average of the signal amplitudes that do not exceed the threshold exceeds a selected minimum amplitude. The threshold test passes if these averages are within the limits and exceed the selected minimum amplitude, respectively; otherwise the threshold test fails.

Edge filtering 1620 is applied to the signals that exceed the threshold to determine whether signals produced by sensors on the periphery of the array are valid or are instead due to "edge effects" caused by improper operation by the clinician. This is done by first finding a set of adjacent sensors arranged on the periphery that produce signals which exceed the threshold. This set of sensors is then compared to another set of adjacent sensors arranged in an interior of the array that produce signals which exceed the threshold. The signals produced by sensors arranged on the periphery are determined to be valid if the ratio of the total number of contiguous adjacent sensors which exceed the threshold to the number of adjacent sensors on the perimeter by a selected amount (e.g. 5). If the signals produced by the sensors on the periphery of the array are determined to be invalid, their amplitudes are reduced to below the threshold applied in the threshold test.

A continuity and size test 1625 determines whether any suspicious underlying regions are sufficiently large and sufficiently predominate nearby suspicious regions to warrant further testing. In the continuity and size test, the relative locations in the array of sensors that produce signals which exceed the threshold are identified. Then, a determination is made as to how many of these sensors are located adjacent to another sensor in the array that produces a signal which exceeds the threshold. The continuity and size test fails unless the number of such adjacent sensors exceeds a selected minimum number (e.g. 25); that is, unless the suspicious region has a selected minimum size. The continuity and size test also checks for the predominance of the suspicious region by computing the ratio of the number of such adjacent sensors to an aggregate of the number of such sensors and a number of nonadjacent sensors in the array that produce signals that exceed the threshold exceed by a selected amount and determining whether that ration exceeds a selected amount (e.g. 70%). If so, the continuity and size test passes; otherwise, the continuity and size test fails.

A ratiometric test 1630 determines whether the suspicious region is flat (as are normal structures such as the inframammary ridge) or peaked (as are foreign structures such as cysts and other lumps). The ratiometric test determines the maximum difference between the amplitudes of the signals that exceed the threshold, e.g., by determining a ratio between the signal having a highest amplitude and the signal having a lowest amplitude. The ratiometric test passes if this ratio exceeds a predetermined empirical threshold ratio (e.g., 1.7), and fails otherwise. If these tests have passed, a foreign structure in the frame has been identified or detected (step 1635). The frame is then stored for further analysis to discriminate whether the structure is a carcinoma (step 1640).

If a frame passes tests 1615, 1625, and 1630, the suspicious region or regions in the frame are deemed to correspond to a potentially foreign tissue structure (1635). DSP 24 stores a map of each suspicious region in memory 30 for further analysis in tests 1655, 1660 (step 1640). To reduce the risk of a false positive output, before subsequent tests 1655, 1660 are performed, a minimum number N (e.g. 3) of consecutive frames must pass tests 1615, 1625, or 1630 without interruption by a frame that fails one of tests 1615, 1625, or 1630. DSP 24 increments a frame counter (Step 1645) when a frame passes test 128. If the frame count exceeds N, e.g. 3, (Step 1650), DSP 24 proceeds to tests 1655 and 1665; if not, DSP 24 proceeds to step 1315, shown in FIG. 13A. The frame counter is reset to zero if any frame fails any test 1615, 1625, 1630.

As described above, the additional processing tests 1655, 1665 are performed only if the selected number (i.e. three) of the sets of signals are consecutively acquired without interruption by a frame of the signals that do not pass either the threshold, continuity and size, or ratiometric test (steps 1645 and 1650). This requirement helps reduce the possibility of false positive results.

The additional tests include a pressure profile test 1655 that examines pressure profiles of each suspicious region to determine whether the suspicious region has lump-like characteristics. A pair of pressure profiles are developed for each suspicious region by analyzing, for each of the sets of the signals, the amplitudes of the signals that exceed the threshold. Each pressure profile comprises signals produced by sensors in the array that are arranged along a selected dimension of a corresponding suspicious region. A first pressure profile is oriented along a dimension of maximum flatness of the region, and a second pressure profile is oriented along a dimension of minimum flatness of the region.

In the pressure profile test 1655, an edge profile, a relative stiffness, and a relative curvature of each suspicious region are determined based on the first and second pressure profiles. The edge profile is determined based on an amount that the amplitude of the signals change from sensor to sensor along the second pressure profile. The relative stiffness is obtained based on a difference between the signal having a highest amplitude and the signal having a lowest amplitude in the first pressure profile. The relative curvature is determined based on the flatness of the first pressure profile.

The edge profile, the relative stiffness, and the relative curvature of each suspicious region are evaluated with respect to each other, and an outcome is developed based on the evaluation. The outcome indicates a degree of membership of each suspicious region in a class of foreign tissue structures. That is, the outcome is not simply a binary result based on whether a given test "passes" or "fails"; rather, the degrees to which the standards applied by the tests are met by the suspicious region are evaluated and weighed (either equally, or not) to determine whether the characteristics of the region sufficiently resemble those of foreign tissue structures such as a lump. One example of a procedure for performing such an evaluation is a so-called "fuzzy logic" technique 1660, which employs neural network concepts for developing parameters of imprecise measurements.

The additional tests also include a motion filter test 1665 in which the sets of the signals are evaluated to determine the manner in which each of the suspicious regions moves with respect to the array as the array is moved over the tissue. This provides an indication of whether the regions are mobile in the body in a manner consistent with the mobility of lumps or other foreign structures. The motion filter test is performed by determining the distance and trajectory of each region's movement with respect to the array. The distance and trajectory of the suspicious region are evaluated with respect to each other, and an outcome is developed based on the evaluation that indicates a degree of membership of each suspicious region in a class of foreign tissue structures. Different weights may be assigned to the distance and trajectory determinations, or not. The edge profile, the relative stiffness, and the relative curvature of each suspicious region is also taken into account in developing the outcome. Preferably, the "fuzzy logic" 1660 techniques discussed above are used. It should be noted that the "fuzzy logic" techniques can use the results of both tests or only one of the tests, in either sequential or nonsequential manner.

If the results of the "fuzzy logic" analysis (step 1660) is negative and no suspicious areas are identified, DSP 24 proceeds to step 1315, shown in FIG. 13A (i.e. DSP 24 acquires a new frame).

However, if a suspicious area is identified by the "fuzzy logic" analysis (step 1660), DSP 24 proceeds to step 1365, shown in FIG. 13B. It should be noted that a "structure" indicator 660 in FIG. 6 may be lit when the first three tests have passed (i.e. a structure is detected and the tests for fuzzy logic analysis are performed) or when the fuzzy logic analysis discriminates a suspicious area.

Before describing step 1365—FIG. 17 shows the details of step 1365—we will first discuss what step 1365 is meant to achieve. Generally, one of the functions performed by device 10 in the second mode is providing a database and a map of the location of suspicious structures in the breast. Typically, when a structure in the breast causes a suspicious area to be detected in a frame, it will likely cause suspicious areas in other adjacent frames in the same sweep. Moreover, since as a result of the method of performing the examination, each area is covered at least twice, the same structure will likely cause suspicious areas to be detected in adjacent sweeps. In order to determine a location of underlying structure, it is necessary to combine those suspicious areas that represent the same underlying structure and to treat them as a single suspicious area. Step 1360 determines in a single sweep which suspicious areas correspond to the same underlying structure (i.e. axial integration), while step 1375 determines in adjacent sweeps which suspicious areas correspond to the same underlying structure (i.e. lateral integration). In each of these steps, the signal values corresponding to the same underlying structure are combined sensor by sensor to give an averaged or normalized pressure signature of the structure, i.e. single set of signal values representative of that underlying structure, as will be described in detail below.

Generally, in step 1365, whenever a suspicious area is detected or identified in step 1360, DSP 24 in step 1365 compares the location of the detected suspicious area to the location of the suspicious areas, if any, in the previous frame. If based on the proximity of the locations, DSP determines that they represent the same underlying structure, DSP 24 averages the signal values of the two areas on a sensor by sensor basis. This average is then stored in a database record together with an averaged out positional value. At the end of the sweep, this database contains a record for each underlying structure, if any, that was detected during the examination in that sweep.

At the end of the examination, a database contains a record for each suspicious area in each sweep. Therefore, after the clinician ends the exam, DSP 24 matches the suspicious areas laterally from sweep to sweep in step 1375. FIG. 19 shows in detail the steps DSP 24 performs to match the suspicious areas laterally. This procedure will be described in detail below. DSP 24 by performing steps 1365 and 1375 therefore generate a database in which the position of all the detected suspicious structures in the examined tissue are stored together with their locations.

Referring to FIGS. 13B and 17, we will now describe in detail how step 1365 matches suspicious areas identified in a sweep. In step 1365, DSP 24 analyzes an acquired frame to match suspicious areas in the frame to the immediately previous frame so that suspicious areas in each sweep which may correspond to the same foreign structure are matched to one another. DSP 24 calculates the average values including position, sensor values, pressure profile, and other variable for each suspicious area so as to create a temporary database of suspicious areas for a single sweep.

Referring to FIG. 17, DSP 24 first determines the center of each suspicious area and the lateral and axial values of the center of the suspicious area (step 1700). DSP 24 finds the center of suspicious areas in a frame by drawing a hypothetical rectangle around the suspicious area. The borders of the rectangle coincide with the outer most sensors of the suspicious area. DSP 24 then calculates the intersection of the two diagonals of the rectangle which is taken to be center of the suspicious area. Alternatively, the center of suspicious areas may be obtained using other standard techniques, such as a center of mass or a Centroid Weighted Technique. Lateral and axial values for the center of the suspicious area are then calculated by calculating the lateral and axial values of the sensor whose location coincides with the center of the suspicious area.

If the frame is the first frame in a sweep with a suspicious area (step 1705), there would not be any suspicious areas already identified in the sweep to match this suspicious area with. Therefore, DSP 24 proceeds to step 1750. In step 1750, DSP 24 inquires whether there are suspicious areas in the frame that have not been "labeled". As each suspicious area in a sweep is identified, a new record in a temporary database for that area is created and a reference to the frame and location of the suspicious area in that frame is stored in that record. Each record is identified by a "label" number that comprises of the sweep index number and an ordinal number sequentially assigned to each new suspicious area that does not match any suspicious areas in the frame. For example, the first suspicious area of the third sweep may have label number 3-1. The label number, which is essentially a database index number, can be used to refer to a record or to index or retrieve the record. In the case of the first suspicious area, since it is a suspicious area, it is assigned a new label in step 1755 and DSP proceed to step 1315 to acquire another frame.

If the frame is not the first frame with a suspicious area, then DSP 24 compares the center of each suspicious area in the current sweep with each suspicious area in the immediately previous sweep to determine which suspicious areas in the two frames correspond to the same foreign structure (step 1715).

One method of determining whether two suspicious areas in two frames represent the same structure in the breast is to determine their position in reference to a coordinate system. If the distance between the two centers is less than a threshold value, they likely correspond to the same structure. FIG. 18 is a flow chart of the test in step 1615 for determining if any suspicious areas in the current frame corresponds to the same structure as a suspicious area in the previous frame. Essentially, the steps in FIG. 18 check to see how close the two suspicious areas are. If they are closer than a pre-selected threshold, they are assumed to represent the same underlying structure. If not, they are assumed to represent different underlying structures.

DSP 24 first calculates the axial distance between the current frame and the previous frame, e.g. by calculating the distance of the centers of the two frames (step 1800). The following formula shows the calculation:

$$\Delta FP = FP_{current\ Frame} - FP_{Previous\ Frame}$$

where FP is the frame position. This distance dynamically determines a threshold for determining whether two suspicious areas are close enough axially to be considered to be pressure signatures of the same structure. Note that some structures such as soft or hard lumps move inside the tissue as sensor head 55 is translated over them. Therefore, the threshold is dynamically set based on the distance between the two frames.

DSP 24 then selects a suspicious area in the current frame to be compared to the suspicious area in the previous frame (step 1805). DSP 24 calculates the lateral axis component of the distance between the center of the suspicious area in the previous frame and the selected suspicious area in the current frame (step 1810), according to the following formula:

$$ABS(\Delta Fx) = ABS(Fx_{Current\ Frame} - Fx_{Previous\ Frame})$$

where Fx is the lateral value of the position of a suspicious area. If this distance is less than one centimeter, then the two area are considered to represent the same areas (step 1815). This threshold is not dynamic because it is unlikely that a foreign structure would move laterally as a result of the translation of sensor head 55. (This threshold may be changed so as to increase the accuracy of the system, either by making it dynamic or changing the value of the static threshold.) If the lateral component of the distance between the two suspicious areas falls below the threshold, DSP 24 computes the axial (i.e. y-axis) component of the distance (step 1820), according to the following formula:

$$\Delta Fy = Fy_{Current\ Frame} - Fy_{Previous\ Frame}$$

where Fy is the axial value of the position of a suspicious area. If the ΔFy value is less than one half the ΔFp value, (step 1825), then the two suspicious areas are considered to be the same. (This threshold may be changed so as to increase the accuracy of the system, either by changing the dynamic or changing it to a static threshold.) DSP 24 returns to step 1720 in FIG. 17.

If either the lateral or the axial component falls outside the required threshold, then DSP 24 determines whether there is another suspicious area in the frame to analyze. If so, DSP 24 performs the same analysis for the next suspicious area in the current frame. In this manner DSP 24 examines all suspicious areas against the suspicious area in the previous frame (step 1835). If no matching suspicious area is found, DSP 24 returns to step 1730 of FIG. 17.

If DSP 24 identifies both areas as the same suspicious area, it adds the suspicious area from the current frame to the suspicious area record (using a memory pointer stored with the frame) to which the suspicious area in the previous frame is linked (step 1720). A link is a reference, e.g. to a specific frame. A reference to the frame is stored in the temporary database record, and "links" the record to the frame. After linking the frame, DSP 24 determines whether all the suspicious areas in the frame have been examined (step 1725). If not, DSP 24 proceeds to examine the next suspicious area.

If a suspicious area in the previous frame does not find a counterpart in the current frame (step 1715), DSP 24 concludes that all the data regarding that suspicious area in this sweep has been gathered. DSP 24 uses the temporary suspicious area database record for that suspicious area to retrieve all the frames that are linked to it, i.e. all the frames that contained the pressure signatures for the suspicious area (step 1730). DSP 24 then calculates the average of the lateral and axial values by averaging the lateral and axial values of the center of the matching suspicious areas in the retrieved frames (step 1735). This average is assumed to be the location of the center of the underlying structure that corresponds to these suspicious areas.

DSP 24 next uses the pressure signatures from different frames to creates an average pressure signature for the suspicious area (step 1740). Because the suspicious areas from the different frames will likely have different shapes, DSP 24 maps the pressure signatures from different frames onto one another sensor by sensor and then calculates the average value for each sensor. To perform the mapping, DSP 24 creates a matrix in which each element may contain the pressure value of a sensor. DSP 24 selects a central element in the array to represent the center of a suspicious area. It then stores the sensor values of the suspicious area in the first linked frame such that the center of the suspicious area is loaded into the center element. The sensor values from each of the other sensors are loaded into a matrix element that bears the same relationship to the center element as the sensor bears to the center of the suspicious area. DSP 24 then loads the pressure signatures from the second linked frames so that the pressure value of its center is added to the center matrix element and each of the other sensors' pressure values are added to the matrix elements corresponding to the sensors. DSP 24 repeats this process until all pressure signatures for the specific suspicious area are added to the matrix. DSP 24 then averages the pressure values by dividing the value in each matrix element by the number of pressure signatures which were loaded.

The sweep number, the average center values and the average pressure signature values are then recorded in the suspicious area record (step 1745). Following this, referring back to FIG. 17, if all the suspicious areas in the new frame have been compared to all the suspicious areas in the new frame (step 1725), DSP 24 proceeds to step 1750. In that step, DSP 24 determines whether there are any suspicious areas in the frame that do not have a label, that is were not matched to any previous suspicious areas and are not associated with a database record. If not, the suspicious area is labeled, that is a new temporary database record for that area is created, and the next label number and a reference to the frame and location of the suspicious area in the frame is stored in the record (step 1755). DSP 24 then proceeds to step 1315 in FIG. 13 where it acquires a new frame.

We have so far described what DSP 24 does as the clinician translates the sensor head and performs the clinical breast examination. Referring back to FIG. 13A, as previously described, the clinician can end the exam at the end of any of the sweeps (step 1340). After the clinician has ended the exam, DSP 24 retrieves all the records in the temporary suspicious area database (step 1370). Since each area of the breast tissue is examined in at least two adjacent sweeps, in step 1375, DSP 24 laterally matches all the suspicious areas found during the examination. DSP 24 can then generate a database and a map for the suspicious area in the breast (it should be noted that in other embodiments only one or the other may be generated, or the physician may have the option to select generating a database, a map, or both). To do this, DSP 24 uses a methodology similar to that employed for matching suspicious areas in a single frame in step 1360.

As described, when the suspicious areas are matched axially in step 1360, each of the suspicious areas is assigned a label which is sequentially assigned to each new suspicious area. Moreover a suspicious area record for each suspicious area in a sweep is created in the suspicious area temporary database. Therefore, at the end of the examination, this database contains a record for each suspicious area identified in each sweep during the examination.

FIG. 19 shows the flow chart of the detailed operation of step 1375, where the suspicious areas are matched to one another. Generally, in a manner similar to the method in FIG. 17, the suspicious areas from adjacent sweeps are compared to one another and if they are closer than a pre-selected amount, they are assumed to represent the same underlying structure. The location and the pressure values of those suspicious areas that are matched to one another are averaged (or normalized) to supply an average location and average suspicious area.

To examine the adjacent sweeps to one another, DSP 24 selects a current and a compared sweep, starting with the first sweep as the compared sweep and the second sweep as the current sweep. DSP 24 compares each suspicious area in the compared sweep to each suspicious area in the current sweep. To do so, DSP 24 retrieves a suspicious area record belonging to the current sweep (step 1900) and a suspicious area in the compared sweep. (step 1905).

DSP 24 calculates a positional error value between the two suspicious areas using the difference between the lateral and axial values of the center of the two suspicious areas. To do this, DSP 24 calculates the difference between the axial values of the location of the suspicious areas (step 1910), using the following formula:

$$\Delta Axial = (Axial\ position_{current} - Axial\ Position_{Compared})$$

DSP 24 next calculates the difference between the lateral values of the location of the suspicious areas (step 1915), using the following formula:

$$\Delta Lateral = (Lateral\ position_{current} - Lateral\ Position_{compared})$$

DSP 24 then calculates the positional error (i.e. distance) between the centers of the two suspicious areas based on the results of the previous two steps, using the following formula (step 1920):

$$positional\ error = (\Delta Lateral^2 + \Delta Axial^2)^{1/2}$$

This value represents the positional error or distance between the centers of the two suspicious areas.

If the positional error between the two areas is not less than a predetermined radius of tolerance (e.g. 10 mm), then DSP 24 assumes that the two suspicious areas are pressure signatures of two different structures (step 1925). If there are more suspicious areas in the compared sweep to compare to the current sweep (step 1930), DSP 24 proceeds to step 1905 to compare the suspicious area in the current sweep with another suspicious area in the compared sweep (step 1930).

Since it is possible that two suspicious areas in the compared sweep are within the 10 mm radius of tolerance of the suspicious area for the current sweep. DSP 24 determines which suspicious area in the compared sweep is closest to the suspicious area in the current sweep that is currently being examined. To do this, DSP 24 first determines whether the positional error value is less than 10 mm (step 1925) and the positional error is the lowest for the suspicious area in the current sweep being currently examined (step 1935). If so, DSP 24 stores the positional error value and the suspicious area label in the temporary storage (step 1945) so that future positional errors for that suspicious area can be compared to that stored positional error value. Steps 1905–1945 are executed by DSP 24 until there are not any more suspicious areas in the compared sweep against which to compare the suspicious area from the current sweep to compare two (step 1930). If there is another suspicious are that has a lesser position error, it will replace the stored suspicious area in the temporary storage.

If there are no more suspicious areas are left in the compared sweep (step 1930), the suspicious area stored in temporary storage in step 1945 will be relabeled to have the label of the suspicious area from the current sweep under examination (step 1950). In other words, the frames belonging to the suspicious area are linked to the database record and the label number is changed to that of the suspicious area from the current sweep under examination. DSP 24 then averages the pressure signatures of the two suspicious areas using the superimposing technique previously described (step 1955). DSP 24 next determines the center of the averaged suspicious area (step 1960). DSP 24 stores the center and the average pressure signature of the suspicious area in an exam database (step 1965).

If nothing is stored in step 1945 in the temporary database, steps 1950–1965 do not result in any change in the status quo; that is, in essence, without anything being stored in step 1945, steps 1950–1965 are skipped. In step 1965, DSP 24 also purges the temporary storage to ready it for a new suspicious area in the current sweep.

If all the suspicious areas in the current sweep have not been compared to the suspicious areas in the previous sweep (step 1970), DSP 24 repeats the same procedure for the next suspicious area in the current sweep, i.e. steps 1900–1970. If all suspicious areas in the current sweep have been examined (step 1970), DSP determines if all the sweeps in the examination have been processed (step 1975). If all sweeps have not been examined, DSP 24 increments a sweep counter by one (step 1980). This causes the current sweep to become the current sweep and the last current sweep to become the compared sweep. DSP 24 then repeats steps 1900–1970 for a new pair of sweeps. When all the sweeps have been examined, DSP 24 returns to step 1380 in FIG. 13B.

At this point all the suspicious areas have been matched laterally and axially. The database contains a record for each detected underlying structure that contains an averaged pressure signature, the coordinates of the center of that signature relative the patient's body, and a link to all the frames which contain relevant signals for that suspicious structure.

Referring back to FIG. 13B, DSP 24 next calculates the pressure profile of these areas using the method summarized above in reference to step 1360 and described in detail in the '466 application (step 1380). The method is applied to the averaged pressure signatures. The values for each suspicious area are then recorded in a database, the records having the structure shown in FIG. 20. Each record of the database contains the lateral and axial coordinate values of the center of the suspicious area and a matrix containing the averaged pressure signature for that area. Moreover, the size of the suspicious are, calculated by counting the number of sensors in the matrix that has a pressure value above a threshold. The record of the database also contains the results of the profile test performed during the method of the '466 application. In other embodiments, the records contain the results of the fuzzy logic in the form of degree of membership or the results of the individual tests performed as part of the analysis under the method of the '466 application. The database records also have links to the location of the relevant frames for ease of future reference. In some embodiments, the database can be displayed or printed, e.g. to be included in the patient's chart.

All frame values are also recorded in an exam database. This database is stored in a long term storage device, such as a magnetic disk, for comparison with results from future examinations (step 1385). By storing all the examination data, it is possible to use more improved test to reexamine older data with newer techniques.

The clinician may now choose whether to display or print the results of the current examination in form of a map of the suspicious areas or whether to compare the results from the current examination with the results of a previous examination and display or print the results of that comparison in form of a database or a map (step 1390).

If the clinician chooses to display or print the results of the current examination (step 1390), then DSP 24 calculates the size of the examined area using the number of sweeps performed to determine the width of the examined area and the length of the longest sweep for the height of the examined area. DSP 24 then calculates a scaling factor for scaling the results of the current examination for displaying or printing (step 1391). DSP 24 then based on a selection by the clinician, displays the results on visual display 54 (FIG. 21) and/or printer 56 (FIG. 22) (step 1392). DSP 24 overlays the display or the printout with an anatomical outline and a reference coordinate system (step 1392).

FIG. 21 shows GUI 2100 including a map 2125 displayed on the monitor. Lateral and axial axes provide the clinician with reference point as to the location of suspicious areas. The suspicious area may be displayed, for example, as a mere dot, or as shown in FIG. 20, as an area proportionally displayed given its size. In other embodiments, the suspicious area may be displayed with a 3-D image with appropriate color scale for varying pressure.

A store button 2105, when clicked, allows the clinician to store the map as graphics, for example. A print button 2110, when clicked, allows the clinician to print the map. A compare button 2120 allows the clinician to begin comparing the results of the current examination with other previous examination of the same patient, as will be described below.

FIG. 22 shows a printed out map 2200. Map 2200 is printed with lateral and axial axes. Suspicious areas may be displayed in map 2200 in a variety of ways, as was the case for map 2125. In other embodiments, other information regarding various characteristics of the suspicious areas may also be printed. Such characteristic may include the results of the tests described in reference to FIG. 16, e.g. a degree of membership of a detected tissue in the class of carcinomas, manner of movement of the detected underlying structure as the plurality of sensor is moved over the tissue, an edge profile, a relative stiffness, a relative curvature of the detected tissue structure, etc. Other information may include the size of the areas. Such a map may placed in a patient's chart or provided to another clinician for review.

Referring back to FIG. 13B and also to FIG. 23, if the clinician chooses to compare the results of the current examination with the results of a previous examination (step 1390), DSP 24 performs a comparison of those results (step 1395).

FIG. 23 is the detailed steps taken as apart of step 1395. In order for DSP 24 to perform a comparison of the results of one examination to the results of another examination, DSP 24 first retrieves the frame data for the previous examination and creates a breast map in the same manner as the current exam (step 2300).

In different embodiments, the data may have be stored during an examination in a variety of formats. It may be in the form of raw or unprocessed signal readings or frames of signals. The data may also stored in a database as records of suspicious areas together with characteristic of the suspicious areas including the results of the tests described in reference to FIG. 16, e.g. a degree of membership of a detected tissue in the class of carcinomas, manner of movement of the detected underlying structure as the plurality of sensor is moved over the tissue, an edge profile, a relative stiffness, a relative curvature of the detected tissue structure, etc. Other stored information may include frames associated with the records, location of the suspicious areas, size of the areas, etc.

If the data is stored in raw signal format, it will be processed as if it represented a current exam. Even if the data is in form of records representing discriminated structures, the associated frames, if any, may still be reprocessed. Such reprocessing allows for improved better detection in the case of improvements in technology.

DSP 24 next matches suspicious areas in the current examination with suspicious areas in the retrieved examination to determine which suspicious areas likely correspond to the same underlying structure (step 2305). To do this, DSP 24 performs a matching technique similar to one used for matching suspicious areas from different sweep to one another. We will describe in detail the matching technique in reference to FIG. 24. Briefly, as part of this method, a suspicious area from the current examination is compared to all suspicious areas found in the previous exam. If the distance between two suspicious areas is sufficiently small according to preselected criteria, DSP 24 assumes that they represent the same underlying tissue structure. In that case, DSP 24 associates the records of the two suspicious areas with one another and compares them and their characteristics. If a suspicious area is not sufficiently close to any suspicious area in the other exam, that suspicious area is not associated with any other suspicious area. These areas are of particular interest. If a suspicious area in the current is not matched up with another suspicious area, it represents a newly identified structure, potentially a growing carcinoma. If a suspicious area in the previous examination is not matched up with one in the current exam, it may have been a false positive or a structure like a cyst whose size and characteristic typically varies, for example, with the patient's menstrual cycle.

After examining all suspicious areas found in the current examination, DSP 24 creates a database and a map of the breast and the identified suspicious areas. The clinician may have the results, including the map, visually displayed (as in FIG. 25), printed out (as in FIG. 26), or both.

We will now describe in detail, in reference to FIG. 23, the steps taken to perform step 2305 in FIG. 23. The method in FIG. 23 closely resembles the method disclosed in FIG. 19, where suspicious areas from adjacent sweeps are matched.

Steps 2400 to 2430 are similar to steps 1900–1930, except that suspicious areas from two exams rather than two sweeps are compared. DSP 24 first retrieves a suspicious area record from the current examination database (step 2400) and a suspicious area record from the previous examination database (step 2405). DSP 24 calculates a positional error value between the location of the two suspicious areas in steps 2410–2420 in the same manner as in steps 1919–1920 of FIG. 19, as described above. This value represents the distance between the two areas if the maps from the two examinations were superimposed on one another. If the positional error between the two areas is less than a predetermined radius of tolerance (e.g. 10 mm), then DSP 24 determines the two suspicious areas may be pressure signatures of the same structure and should be further tested in step 2435 (step 2425). DSP 24 proceeds to step 2435 to determine whether the positional error is the lowest value found for the suspicious area being tested. This step is performed since it is possible that another suspicious area from the previous examination may be even closer in distance to the suspicious area from the current examination being tested. If the positional error is the lowest value found for the suspicious area being tested, DSP 24 stores the suspicious area label to identify the area later, as needed, and the positional error value associated with that suspicious area as having the lowest positional error value.

After DSP 24 performs steps 2425, 2435, and 2440, DSP 24 proceeds to step 2405 to determine whether there are more suspicious areas in the previous examination to be matched against the suspicious area form the current exam for which a match is sought (step 2405). If there are, DSP 24 retrieves another suspicious area record from the previous examination database (step 2405) to check against the suspicious area from the current examination.

If there are not any suspicious areas from the previous examination left to be tested, DSP 24 determines whether any suspicious area from the previous exam was matched to the suspicious area from the current exam that was being examined (step 2445). If there is matching suspicious area from the previous exam, the matching suspicious area record from the previous examination is linked (e.g. via a memory location pointer or record label pointer) to the suspicious area record from the current examination for which the match was sought (step 2450). DSP 24 then computes the size of the two areas and compares them to determine any changes from the previous examination (step 2455). DSP 24 also performs a variety of tests, in accordance with the method in '466, application on the frames of signals for the suspicious area from the previous examination to determine its various characteristics and determines the results of the fuzzy logic analysis (step 2460). DSP 24 then compares the computed values for the two suspicious areas to determine any change (step 2460). This comparison includes comparing the final result of analysis from the '466 application which is identifying whether the area is a possible carcinoma or not. It also includes comparing some or all of the results from each stage of the testing according to the method in the '466 application.

If the suspicious area from the current is not matched with any suspicious area from the previous examination (2445), the suspicious area record is not linked with any suspicious area from the previous examination.

DSP 24 after performing steps 2445–2460 then determines whether all suspicious areas from the current exam have been tested (step 2465). If not, DSP 24 proceed to retrieve another suspicious area record (step 2400) and attempt to find a matching suspicious area from the previous examination.

If all suspicious areas from the current examination have been tested (step 2465), DSP 24 identifies those areas in the current and previous examinations for which no match is found (step 2470). Unmatched suspicious areas in the current exam represent structures of special concern because they may represent new carcinoma. Unmatched areas from the previous exam may represent "false positive" in the previous exam. For example, some cysts grow and shrink with hormonal changes during menstrual cycle. Therefore, they may be identified as suspicious during a previous examination but not so in a current exam.

It should be noted that data stored during the previous examination may take the form of a variety of formats. For example, the data may be the raw, un-processed signal values. These values are then processed according to the method disclosed herein. The data may also be records of the suspicious areas with no associated frames of signals, or with associated frames of signals. An advantage of processing previously stored signal values is that as technology progresses, the signals may be reanalyzed using the newest technology.

Referring back to FIG. 23, DSP 24 next determines a scaling factor for displaying the results (step 2310). The scaling factor is determined in the same manner as step 1391 in FIG. 13, which was described above. DSP 24 then displays and/or prints, based on the clinician's option, the results from both examinations (step 2315). The clinician next has the choice of choosing to compare the results from the current examination with the results from other examinations, for example, to compare the change over a five year period (step 2320).

FIG. 25 shows an example of a GUI 2500 illustrating how the results of comparison of an examination with previous examinations are displayed. Map 2505 shows the results of the current examination, while maps 2510 and 2515 respectively show the results of a first and second previous examinations. In the particular example in FIG. 25, a suspicious area that has been labeled during the current examination with the label number 1 has been matched to suspicious areas in the two previous exam. Therefore, those area also displayed with the label number 1 in maps 2510 and 2515. This type of simultaneous displaying and matching provides significant clues as to the nature of a detected tissue structure to a clinician. In this case, the suspicious area having the label number 1 is growing. Since an important identifying characteristic of a carcinoma is the fact that it grows, the simultaneous display of the matched areas provides an easily identifiable visual clue to the clinician of the possible growth of a tissue structure.

This visual display is augmented by the displaying of the results of comparisons between the characteristic from the current and previous examinations are displayed in box 2520, in form of a database. The results of comparison with the first exam 2525 (which is the more current previous exam) shows a percent area change of 23% while changed in the result of fuzzy logic analysis of 34% (i.e. 34% more likely that it is a carcinoma). The results of comparison with the older exam 2530 (i.e. the second previous exam) shows 37% increase in size and 52% increase in the likelihood that it is a carcinoma. Therefore, the clinician is provided with quantitative information he may analyze, record or communicate to others. The clinician is also assisted in reconfirming the detection in size that he may have detected or the carcinoma diagnosis.

A new suspicious area, which indicates a sudden growth suggestive of a carcinoma is prominently displayed. Of course for such an area no comparative results are available. It should be noted that the "Data" button 2540 may be used so that if pressed by the clinician, the clinician can view the data from any of the examinations for a specific detected suspicious area displayed according to the first mode of operation.

In other embodiments, the display may be different. For example, suspicious areas from the current examination may be displayed in one color (e.g. red) and those from the previous examination may be underlaid in another color (e.g. yellow). In that case, the suspicious areas which have been matched and compared are indicated as such and those results displayed or printed with them. The clinician may also have the choice of displaying maps of the current or the previous examinations. The visual display of the map may also be enhanced in a variety of ways to further assist the clinician FIG. 26 shows an example illustrating how a printout of the results of comparison of two examinations may appear. In this case, the previous 2610 and current 2605 pressure signatures of a tissue structure identified as a carcinoma are displayed as overlaying one another. The computed percentage changes are also displayed. Moreover, a new suspicious structure is identified as such and prominently pointed out. In other embodiments, the printout may also resemble GUI 2500 or be enhanced in other ways to further assist the clinician.

FIG. 25 shows a GUI 2500 of the compare mode.

Other embodiments are within the scope of the following claims.

In an alternative embodiment of the tissue examination device and the second mode of analysis, device 10 uses 3-D positioning devices (also known as Coordinate Measuring Machine (CMM) and stereotactic measuring devices), technology to provide external reference point for performing the examination. A tracking device is located in a fixed location in the examination room. Sensor head 55 is attached to the positioning device via receptor handles. The tracking device is able to locate the position of sensor head 55 relative to its own position and also determine the vector or the direction the sensor head is facing. This information is supplied to DSP 24. Prior to performing the examination, the clinician initializes device 10 by providing the position of three reference points on the patient's anatomy (e.g. two shoulder joints and lowest point of sternum) to DSP 24 by placing an indicator on the sensor head 55 over these areas. DSP 24 then is able to determine the position of sensor head 55 with respect to these three points. DSP 24 is then able to create a breast map using this positional information. In this embodiment, the clinician can move the sensor head in any direction when performing the examination.

In this embodiment, DSP 24 can also measure the torque imposed on the device based on the force on the array, the velocity of the movement, and the vector information from the tracking device. Generally, deep structures impose a toque on the sensor head for a longer distance of translation than shallow structures. Therefore, DSP 24 can use the torque measurement to determine the depth of the structure being measured. Because the depth of the structure can distort the pressure reading, making a deep hard lump to appear as shallow soft lump, DSP 24 can use the depth measurement to correct for the effects of the depth on the image and to normalize the image for a uniform depth. Using an optical metaphor, DSP in essence refocuses the sensors.

What is claimed is:

1. A method for performing tissue examination comprising:
pressing a plurality of sensors against a surface of a selected region of tissue to impose on the sensors pressure that varies in accordance with properties of tissue structures underlying the surface in the region and cause the sensors to respectively generate signals having levels that represent the pressure imposed thereon,
generating an image from the signals generated by the sensors, the image comprising areas that respectively correspond to relative locations of the sensors and have attributes according to the levels of the signals generated by the respective sensors so that the image represents a spatial pressure profile of the selected region of tissue, and displaying said image, and
processing the signals generated by the sensors to detect an underlying tissue structure in the selected region of tissue.

2. The method of claim 1 wherein the image comprises a 3-dimensional image, said areas being arranged in two of the dimensions and said attributes being arranged in the third dimension.

3. The method of claim 1 wherein the processing step comprises discriminating the detected underlying tissue structure as one of a plurality of different types of underlying tissue structures.

4. The method of claim 3 wherein the discriminating step comprises discriminating the detected tissue structure based on characteristics corresponding to the detected tissue structure.

5. The method of claim 4 wherein the characteristics comprise at least one of a manner of movement of the detected underlying structure as the plurality of sensors are moved over the tissue, an edge profile, a relative stiffness, and a relative curvature of the detected tissue structure.

6. The method of claim 4 wherein the discriminating step further comprises determining a degree of membership of the detected tissue structure in a preselected class of tissue structures corresponding to the discriminated type.

7. The method of claim 1 further comprising determining a location of the detected underlying tissue structure relative to a reference point, and storing a record in a database, wherein the record includes a result of the processing step and the location of the detected tissue structure relative to a reference point.

8. The method of claim 1 wherein the attributes comprise at least one graphical feature that represents variance in the pressure imposed on the sensors.

9. A method for performing tissue examination comprising:
pressing a plurality of sensors against a selected region of tissue of a person to cause the sensors to generate signals in response to pressure imposed thereon by the pressing, the pressure varying in accordance with properties of different types of underlying tissue structures,
processing the signals generated by the sensors to detect an underlying tissue structure in the region of tissue,
generating positional signals indicative of a position of the sensors, and
processing the positional signals to determine a location of the detected underlying tissue structure relative to an anatomical feature of the person.

10. The method of claim 9 further comprising storing a record in a database, wherein the record includes a characteristic corresponding to the detected tissue structure and the location of the detected tissue structure.

11. The method of claim 10 wherein the characteristic comprises at least one of size, manner of movement of the detected underlying structure as the plurality of sensor is moved over the tissue, an edge profile, a relative stiffness, and a relative curvature of the detected tissue structure.

12. The method of claim 10 further comprising storing a plurality of records in a database, one of the records comprising a characteristic corresponding to the detected tissue structure and the location of the detected.

13. The method of claim 12 wherein the processing step comprises discriminating the detected underlying tissue structure as one of a plurality of different types of underlying tissue structures and storing a result of the discriminating step in the one of the records.

14. The method of claim 13 wherein the discriminating step comprises discriminating the detected tissue structure based on characteristics corresponding to the detected tissue structure.

15. The method of claim 14 wherein the discriminating step further comprises determining a degree of membership of the detected tissue structure in a class of tissue structures corresponding to the discriminated type.

16. The method of claim 9 further comprising:
processing the determined location to produce a map of the location of the detected tissue structure.

17. The method of claim 16 further comprising displaying the map.

18. The method of claim 17 wherein the displaying step comprises printing the map.

19. The method of claim 17 wherein the displaying step comprises displaying the map on a visual display.

20. The method of claim 17 wherein the displaying step comprises displaying a characteristic of a group of the signals corresponding to the detected tissue structure in relation to the location of the detected tissue structure.

21. The method of claim 20 wherein the characteristic of the detected tissue structure comprises at least one of size, edge profile, relative stiffness, relative curvature of the detected tissue structure, and a manner of movement of the detected underlying structure as the plurality of sensor is moved over the tissue.

22. The method of claim 17 wherein the processing step comprises discriminating the detected underlying tissue structure as one of a plurality of different types of underlying tissue structures and the displaying step comprises displaying a result of the discriminating step in relation to the detected tissue structure.

23. The method of claim 22 wherein the discriminating step further comprises determining a degree of membership of the detected tissue structure in a preselected class of tissue structures corresponding to the discriminated type and the displaying step comprises displaying the degree of membership in relation to the detected tissue structure.

24. The method of claim 9 further comprising:
retrieving data representing a previous tissue examination, wherein the data was previously stored during the previous examination, and
using the data with the determined location.

25. The method of claim 24 wherein the retrieved data comprises data representative of signals generated by sensors during a previous examination.

26. The method of claim 24 wherein the retrieved data comprises a result of processing signals in the previous tissue examination to discriminate an underlying tissue structure as one of a plurality of different types of underlying tissue structures.

27. The method of claim 24 wherein the retrieved data further comprises a location of a detected tissue structure in the previous tissue examination relative to the anatomical feature.

28. The method of claim 24 wherein the retrieved data further comprises a degree of membership of a detected tissue in the previous tissue examination in a preselected class of tissue structures.

29. The method of claim 24 further comprising the step of:
processing the retrieved data to generate a first map of a location of a tissue structure detected based on the previously stored data, wherein the first map is generated relative to the anatomical feature,
processing the determined location to produce a second map of the location of the detected tissue structure, and
displaying the first and second maps.

30. The method of claim 24 wherein the processing further comprises discriminating the first-mentioned detected underlying tissue structure as one of a plurality of different types of underlying tissue structures and the method further comprises:
discriminating the detected underlying tissue structure as one of a plurality of different types of underlying tissue structures,
processing the retrieved data to discriminate a second underlying tissue structure in the region of the tissue as the one of the plurality of different types of underlying tissue structures
determining whether the first mentioned underlying tissue structure and the second underlying tissue structure are a same underlying tissue structure.

31. The method of claim 30 further comprising:
if the first-mentioned and second discriminated underlying tissue structures are determined to be the same underlying tissue structure, processing signals corresponding to the first-mentioned discriminated underlying tissue structure with the data corresponding to the second discriminated underlying tissue structure to determine changes corresponding to the same underlying tissue structure between the previous and a current examination.

32. A method for examining tissue, comprising
pressing a plurality of sensors against a surface of a selected region of tissue to impose on the sensors pressure that varies in accordance with properties of tissue structures underlying the surface in the region and cause the sensors to respectively generate signals having levels that represent the pressure imposed thereon, generating an image from the signals generated by the sensors, the image comprising areas that respectively correspond to relative locations of the sensors and have attributes according to the levels of the signals generated by the respective sensors so that the image represents a spatial pressure profile of the selected region of tissue, and
displaying the generated image.

33. The method of claim 32 wherein the step of displaying the image comprises displaying the image attributes as a pre-selected range of colors that correspond to the attributes.

34. The method of claim 32 wherein the step of displaying of the image comprises displaying a shape representative of an underlying tissue structure in the region as part of the image.

35. The method of claim 34 further comprising detecting the underlying tissue structure and displaying an outline of the shape based on the detecting step.

36. The method of claim 32 wherein the step of displaying the image comprises displaying a value corresponding to a peak pressure represented in the image.

37. The method of claim 32 wherein the step of displaying the image comprises displaying a gradient of a portion of the image.

38. The method of claim 32 wherein the step of displaying the image comprises printing the image.

39. The method of claim 32 wherein the step of displaying the image comprises displaying the image on a visual display.

40. The method of claim 32 wherein the attributes comprise at least one graphical feature that represents variance in the pressure imposed on the sensors.

41. The method of claim 32 wherein the image comprises a 3-dimensional image, said areas being arranged in two of the dimensions and said attributes being arranged in the third dimension.

42. The method of claim 41 wherein the step of displaying the image comprises displaying a top view of the three dimensional image.

43. The method of claim 41 wherein the step of displaying the image comprises displaying a perspective view of the three dimensional image.

44. The method of claim 32 wherein the pressing step comprises:
pressing the sensors, at a first position, against the selected region of tissue to cause the sensors to generate a first plurality of signals that represent the pressure imposed thereon;
moving the sensors from the first position to a second position,
generating positional signals indicative of the first and second positions of the sensors,
pressing the sensors, at the second position, against the selected region of tissue to cause the sensors to generate a second plurality of signals that represent the pressure imposed thereon,
processing the positional signals, the first plurality of signals, and the second plurality of signals, to generate the image so that the image represents a composite of spatial pressure profiles of the selected region with the sensors in the first and second positions, respectively.

45. The method of claim 44 wherein said processing includes correlating a portion of the first plurality of signals to a portion of the second plurality of signals based on the positional signals.

46. A method for performing a clinical breast examination using a tissue examination device, wherein the tissue examination device comprises a plurality of sensors, a processor, and a display, comprising pressing the plurality of sensors against a surface of a selected region of tissue to impose on the sensors pressure that varies in accordance with properties of tissue structures underlying the surface in the region and cause the sensors to respectively generate signals having levels that represent the pressure imposed thereon, processing, by the processor, the signals generated by the sensors to generate an image from the signals, the image comprising areas that respectively correspond to relative locations of the sensors and have attributes according to the levels of the signals generated by the respective sensors so that the image represents a spatial pressure profile of the selected region of tissue, displaying the image with the display, and examining a shape in the displayed image of the spatial pressure profile to identify a selected type of underlying tissue structures.

47. The method of claim 46 wherein the step of examining the shape comprises attempting to identify a characteristic of the shape, wherein the characteristic suggests a degree of membership of an underlying tissue structure in a class of tissue structures.

48. The method of claim 47 wherein the characteristic is selected among a plurality of characteristics including:
size of the shape;
height of the shape's various areas;
flatness of the shape;
peakedness of the shape;
whether the shape has a plateau;
outline of the shape;
contour of the shape;
a gradient along any part of the shape;
movement of the shape in response to the moving or rolling the sensors over the tissue; and
change in the shape in response to changing the imposed pressure.

49. The method of claim 47 wherein the class of tissue structures is selected among a group of classes of tissue structures including carcinoma, ribs, cysts, inframammary ridges, hard lumps, and soft lumps.

50. The method of claim 46 wherein examining the shape further comprises identifying a discrete, dominant, or different characteristic of the shape.

51. The method of claim 46 wherein the selected type of underlying tissue structure comprises carcinoma, and examining a displayed shape comprises identifying a characteristic selected among a plurality of carcinoma characteristics including:
peaked shape,
low gradient between edges and a peak of the displayed shape, relative to other shapes,
small movement of the shape in response to moving of the sensors over the tissue, relative to the other shapes,
small change in the shape in response to changing the imposed pressure, relative to the other shapes, and
growth of the shape over time.

52. The method of claim 51, wherein examining a the shape comprises identifying a discrete, dominant, or different carcinoma characteristic of the shape, and
determining whether the shape represents an underlying carcinoma based on the identified discrete, dominant, or different carcinoma characteristic in the shape.

53. The method of claim 46 wherein the image comprises a 3-dimensional image, said areas being arranged in two of the dimensions and said attributes being arranged in the third dimension.

54. A tissue examination device comprising:
a plurality of sensors which generate signals when pressed against a surface of a selected region of tissue to impose on the sensors pressure that varies in accordance with properties of tissue structures underlying the surface in the region, the signals having levels that represent the pressure imposed on the respective sensors,
a processor for (1) generating an image from the signals generated by the sensors, the image comprising areas that respectively correspond to relative locations of the sensors and have attributes according to the levels of the signals generated by the respective sensors so that the image represents a spatial pressure profile of the selected region of tissue, and (2) processing the signals generated by the sensors to detect an underlying tissue structure in the selected region of tissue, and a display for displaying the image.

55. The device of claim 54 wherein the image comprises a 3-dimensional image, said areas being arranged in two of the dimensions and said attributes being arranged in the third dimension.

56. The device of claim 54 wherein the processor discriminates the detected underlying tissue structure as one of a plurality of different types of underlying tissue structures.

57. The device of claim 56 wherein the processor discriminates the detected tissue structure based on characteristics corresponding to the detected tissue structure.

58. The device of claim 57 wherein the characteristics comprise at least one of a manner of movement of the detected underlying structure as the plurality of sensor are moved over the tissue, an edge profile, a relative stiffness, and a relative curvature of the detected tissue structure.

59. The device of claim 57 wherein the processor determines a degree of membership of the detected tissue structure in a preselected class of tissue structures corresponding to the discriminated type.

60. The device of claim 54 wherein the processor determines a location of the detected underlying tissue structure relative to a reference point, and stores a record in a database, wherein the record includes a result of the processing by the processor and the location of the detected tissue structure relative to a reference point.

61. The device of claim 54 wherein the attributes comprise at least one graphical feature that represents variance in the pressure imposed on the sensors.

62. A device for performing tissue examination comprising:
a plurality of sensors which generate signals in response to pressure imposed thereon when pressed against a selected region of tissue of a person, the pressure varying in accordance with properties of underlying tissue structures,
a position indicator generating positional signals indicative of a position of the sensors, and
a processor for processing the signals generated by the sensors to detect an underlying tissue structure in the region of tissue, and processing the positional signals to determine a location of the detected underlying tissue structure relative to an anatomical feature of the person.

63. The device of claim 62 wherein the processor stores a record in a database, wherein the record includes a characteristic corresponding to the detected tissue structure stored and the location of the detected tissue structure.

64. The device of claim 63 wherein the characteristic comprises at least one of size, manner of movement of the detected underlying structure as the plurality of sensor is moved over the tissue, an edge profile, a relative stiffness, and a relative curvature of the detected tissue structure.

65. The device of claim 63 wherein the processor stores a plurality of records in a database, one of the records comprising a characteristic corresponding to the detected tissue structure and the location of the detected.

66. The device of claim 65 wherein the processor discriminates the detected underlying tissue structure as one of a plurality of different types of underlying tissue structures and stores a result of the discriminating by the processor in the one of the records.

67. The device of claim 66 wherein the processor discriminates the detected tissue structure based on characteristics corresponding to the detected tissue structure.

68. The device of claim 67 wherein the processor determines a degree of membership of the detected tissue structure in a class of tissue structures corresponding to the discriminated type.

69. The device of claim 62 further comprising the processor processing the determined location to produce a map of the location of the detected tissue structure.

70. The device of claim 69 further comprising a display for displaying the map.

71. The device of claim 70 wherein the display comprises a printer for printing the map.

72. The device of claim 71 wherein the display comprises a visual display for displaying the map.

73. The device of claim 70 wherein the display displays a characteristic of a group of the signals corresponding to the detected tissue structure in relation to the location of the detected tissue structure.

74. The device of claim 73 wherein the characteristic of the detected tissue structure comprises at least one of size, edge profile, relative stiffness, relative curvature of the detected tissue structure, and a manner of movement of the detected underlying structure as the plurality of sensor is moved over the tissue.

75. The device of claim 70 wherein the processor discriminates the detected underlying tissue structure as one of a plurality of different types of underlying tissue structures and the display displays a result of the processor discriminating in relation to the detected tissue structure.

76. The device of claim 75 wherein the processor determines a degree of membership of the detected tissue structure in a preselected class of tissue structures corresponding to the discriminated type and the display displays the degree of membership in relation to the detected tissue structure.

77. The device of claim 62 wherein the processor retrieves data representing a previous tissue examination, wherein the data was previously stored during the previous examination, and uses the data with the determined location.

78. The device of claim 77 wherein the retrieved data comprises data representative of signals generated by sensors during a previous examination.

79. The device of claim 77 wherein the retrieved data comprises a result of processing signals in the previous tissue examination to discriminate an underlying tissue structure as one of a plurality of different types of underlying tissue structures.

80. The device of claim 77 wherein the retrieved data further comprises a location of a detected tissue structure in the previous tissue examination relative to the anatomical feature.

81. The device of claim 77 wherein the retrieved data further comprises a degree of membership of a detected tissue in the previous tissue examination in a preselected class of tissue structures.

82. The device of claim 77 wherein the processor:
discriminates the detected underlying tissue structure as one of a plurality of different types of underlying tissue structures,
processes the retrieved data to generate a first map of a location of a tissue structure detected based on the previously stored data, wherein the map of the location is generated relative to the anatomical feature, and
processes the determined location to produce a second map of the location of the detected tissue structure, and
wherein the display displays the first and second maps.

83. The device of claim 77 wherein the processor:
discriminates the first-mentioned detected underlying tissue structure as one of a plurality of different types of underlying tissue structures,
processes the retrieved data to discriminate a second underlying tissue structure in the region of the tissue as the one of the plurality of different types of underlying tissue structures, and
determines whether the first mentioned underlying tissue structure and the second underlying tissue structure are a same underlying tissue structure.

84. The device of claim 83 wherein if the first-mentioned and second discriminated underlying tissue structures are determined to be the same underlying tissue structure, the processor processes signals corresponding to the first-mentioned discriminated underlying tissue structure with the data corresponding to the second discriminated underlying tissue structure to determine changes corresponding to the same underlying tissue structure between the previous and a current examination.

85. A tissue examination device comprising
a plurality of sensors which generate signals when pressed against a surface of a selected region of tissue to impose on the sensors pressure that varies in accordance with properties of tissue structures underlying the surface in the region, the signals having levels that represent the pressure imposed on the respective sensors,
a processor for generating an image from the signals generated by the sensors, the image comprising areas that respectively correspond to relative locations of the sensors and have attributes according to the levels of the signals generated by the respective sensors so that the image represents a spatial pressure profile of the selected region of tissue, and
a display for displaying the image.

86. The device of claim 85 wherein the display displays the image attributes as a pre-selected range of colors that correspond to the attributes.

87. The device of claim 85 wherein the display displays a shape representative of an underlying tissue structure in the region as part of that image.

88. The device of claim 87 wherein the processor detects the underlying tissue structure and displays an outline of the shape based on the detection.

89. The device of claim 82 wherein the display displays a value corresponding to a peak pressure represented in the image.

90. The device of claim 85 wherein the display displays a gradient of a portion of the image.

91. The device of claim 85 wherein the display comprises a printer for printing the image.

92. The device of claim 85 wherein the display displays the image on a visual display.

93. The device of claim 85 wherein the attributes comprise at least one graphical feature that represents variance in the pressure imposed on the sensors.

94. The device of claim 85 wherein the image comprises a 3-dimensional image, said areas being arranged in two of the dimensions and said attributes being arranged in the third dimension.

95. The device of claim 94 wherein the display displays a top view of the three dimensional image.

96. The device of claim 94 wherein the display displays a perspective view of the three dimensional image.

97. The device of claim 85 further comprising a position indicator, wherein the sensors when pressed at a first position against the selected region of tissue generate a first plurality of signals that represent the pressure imposed thereon, and the sensors when moved to a second position and pressed against the selected region of tissue generate a second plurality of signals that represent the pressure imposed thereon, the position indicator generates positional signals indicative of the first and second positions of the sensors, and the processor processes the positional signals, the first plurality of signals, and the second plurality of signals, to generate the image so that the image represents a composite of spatial pressure profiles of the selected region with the sensors in the first and second positions, respectively.

98. The device of claim 97 wherein the processor correlates a portion of the first plurality of signals to a portion of the second plurality of signals, based on the positional signals, to generate the pressure profile of the selected region.

* * * * *

UNITED STATES PATENT AND TRADEMARK OFFICE
CERTIFICATE OF CORRECTION

PATENT NO. : 6,091,981
DATED : July 18, 2000
INVENTOR(S) : Cundari et al.

It is certified that error appears in the above-identified patent and that said Letters Patent is hereby corrected as shown below:

Column 5,
Line 36, after "with" delete "the".

Column 9,
Line 39, replace "2.51" with -- 2.5 --.

Column 14,
Line 57, replace "hardshelled" with -- hard shelled --.

Column 39,
Line 67, delete "a".

Column 42,
Line 55, replace "that" with -- the --.
Line 59, replace "82" with -- 85 --.

Signed and Sealed this

Tenth Day of May, 2005

JON W. DUDAS
*Director of the United States Patent and Trademark Office*